United States Patent
Poitout et al.

(10) Patent No.: US 7,495,009 B2
(45) Date of Patent: Feb. 24, 2009

(54) IMIDAZOPYRIDINE DERIVATIVES AS MELANCORTIN RECEPTOR AGONISTS

(75) Inventors: Lydie Poitout, Le Kremlin Bicetre (FR); Valérie Brault, Saint-Arnoult-En-Yvelines (FR); Carole Sackur, Paris (FR); Pierre Roubert, Paris (FR); Pascale Plas, Chatillon (FR)

(73) Assignee: Societe de Conseils de Recherches et d'Applications Scientifiques (S.C.R.A.S.), Paris (FR)

( * ) Notice: Subject to any disclaimer, the term of this patent is extended or adjusted under 35 U.S.C. 154(b) by 399 days.

(21) Appl. No.: 10/550,122

(22) PCT Filed: Mar. 29, 2004

(86) PCT No.: PCT/FR2004/000785

§ 371 (c)(1), (2), (4) Date: Sep. 19, 2005

(87) PCT Pub. No.: WO2004/089951

PCT Pub. Date: Oct. 21, 2004

(65) Prior Publication Data

US 2006/0173036 A1 Aug. 3, 2006

(30) Foreign Application Priority Data

Mar. 31, 2003 (FR) .................................. 03 03924

(51) Int. Cl.
*A61K 31/44* (2006.01)
*C07D 471/02* (2006.01)
*C07D 491/02* (2006.01)
*C07D 498/02* (2006.01)
*C07D 513/02* (2006.01)
*C07D 515/02* (2006.01)

(52) U.S. Cl. ...................................... 514/303; 546/118
(58) Field of Classification Search ................ 514/303; 546/118

See application file for complete search history.

(56) References Cited

U.S. PATENT DOCUMENTS 6,350,760 B1  2/2002 Bakshi et al.

FOREIGN PATENT DOCUMENTS

| WO | PCT/US01/17014 | 12/2001 |
| WO | 2002060879 | * 8/2002 |
| WO | PCT/USO1/48856 | 8/2002 |

OTHER PUBLICATIONS

Vergoni et al., European Journal of Pharmacology (1999), 369(1), 11-15.*

* cited by examiner

*Primary Examiner*—Janet L Andres
*Assistant Examiner*—Niloofar Rahmani
(74) *Attorney, Agent, or Firm*—Charles A. Muserliar

(57) ABSTRACT

Derivatives of imidazopyridine which have a good affinity for certain sub-types of melanocortin receptors, in particular MC4 receptors and are useful for treating pathological states and diseases in which one or more melanocortin receptors are involved and pharmaceutical compositions containing said products.

22 Claims, No Drawings

IMIDAZOPYRIDINE DERIVATIVES AS MELANCORTIN RECEPTOR AGONISTS

This application is a 371 of PCT FR2004/000785 filed Mar. 29, 2004.

A subject of the present application is novel imidazo-pyridine derivatives. These products have a good affinity for certain sub-types of melanocortin receptors, in particular MC4 receptors. They are particularly useful for treating the pathological states and diseases in which one or more melanocortin receptors are involved. The invention also relates to pharmaceutical compositions containing said products and their use for the preparation of a medicament.

The melanocortins represent a group of peptides which derive from the same precursor, proopiomelanocortin (POMC), and which are structurally close: adrenocorticotropic hormone (ACTH), α-melanocyte-stimulating hormone (α-MSH), β-MSH and γ-MSH (Eipper B. A. and Mains R. E., *Endocr. Rev.* 1980, 1, 1-27). The melanocortins perform numerous physiological functions. They stimulate the synthesis of steroids by the adrenal cortex and the synthesis of eumelanin by the melanocytes. They regulate food intake, energy metabolism, sexual function, neuronal regeneration, blood pressure and heart rate, as well as the perception of pain, learning, attention and memory. The melanocortins also possess anti-inflammatory and anti-pyretic properties and control the secretion of several endocrine or exocrine glands such as the sebaceous, lacrymal, mammary glands, the prostate and the pancreas (Wikberg J. E. et al. *Pharmacol. Res.* 2000, 42, 393-420; Abdel-Malek Z. A., *Cell. Mol. Life. Sci.* 2001, 58, 434-441).

The effects of the melanocortins are mediated by a family of membrane receptors specific to seven transmembrane domains and coupled to the G proteins. Five sub-types of receptors, named MC1 to MC5, have been cloned and characterized to date. These receptors differ in their tissue distribution and by the affinity of the different melanocortins, the MC2 receptors only recognizing ACTH. The stimulation of the melanocortin receptors activates adenylate cyclase with production of cyclic AMP. If the specific functional roles of each of the receptors are not totally explained, the treatment of pathological disorders or diseases can be associated with an affinity for certain sub-types of receptors. Thus the activation of the MC1 receptors has been associated with the treatment of inflammations, since their blockage has been associated with the treatment of cutaneous cancers. The treatment of nutritional disorders has been associated with MC3 and MC4 receptors, the treatment of obesity with agonists and the treatment of cachexia and anorexia by antagonists. Other indications associated with the activation of MC3 and MC4 receptors are sexual activity disorders, neuropathic pain, anxiety, depression and drug addiction. The activation of MC5 receptors has been associated with the treatment of acne and dermatoses.

Research efforts have therefore focussed on the discovery of non-peptide compounds with a low molecular weight, bio-available by oral route, powerful agonists or antagonists of the melanocortin receptors.

The applicants have found that the novel compounds of general formula (I) described hereafter possess a good affinity for the melanocortin receptors. They act preferentially on MC4 receptors. Said compounds, agonists or antagonists of the melanocortin receptors, can be used for treating pathological states or metabolic diseases, of the nervous or dermatological system, in which one or more melanocortin receptors are involved such as the following examples: inflammatory states, disorders of energy homeostasis, food intake, weight disorders (obesity, cachexia, anorexia), sexual activity disorders (erective disorders), pain and more particularly neuropathic pain. There can also be mentioned mental disorders (anxiety, depression), drug addiction, skin diseases (acne, dermatoses, cutaneous cancers, melanomas). These compounds can also be used to stimulate nerve regeneration.

A subject of the invention is therefore a compound of general formula (I)

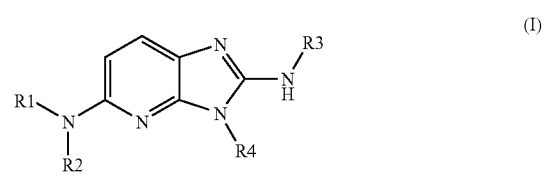

in racemic, enantiomeric form, or any combinations of these forms and in which:

$R_1$ and $R_2$ represent, independently, the hydrogen atom; a $(C_1\text{-}C_8)$alkyl radical optionally substituted by hydroxy; $(C_2\text{-}C_6)$alkenyl; a bicycloalkyl; or a radical of formula $-(CH_2)_n-X_1$ or $-X-(CH_2)_{n'}-X'_1$;

X represents $-C(O)-$ or $-C(S)-NH-$;

$X_1$ represents a $(C_1\text{-}C_6)$alkoxy, $(C_3\text{-}C_7)$cycloalkyl, adamantyl, heterocycloalkyl, aryl or heteroaryl radical, the $(C_3\text{-}C_7)$cycloalkyl, heterocycloalkyl, aryl and heteroaryl radicals being optionally substituted by one or more identical or different substituents chosen from: $-(CH_2)_{n1}-V_1-Y_1$, halo, nitro and cyano;

$V_1$ represents $-O-$, $-S-$ or a covalent bond;

$Y_1$ represents a $(C_1\text{-}C_6)$alkyl radical optionally substituted by one or more identical or different halo radicals, or aryl;

n and n' represent an integer from 0 to 6 and $n_1$ an integer from 0 to 2 (it being understood that when n is equal to 0, then $X_1$ does not represent the alkoxy radical);

$X'_1$ represents the hydrogen atom, a $(C_1\text{-}C_6)$alkyl radical optionally substituted by one or more identical or different halo radicals, $(C_3\text{-}C_7)$cycloalkyl; or aryl optionally substituted by one or more identical or different substituents chosen from: halo, nitro, cyano, $(C_1\text{-}C_6)$alkyl-carbonyl, $(C_1\text{-}C_6)$alkyl optionally substituted by one or more identical or different halo radicals, and $(C_1\text{-}C_6)$alkoxy optionally substituted by one or more identical or different halo radicals;

or $R_1$ and $R_2$ form together, with the nitrogen atom to which they are attached, a heterobicycloalkyl or a heterocycloalkyl optionally substituted by one or more identical or different substituents chosen from: hydroxy, $(C_1\text{-}C_6)$alkyl optionally substituted by hydroxy, $(C_1\text{-}C_6)$alkoxy-carbonyl, $-(CH_2)_{n''}-A$, $-C(O)-NV_1'Y_1'$, and heterocycloalkyl; or $R_1$ and $R_2$ form together a radical of formula:

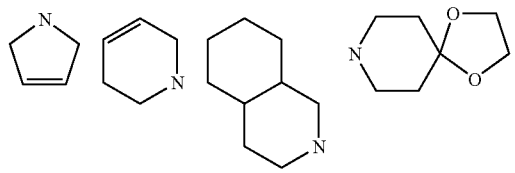

$V_1'$ and $Y_1'$ represent, independently, the hydrogen atom or a $(C_1\text{-}C_6)$alkyl;

A represents an aryl radical optionally substituted by one or more identical or different substituents chosen from: halo, nitro, cyano, $(C_1-C_6)$alkyl optionally substituted by one or more identical or different halo radicals, and $(C_1-C_6)$ alkoxy optionally substituted by one or more identical or different halo radicals;

n" represents an integer from 0 to 2;

$R_3$ represents $-Z_3$, $-C(R_{z3})(R'_{z3})-Z_3$, $-C(R_{z3})(R'_{z3})-(CH_2)_p-Z_3$ or $-C(O)-Z'_3$;

$R_{z3}$ and $R'_{z3}$ represent, independently, the hydrogen atom or a $(C_1-C_6)$alkyl radical;

$Z_3$ represents $Z_{3a}$, $Z_{3b}$, $Z_{3c}$, $Z_{3d}$, or $Z_{3e}$;

$Z_{3a}$ represents a $(C_1-C_6)$alkyl or $(C_2-C_6)$alkenyl radical;

$Z_{3b}$ represents a $(C_1-C_6)$alkoxy, $(C_1-C_6)$alkylthio, $(C_1-C_6)$alkylamino or di$((C_1-C_6)$alkyl)amino radical;

$Z_{3c}$ represents an aryl or heteroaryl radical;

the aryl and heteroaryl radicals being optionally substituted by one or more identical or different substituents chosen from: halo, cyano, nitro, azido, oxy or $-(CH_2)_{p'}-V_3-Y_3$;

$V_3$ represents $-O-$, $-S-$, $-C(O)-$, $-C(O)-O-$, $-O(CO)-$, $-SO_2-$, $-SO_2NH-$, $-NR'_3-SO_2-$, $-NR'_3-$, $-NR'_3-C(O)-$, $-C(O)-NR'_3-$, $-NH-C(O)-NR'_3-$ or a covalent bond;

$Y_3$ represents the hydrogen atom or a $(C_1-C_6)$alkyl radical optionally substituted by one or more identical or different halo radicals; an aryl radical optionally substituted by one or more identical or different substituents chosen from: halo, nitro, $(C_1-C_6)$alkyl and $(C_1-C_6)$alkoxy; or an aryl-$(C_1-C_6)$alkyl radical optionally substituted by one or more identical or different substituents chosen from: halo, nitro, $(C_1-C_6)$alkyl and $(C_1-C_6)$alkoxy;

$Z_{3d}$ represents a $(C_1-C_6)$alkoxy-carbonyl, amino-carbonyl, $(C_1-C_6)$alkylamino-carbonyl, di$((C_1-C_6)$alkyl)amino-carbonyl radical;

$Z_{3e}$ represents a $(C_1-C_6)$alkyl-C(O)-NH-, $(C_3-C_7)$cycloalkyl, heterocycloalkyl radical or a radical of formula

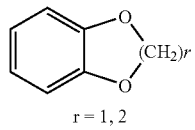 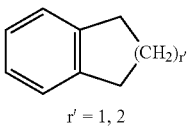

the $(C_3-C_7)$cycloalkyl and heterocycloalkyl radicals being optionally substituted by one or more identical or different oxy or $(C_1-C_6)$alkyl radicals, $Z'_3$ represents an aryl radical optionally substituted by one or more identical or different substituents chosen from: halo, nitro and $-(CH_2)_{p'}-V'_3-Y'_3$;

$V'_3$ represents $-O-$, $-C(O)-$, $-C(O)-O-$, $-C(O)-NR'_3-$, $-NR'_3-C(O)-$, $-NH-C(O)-NR'_3$ or a covalent bond;

$Y'_3$ represents the hydrogen atom or a $(C_1-C_6)$alkyl radical optionally substituted by one or more identical or different halo radicals;

$R'_3$ represents the hydrogen atom, a $(C_1-C_6)$alkyl or $(C_1-C_6)$alkoxy radical;

p, p' and p" represent, independently, an integer from 0 to 6;

$R_4$ represents a radical of formula $-(CH_2)_s-R'_4$ $R'_4$ represents a heterocycloalkyl containing at least one nitrogen atom and optionally substituted by $(C_1-C_6)$alkyl or aralkyl; a heteroaryl containing at least one nitrogen atom and optionally substituted by $(C_1-C_6)$alkyl; or a radical of formula $-NW_4W'_4$ $W_4$ represents the hydrogen atom or $(C_1-C_8)$alkyl;

$W'_4$ represents a radical of formula $-(CH_2)_{s'}-Z_4$;

$Z_4$ represents the hydrogen atom, $(C_1-C_8)$alkyl; $(C_2-C_6)$alkenyl; $(C_3-C_7)$cycloalkyl optionally substituted by one or more identical or different $(C_1-C_6)$alkyl substituents; cyclohexene; heteroaryl; aryl optionally substituted by one or more identical or different radicals chosen from: $-(CH_2)_{s''}-V_4-Y_4$, halo and nitro;

$V_4$ represents $-O-$, $-S-$, $-NH-C(O)-$, $-NV_4'-$ or a covalent bond;

$Y_4$ represents a hydrogen atom or a $(C_1-C_6)$alkyl radical optionally substituted by one or more identical or different halo radicals;

$V_4'$ represents a hydrogen atom or a $(C_1-C_6)$alkyl;

s" represents an integer from 0 to 4;

or $Z_4$ represents a radical of formula

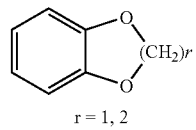

s and s' represent, independently, an integer from 0 to 6; or a pharmaceutically acceptable salt thereof.

In the definitions indicated above, the expression halo represents the fluoro, chloro, bromo or iodo radical, preferably chloro, fluoro or bromo. The expression alkyl (unless otherwise specified), preferably represents a linear or branched alkyl radical having 1 to 6 carbon atoms, such as the methyl, ethyl, propyl, isopropyl, butyl, isobutyl, sec-butyl and tert-butyl, pentyl or amyl, isopentyl, neopentyl, 2,2-dimethyl-propyl, hexyl, isohexyl or 1,2,2-trimethyl-propyl radicals. The term $(C_1-C_8)$alkyl designates a linear or branched alkyl radical having 1 to 8 carbon atoms, such as the radicals containing from 1 to 6 carbon atoms as defined above but also heptyl, octyl, 1,1,2,2-tetramethyl-propyl, 1,1,3,3-tetramethyl-butyl. By the expression alkyl substituted by hydroxy, is meant any linear or branched alkyl chain, containing a hydroxy radical positioned along the chain; thus for a chain containing 3 carbon atoms and a hydroxy radical, there can be given as examples $HO-(CH_2)_3-$, $CH_3-CH(OH)-CH_2-$ and $CH_3-CH_2-CH(OH)-$.

By alkenyl, unless otherwise specified, is meant a linear or branched alkyl radical containing 1 to 6 carbon atoms and having at least one unsaturation (double bond), such as for example vinyl, allyl, propenyl, butenyl or pentenyl.

The term alkoxy designates the radicals in which the alkyl radical is as defined above such as for example the methoxy, ethoxy, propyloxy or isopropyloxy radicals but also linear, secondary or tertiary butoxy, pentyloxy. The term alkoxy-carbonyl preferably designates the radicals in which the alkoxy radical is as defined above such as for example methoxycarbonyl, ethoxycarbonyl.

The term $(C_3-C_7)$cycloalkyl designates a saturated carbon monocyclic system comprising 3 to 7 carbon atoms, and preferably the cyclopropyl, cyclobutyl, cyclopentyl, cyclohexyl or cycloheptyl rings. The expression heterocycloalkyl designates a condensed monocyclic or bicyclic saturated system containing from 2 to 9 carbon atoms and at least one heteroatom. This radical can contain several identical or different heteroatoms. Preferably, the heteroatoms are chosen from oxygen, sulphur or nitrogen. As an example of a heterocycloalkyl, there can be mentioned the rings containing at least one nitrogen atom such as pyrrolidine, imidazolidine, pyrrazolidine, isothiazolidine, thiazolidine, isoxazolidine, oxazolidine, piperidine, piperazine, azepane (azacycloheptane), azacyclooctane, diazepane, morpholine, decahydroisoquinoline (or decahydroquinoline) but also the rings containing no nitrogen atom such as tetrahydrofuran or tetrahydrothiophene. As an illustration of a cycloalkyl or heterocycloalkyl substituted by oxy, there can be mentioned for example pyrrolidinone and imidazolidinone.

The term bicycloalkyl designates a non-condensed saturated hydrocarbon bicyclic system containing 5 to 9 carbon atoms, such as bicyclo-heptane such as for example bicylo[2,2,1]heptane, or bicyclo-octane such as for example bicyclo[2,2,2]octane or bicyclo[3,2,1]octane. The term heterobicycloalkyl designates a non-condensed saturated hydrocarbon bicyclic system containing 5 to 8 carbon atoms and at least one heteroatom chosen from nitrogen, oxygen and sulphur. As examples of a heterobicycloalkyl, there can be mentioned aza-bicycloheptane and aza-bicyclooctane such as 7-aza-bicyclo[2,2,1]heptane, 2-aza-bicyclo[2,2,2]octane or 6-aza-bicyclo[3,2,1]octane.

The expression aryl represents an aromatic radical, constituted by a ring or condensed rings, such as for example the phenyl, naphthyl, fluorenyl or anthryl radical. The expression heteroaryl designates an aromatic radical, constituted by a ring or condensed rings, with at least one ring containing one or more identical or different heteroatoms chosen from sulphur, nitrogen or oxygen. As examples of a heteroaryl radical, there can be mentioned the radicals containing at least one nitrogen atom such as pyrrolyl, imidazolyl, pyrazolyl, isothiazolyl, thiazolyl, isoxazolyl, oxazolyl, triazolyl, thiadiazolyl, pyridyl, pyrazinyl, pyrimidyl, quinolyl, isoquinolyl, quinoxalinyl, indolyl, dihydroindolyl, benzoxadiazoyl, carbazolyl, phenoxazinyl but also the radicals containing no nitrogen atom such as thienyl, benzothienyl, furyl, benzofuryl, dibenzofuryl, dihydrobenzofuryl, dibenzothienyl, thioxanthenyl, or pyranyl. The term aralkyl (arylalkyl) preferably designates the radicals in which the aryl and alkyl radicals are as defined above such as for example benzyl or phenethyl. As illustrations of an aryl or heteroaryl radical substituted by oxy, there can be mentioned for example fluorenone, acridone, xanthenone, benzothienyl-dione, anthraquinone, thioxanthene, benzocoumarin.

In the present Application also, the $(CH_2)_i$ radical (i being an integer which can represent n, n', n", $n_1$, p, p', p", s, s' and s" as defined above), represents a linear or branched hydrocarbon chain with i carbon atoms. Thus the $—(CH_2)_3—$ radical can represent $—CH_2—CH_2—CH_2—$ but also $—CH(CH_3)—CH_2—$, $—CH_2—CH(CH_3)—$ or $—C(CH_3)_2—$.

According to the present Application also, when a radical has the formula —B-D-E with D representing for example —C(O)—NH—, this means that the carbon atom of —C(O)—NH— is bound to B and the nitrogen atom to E.

Preferably, the invention relates to a compound of formula I as defined above, characterized in that $R_1$ and $R_2$ represent, independently, the hydrogen atom, a $(C_1-C_8)$alkyl radical, a bicycloalkyl or a radical of formula $—(CH_2)_n—X_1$ or $—X—(CH_2)_{n'}—X'_1$;

X represents —C(O)— or —C(S)—NH—;

$X_1$ represents a $(C_1-C_6)$alkoxy, $(C_3-C_7)$cycloalkyl radical optionally substituted by a $(C_1-C_6)$alkyl, or heteroaryl;

$X'_1$ represents the hydrogen atom, a $(C_1-C_6)$alkyl radical optionally substituted by one or more identical or different halo radicals, $(C_3-C_7)$cycloalkyl or aryl optionally substituted by a $(C_1-C_6)$alkyl-carbonyl;

or $R_1$ and $R_2$ form together, with the nitrogen atom to which they are attached, a heterobicycloalkyl or a heterocycloalkyl optionally substituted by one or more identical or different substituents chosen from: $(C_1-C_6)$alkyl, $(C_1-C_6)$alkoxy-carbonyl and $—(CH_2)_{n''}-A$;

A represents an aryl radical optionally substituted by one or more identical or different substituents chosen from: halo and $(C_1-C_6)$alkyl;

n" represents an integer from 0 to 1;

$R_4$ represents a radical of formula $—(CH_2)_s—R'_4$ $R'_4$ represents a heterocycloalkyl containing at least one nitrogen atom and optionally substituted by $(C_1-C_6)$alkyl; or a radical of formula $—NW_4W'_4$ $W_4$ represents the hydrogen atom or $(C_1-C_8)$alkyl;

$W'_4$ represents a radical of formula $—(CH_2)_{s'}-Z_4$;

$Z_4$ represents the hydrogen atom, $(C_1-C_8)$alkyl or aryl optionally substituted by one or more identical or different radicals chosen from: $—(CH_2)_{s''}—V_4—Y_4$;

$V_4$ represents —O—;

$Y_4$ represents a $(C_1-C_6)$alkyl radical optionally substituted by one or more identical or different halo radicals;

s" represents an integer from 0 to 4;

s and s' represent, independently, an integer from 1 to 4; or a salt; or a pharmaceutically acceptable salt thereof, and more particularly compound I comprises at least one of the following characteristics:

the cycloalkyl radical is chosen from cyclopropyl, cyclobutyl and cyclohexyl;

the bicycloalkyl radical is bicylo[2,2,1]heptane;

the heterobicycloalkyl is 7-aza-bicyclo[2,2,1]heptane;

the aryl radical is the phenyl radical;

the heteroaryl radical is the furyl radical;

the heterocycloalkyl is chosen from piperidine, morpholine and piperazine; or a pharmaceutically acceptable salt thereof.

Very preferentially also, the invention relates to a compound of formula I as defined above, characterized in that $R_1$ and $R_2$ represent, independently, the hydrogen atom, a $(C_1-C_8)$alkyl radical or a radical of formula $—(CH_2)_n—X_1$ or $—X—(CH_2)_{n'}—X'_1$;

X represents —C(O)—;

$X_1$ represents a $(C_3-C_7)$cycloalkyl radical;

$X'_1$ represents the hydrogen atom or a $(C_3-C_7)$cycloalkyl radical;

n represents 0 or 1; n' represents an integer from 0 to 5;

or $R_1$ and $R_2$ form together, with the nitrogen atom to which they are attached, a heterocycloalkyl optionally substituted by one or more identical or different $(C_1-C_6)$alkyl substituents;

and more particularly the $(C_3-C_7)$cycloalkyl radical represented by $X_1$ and $X'_1$ is chosen from cyclopropyl, cyclobutyl and cyclohexyl; and the heterocycloalkyl that $R_1$ and $R_2$ form together, is the piperidine ring; or a pharmaceutically acceptable salt thereof.

Very preferentially also, the invention relates to a compound of formula I as defined above, characterized in that $R_4$ represents a radical of formula $—(CH_2)_s—R'_4$ $R'_4$ represents a heterocycloalkyl containing at least one nitrogen atom and optionally substituted by $(C_1-C_6)$alkyl; or a radical of formula $—NW_4W'_4$ $W_4$ represents the hydrogen atom or $(C_1-C_8)$alkyl;

$W'_4$ represents a radical of formula $—(CH_2)_{s'}-Z_4$;

$Z_4$ represents the hydrogen atom or $(C_1-C_8)$alkyl;

s and s' represent, independently, an integer from 2 to 4;

and more particularly the heterocycloalkyl represented by $R'_4$ is chosen from: piperidine and morpholine; or a pharmaceutically acceptable salt thereof.

Preferably also, the invention relates to a compound of formula I as defined above, characterized in that $R_3$ represents —C(O)-Z'$_3$ Z'$_3$ represents an aryl radical optionally substituted by one or more identical or different substituents chosen from halo and —(CH$_2$)$_{p''}$—V'$_3$—Y'$_3$;

V'$_3$ represents —O— or a covalent bond;

Y'$_3$ represents the hydrogen atom or a (C$_1$-C$_6$)alkyl radical optionally substituted by one or more identical or different halo radicals;

p" represents an integer from 0 to 2; or a pharmaceutically acceptable salt thereof.

Preferably also, the invention relates to a compound of formula I as defined above, characterized in that $R_3$ represents -Z$_3$, —C(R$_{z3}$)(R'$_{z3}$)-Z$_3$ or —C(R$_{z3}$)(R'$_{z3}$)—(CH$_2$)$_p$-Z$_3$; or a pharmaceutically acceptable salt thereof.

Very preferentially also, the invention relates to a compound of formula I as defined above, characterized in that $R_3$ represents -Z$_3$ and Z$_3$ represents Z$_{3b}$, Z$_{3c}$ or Z$_{3e}$; and preferably Z$_3$ represents Z$_{3c}$ and Z$_{3c}$ represents an aryl radical, and more particularly Z$_{3c}$ represents a phenyl radical being optionally substituted by one or more identical or different substituents chosen from: halo, nitro or —(CH$_2$)$_p$—V$_3$—Y$_3$;

V$_3$ represents —O—, —S—, —C(O)—, —C(O)—O—, —SO$_2$NH—, —NR'$_3$—C(O)—, —C(O)—NR'$_3$— or a covalent bond;

R'$_3$ represents the hydrogen atom;

Y$_3$ represents the hydrogen atom or a (C$_1$-C$_6$)alkyl radical optionally substituted by one or more identical or different halo radicals;

and more particularly also Z$_{3c}$ represents a phenyl radical substituted by one or more identical or different substituents of formula —(CH$_2$)$_p$—V$_3$—Y$_3$;

V$_3$ represents —C(O)—, —C(O)—O— or —C(O)—NR'$_3$—;

R'$_3$ represents the hydrogen atom;

Y$_3$ represents the hydrogen atom or a (C$_1$-C$_6$)alkyl radical; or a pharmaceutically acceptable salt thereof.

Very preferably also, the invention relates to compounds of formula I as defined above, characterized in that $R_3$ represents —C(R$_{z3}$)(R'$_{z3}$)-Z$_3$ and Z$_3$ represents Z$_{3d}$ or Z$_{3e}$; or a pharmaceutically acceptable salt thereof.

Very preferentially also, the invention relates to compounds of formula I as defined above, characterized in that $R_3$ represents —C(R$_{z3}$)(R'$_{z3}$)—(CH$_2$)$_p$-Z$_3$ and Z$_3$ represents Z$_{3c}$, Z$_{3d}$ or Z$_{3e}$, and more particularly Z$_3$ represents Z$_{3d}$ or Z$_{3e}$ Z$_{3d}$ represents a (C$_1$-C$_6$)alkoxy-carbonyl or amino-carbonyl radical;

Z$_{3e}$ represents a (C$_1$-C$_6$)alkyl-C(O)—NH—, heterocycloalkyl radical being optionally substituted by an oxy radical, or a radical of formula

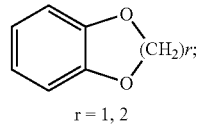

r = 1, 2 or a pharmaceutically acceptable salt thereof.

In the present Application, the symbol ->* corresponds to the attachment point of the radical. When the attachment site is not specified on the radical, this means that the attachment is carried out on one of the available sites of this radical for such an attachment.

According to the definitions of the variable groups $R_1$, $R_2$, $R_3$ and $R_4$, the compounds according to the invention can be prepared in liquid phase according to the different procedures A to E described below.

A. Preparation According to Reaction Diagram A:

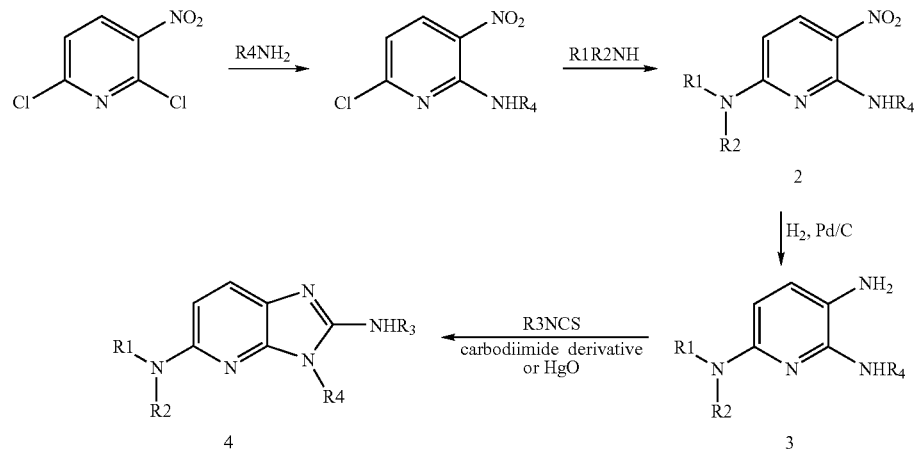

As described in diagram A, 2,6-dichloro-3-nitropyridine can be treated with a primary amine in the presence of an organic base such as a tertiary amine or an inorganic base such as potassium or caesium carbonate, in an apolar aprotic solvent such as toluene at a temperature of approximately 20° C. for 3-18 hours in order to produce compound (1). The chlorinated derivative (1) can react with a primary or secondary amine, in the presence of an organic base such as a tertiary amine or an inorganic base such as potassium or caesium carbonate, in a polar aprotic solvent such as acetonitrile, dimethylformamide or HMPA at a temperature of 20-70° C. for 2-18 hours in order to produce compound (2). The nitro function of compound (2) is reduced by catalytic hydrogenation in the presence of 10% palladium on carbon in an inert solvent such as methanol, ethanol, ethyl acetate or a mixture of these solvents, at a temperature of 18-25° C., for 2 to 8 hours in order to produce the dianiline (3). Derivative (3) is then treated with an isothiocyanate in the presence of a coupling agent supported or not supported on a resin such as diisopropylcarbodiimide- or dicyclohexylcarbodiimide or N-cyclohexylcarbodiimide N-methyl polystyrene resin in an inert solvent such as tetrahydrofuran, methylene chloride, or chloroform at a temperature of 20-70° C. for 2 to 72 hours in order to produce derivative (4). Alternatively, derivative (3) can be treated with an isothiocyanate in an inert solvent such as tetrahydrofuran, methylene chloride, chloroform or ethanol at a temperature of 20-80° C. for 1-16 hours then the resultant thiourea can be treated with yellow mercury(II) oxide in the presence of a catalytic quantity of sulphur in a polar solvent such as methanol or ethanol for 2 to 24 hours at a temperature of 20-80° C. in order to produce (4).

EXAMPLE A1

4-{[3-(3-aminopropyl)-5-(diisobutylamino)-3H-imidazo[4,5-b]pyridin-2-yl]amino}-N-methylbenzamide hydrochloride

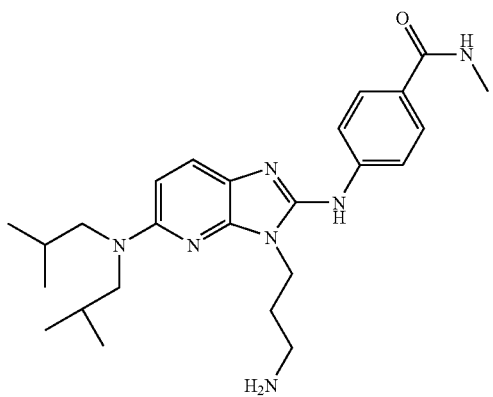

Stage 1: tert-butyl 3-[(6-chloro-3-nitropyridin-2-yl)amino]propyl carbamate

Potassium carbonate (5.4 g, 1.2 eq) and tert-butyl-N(2-aminopropyl)carbamate (6.8 g, 1 eq) are added successively to 2,6-dichloro-3-nitropyridine (8 g, 1 eq) in solution in toluene (150 ml). After stirring for 6 hours at a temperature of approximately 20° C., the mixture is concentrated under reduced pressure at 40° C. then water (80 ml) and dichloromethane (200 ml) are added. After decantation and extractions, the combined organic phases are washed with salt water, dried over $Na_2SO_4$ then concentrated under reduced pressure at 40° C. Purification of the solid obtained, by flash chromatography on silica gel (eluent: heptane/ethyl acetate 7:3), produces the expected compound in the form of a yellow solid (11.4 g; 92% yield).

MS/LC: calculated MM=330.7; m/z=331.1 (MH+) NMR ($^1$H, 400 MHz, DMSO-$d_6$): δ 1.36 (s, 9H), 1.68 (m, 2H), 2.99 (dd, 2H), 3.51 (dd, 2H), 6.76 (d, 1H), 6.86 (t, 1H), 8.41 (d, 1H), 8.75 (t, 1H).

Stage 2: tert-butyl 3-{[6-(diisobutylamino)-3-nitropyridin-2-yl]amino}propyl carbamate Potassium carbonate (1.31 g, 1.5 eq) and diisobutylamine (981 mg, 1.2 eq) are added successively to a solution of tert-butyl 3-[(6-chloro-3-nitropyridin-2-yl)amino]propyl carbamate (2 g, 1 eq) in acetonitrile (100 ml). The mixture is heated to reflux for 5 hours then cooled down to ambient temperature and concentrated under reduced pressure at 40° C. The residue is taken up in dichloromethane (200 ml) and water (90 ml). After decantation and extractions, the combined organic phases are washed with salt water, dried over $Na_2SO_4$ then concentrated under reduced pressure at 40° C. Purification of the residue obtained, by flash chromatography on silica gel (eluent: heptane/ethyl acetate 7:3 to 1:1), produces the expected compound in the form of a yellow oil (2.46 g; 95% yield).

MS/LC: calculated MM=437.6; m/z=438.3 (MH+) NMR ($^1$H, 400 MHz, DMSO-$d_6$): δ 0.86 (m, 12H), 1.36 (s, 9H), 1.68 (m, 2H), 1.99 (m, 1H), 2.15 (m, 1H), 2.98 (dd, 2H), 3.35 (m, 2H), 3.48 (m, 4H), 6.20 (d, 1H), 6.85 (t, 1H), 8.01 (d, 1H), 8.85 (t, 1H).

Stage 3: tert-butyl 3-[5-(diisobutylamino)-2-({4-[(methylamino)carbonyl]phenyl}amino)-3H-imidazo[4,5-b]pyridin-3-yl]propyl carbamate Tert-butyl 3-{[6-(diisobutylamino)-3-nitropyridin-2-yl]amino}propyl carbamate (63 mg) in solution in a mixture of ethyl acetate/ethanol 3:1 (1.5 ml), and 10% palladium on carbon (7 mg) are added to a hemolysis tube placed in an autoclave. After stirring for 3 hours under a hydrogen atmosphere (3 bar) at a temperature of approximately 20° C., the mixture is filtered on celite in a hemolysis tube containing a solution of 4-isothiocyanato-N-methylbenzamide (43 mg, 1.2 eq) in tetrahydrofuran (1 ml). N-cyclohexylcarbodiimide-N-methyl-polystyrene resin (acquired from Novabiochem; load 1.9 mmol/g; 237 mg, 3 eq) is added to the filtrate thus obtained. The mixture is heated to reflux for 18 hours, cooled down to ambient temperature then filtered on frit and the filtrate is concentrated under reduced pressure at 40° C. Purification of the residue by flash chromatography on silica gel (eluent: heptane/ethyl acetate 1:1 to 100% ethyl acetate) produces the expected compound (53 mg; 65% yield).

MS/LC: calculated MM=551.7; m/z=552.3 (MH+) NMR ($^1$H, 400 MHz, DMSO-$d_6$): δ 0.88 (d, 12H), 1.36 (s, 9H), 1.83 (m, 2H), 2.09 (m, 2H), 2.76 (d, 3H), 2.98 (m, 2H), 3.35 (m, 4H), 4.15 (t, 2H), 6.34 (d, 1H), 6.80 (t, 1H), 7.51 (d, 1H), 7.78 (AB, 2H), 7.85 (AB, 2H), 8.20 (m, 1H), 8.97 (s, 1H).

Stage 4: 4-{[3-(3-aminopropyl)-5-(diisobutylamino)-3H-imidazo[4,5-b]pyridin-2-yl]amino}-N-methylbenzamide hydrochloride A solution of hydrochloric acid in ether (1N, 2 ml) is added to a solution of tert-butyl 3-[5-(diisobutylamino)-2-({4-[(methylamino)carbonyl]phenyl}amino)-3H-imidazo[4,5-b]pyridin-3-yl]propyl carbamate (51 mg) in ethyl acetate (0.5 ml). After stirring for 2 hours at a temperature of approximately 20° C., the mixture is filtered and the solid obtained is washed with ethyl ether and dried (50 mg; 95% yield).

MS/LC: calculated MM=451.6; m/z=452.3 (MH+) NMR ($^1$H, 400 MHz, DMSO-$d_6$): δ 0.88 (d, 12H), 2.10-2.19 (m, 4H), 2.79 (d, 3H), 2.95 (m, 2H), 3.35 (m, 4H), 4.40 (t, 2H), 6.55 (d, 1H), 7.53 (d, 1H), 7.64 (m, 2H), 7.94 (m, 5H), 8.45 (m, 2H).

EXAMPLE A2

1-(4-{[5-(dibutylamino)-3-(3-piperidin-1-ylpropyl)-3H-imidazo[4,5-b]pyridin-2-yl]amino}phenyl)ethanone hydrochloride

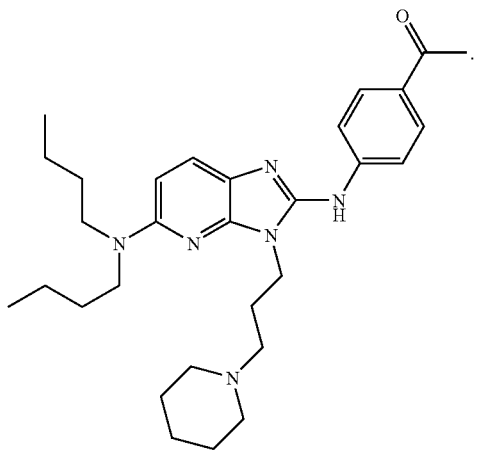

Stage 1: 6-chloro-3-nitro-N-(3-piperidin-1-ylpropyl)pyridin-2-amine

Potassium carbonate (540 mg, 1.5 eq) and 3-piperidinopropylamine (420 mg, 1 eq) are added successively to 2,6-dichloro-3-nitropyridine (500 mg, 1 eq) in solution in toluene (10 ml). After stirring for 2 hours at a temperature of approximately 20° C., the mixture is concentrated under reduced pressure at 40° C. then water (20 ml) and dichloromethane (70 ml) are added. After decantation and extractions, the combined organic phases are washed with salt water, dried over $Na_2SO_4$ then concentrated under reduced pressure at 40° C. Purification of the solid obtained, by flash chromatography on silica gel (eluent: heptane/ethyl acetate 3:7 to 100% ethyl acetate), produces the expected compound in the form of a yellow solid (473 mg; 61% yield).

MS/LC: calculated MM=298.8; m/z=299.1 (MH+) NMR ($^1$H, 400 MHz, DMSO-$d_6$): δ 1.37 (m, 2H), 1.49 (m, 4H), 1.74 (m, 2H), 2.34 (m, 6H), 3.55 (m, 2H), 6.75 (d, 1H), 8.40 (d, 1H), 8.96 (t, 1H).

Stage 2: $N^6,N^6$-dibutyl-3-nitro-$N^2$-(3-piperidin-1-ylpropyl)pyridine-2,6-diamine Potassium carbonate (54 mg, 2 eq) and a solution of dibutylamine (30 mg, 1.2 eq) in acetonitrile (2 ml) are added successively to a solution of 6-chloro-3-nitro-N-(3-piperidin-1-ylpropyl)pyridin-2-amine (59 mg, 1 eq) in acetonitrile (3 ml). The mixture is heated to reflux for 15 hours then cooled down to ambient temperature and concentrated under reduced pressure at 40° C. The residue is taken up in dichloromethane (200 ml) and water (90 ml). After decantation and extractions, the combined organic phases are washed with salt water, dried over $Na_2SO_4$ then concentrated under reduced pressure at 40° C. Purification of the residue obtained, by flash chromatography on silica gel (eluent: heptane/ethyl acetate 1:1 to 100% ethyl acetate), produces the expected compound (73 mg; 95% yield).

MS/LC: calculated MM=391.6; m/z=392.2 (MH+)

Stage 3: 1-(4-{[5-(dibutylamino)-3-(3-piperidin-1-ylpropyl)-3H-imidazo[4,5-b]pyridin-2-yl]amino}phenyl)ethanone hydrochloride $N^6,N^6$-dibutyl-3-nitro-$N^2$-(3-piperidin-1-ylpropyl)pyridine-2,6-diamine (70 mg) in solution in a mixture of ethyl acetate/methanol 3:1 (2 ml), and 10% palladium on carbon (7 mg) are introduced into a hemolysis tube placed in an autoclave. After stirring for 3 hours under a hydrogen atmosphere (3 bar) at a temperature of approximately 20° C., the mixture is filtered on celite in a hemolysis tube containing a solution of 4-isothiocyanato-N-methylbenzamide (43 mg, 1.2 eq) in tetrahydrofuran (1 ml).

N-cyclohexylcarbodiimide-N-methyl-polystyrene resin (acquired from Novabiochem; load 1.9 mmol/g; 284 mg, 3 eq) is added to the filtrate thus obtained. The mixture is heated to reflux for 18 hours, cooled down to ambient temperature then filtered on frit and the filtrate is concentrated under reduced pressure at 40° C. Purification of the residue by flash chromatography on silica gel (eluent: 100% dichloromethane to dichloromethane/methanol 9:1) produces the expected compound in the form of a base. The corresponding hydrochloride salt is formed by adding a 1N hydrochloric acid solution in ethyl ether. The precipitate obtained is filtered and dried in order to produce the expected compound (72 mg).

MS/LC: calculated MM=504.7; m/z=505.2 (MH+) NMR ($^1$H, 400 MHz, DMSO-$d_6$): δ 0.92 (t, 6H), 1.34 (m, 5H), 1.55 (m, 4H), 1.77 (m, 5H), 2.35 (m, 2H), 2.59 (s, 3H), 2.88 (m, 2H), 3.18 (m, 2H), 3.38 (m, 2H), 3.49 (m, 4H), 4.48 (t, 2H), 6.60 (m, 1H), 7.59 (d, 1H), 7.70 (d, 2H), 8.06 (m, 2H), 10.62 (s, 1H), 11.71 (s, 1H).

Preparation of Non-Commercial Isothiocyanates:

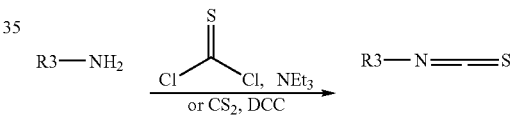

A primary amine can be converted to isothiocyanate, by treatment with thiophosgene in the presence of a tertiary base such as triethylamine, in an aprotic solvent such as dichloromethane or tetrahydrofuran, at a temperature of 0-20° C. for 0.3 to 2 hours, or alternatively by treatment with carbon disulphide and cyclohexylcarbodiimide supported or not supported on a resin in an aprotic solvent such as dichloromethane or tetrahydrofuran, at a temperature of 0-70° C. for 0.3 to 15 hours.

Preparation of 4-isothiocyanato-N-methylbenzamide:

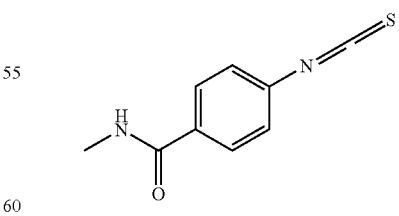

Thiophosgene (1.13 ml, 1.1 eq) is added dropwise to a solution cooled down to 0° C., of 4-amino-N-methylbenzamide (2 g, 1 eq) and triethylamine (5.6 ml, 3 eq) in tetrahydrofuran (260 ml). The mixture is stirred for 30 minutes at 0° C. then the cold bath is removed and stirring is continued for another 30 minutes. Water (100 ml) and diethyl ether (250 ml)

are added to the mixture. After decantation and extractions, the organic phases are combined, washed with salt water, dried over Na$_2$SO$_4$ then concentrated under reduced pressure at 40° C. The solid obtained is recrystallized from a dichloromethane/petroleum ether mixture (2.2 g; 86% yield).

NMR ($^1$H, 400 MHz, DMSO-d$_6$): δ 2.77 (d, 3H), 7.51 (AB, 2H), 7.88 (AB, 2H), 8.52 (m, 1H).

According to the same procedure as that described for N-(4-isothiocyanatophenyl)acetamide, the following isothiocyanates can be prepared:

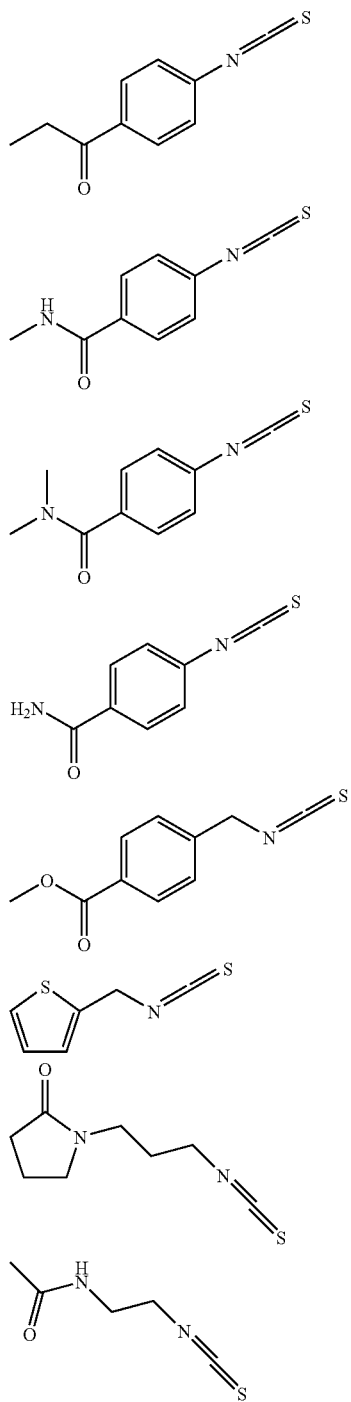

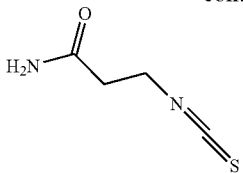

Preparation of N-(4-isothiocyanatophenyl)-N'-methoxyurea:

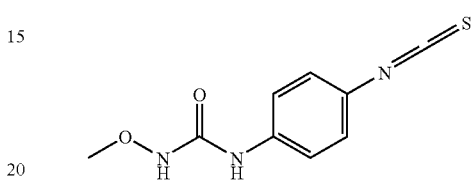

Carbonyldiimidazole (CDI) (1.62 g, 2 eq) is added to a solution cooled down to 0° C. of tert-butyl 4-aminophenyl carbamate (1.04 g) in anhydrous dichloromethane (100 ml). The mixture is taken to a temperature of 20° C. and stirred at this temperature for 15 hours. Triethylamine (7 ml, 10 eq) followed by O-methylhydroxylamine hydrochloride (4.2 g, 10 eq) are added successively to the reaction medium cooled down to 0° C. After stirring for 3 hours at a temperature of approximately 20° C., water saturated in sodium hydrogen carbonate and chloroform is added to the mixture. After decantation and extractions, the combined organic phases are washed with salt water, dried over Na$_2$SO$_4$ then concentrated under reduced pressure at 40° C. in order to produce tert-butyl 4-{[(methoxyamino)carbonyl]amino}phenyl carbamate (1.33 g). A flow of gaseous hydrochloric acid is passed through a suspension of this derivative in ethyl acetate until the reaction is complete. The precipitate obtained is filtered then washed with diethyl ether and dried in order to produce N-(4-aminophenyl)-N'-methoxyurea hydrochloride (1 g).

Thiophosgene (0.38 ml, 1.1 eq) is added dropwise to a solution cooled down to 0° C., of N-(4-aminophenyl)-N'-methoxyurea hydrochloride (1 g) and triethylamine (3.2 ml, 5 eq) in tetrahydrofuran (90 ml). The mixture is stirred for 15 minutes at 0° C. then water and diethyl ether are added. After decantation and extractions, the organic phases are combined, washed with salt water, dried over Na$_2$SO$_4$ then concentrated under reduced pressure at 40° C. Purification by flash chromatography on silica gel (eluent: heptane/ethyl acetate 7:3 to 3:7) produces the expected compound (630 mg; 62% yield).

NMR ($^1$H, 400 MHz, DMSO-d$_6$): δ 3.61 (s, 3H), 7.34 (AB, 2H), 7.67 (AB, 2H), 9.11 (s, 1H), 9.65 (s, 1H).

Preparation of Non-Commercial Acyl-isothiocyanates:

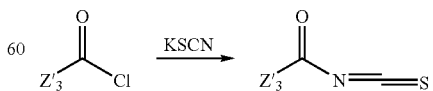

Acyl-isothiocyanates can be prepared from the corresponding acid chlorides by treatment with potassium thiocyanate in an aprotic solvent such as acetonitrile at a temperature of 0-60° C. for 0.2-5 hours.

Methyl-4-isothiocyanatocarbonylbenzoate:

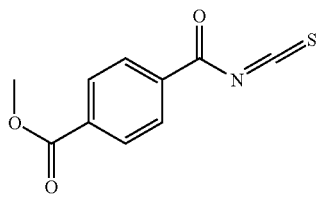

Potassium thiocyanate (1.08 g, 1.1 eq) is added to a solution of methyl-4-chlorocarbonylbenzoate (2 g) in acetonitrile (30 ml). After stirring for 1 hour at approximately 20° C., the mixture is filtered and the filtrate is concentrated under reduced pressure at 40° C. The solid obtained is purified by flash chromatography on silica gel (eluent: heptane/ethyl acetate 1:1) in order to produce the expected compound (2.1 g; 95% yield).

NMR ($^1$H, 400 MHz, DMSO-$d_6$): δ 3.88 (s, 3H), 8.0 (m, 4H).

According to the same procedure as that described for methyl-4-isothiocyanatocarbonylbenzoate, the following isothiocyanates can be prepared:

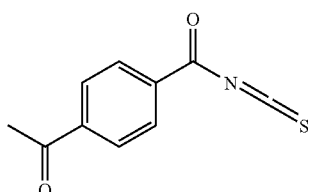

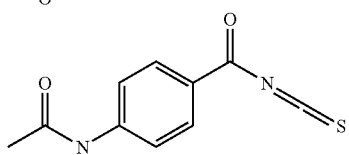

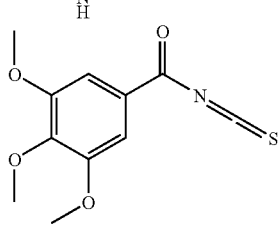

According to reaction diagram A and in a manner analogous to the procedure described for the synthesis of 4-{[3-(3-aminopropyl)-5-(diisobutylamino)-3H-imidazo[4,5-b]pyridin-2-yl]amino}-N-methylbenzamide hydrochloride or 1-(4-{[5-(dibutylamino)-3-(3-piperidin-1-ylpropyl)-3H-imidazo[4,5-b]pyridin-2-yl]amino}phenyl)ethanone hydrochloride, the following compounds can be prepared:

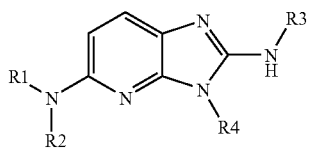

in which $R_1R_2N$ represents one of the radicals below:

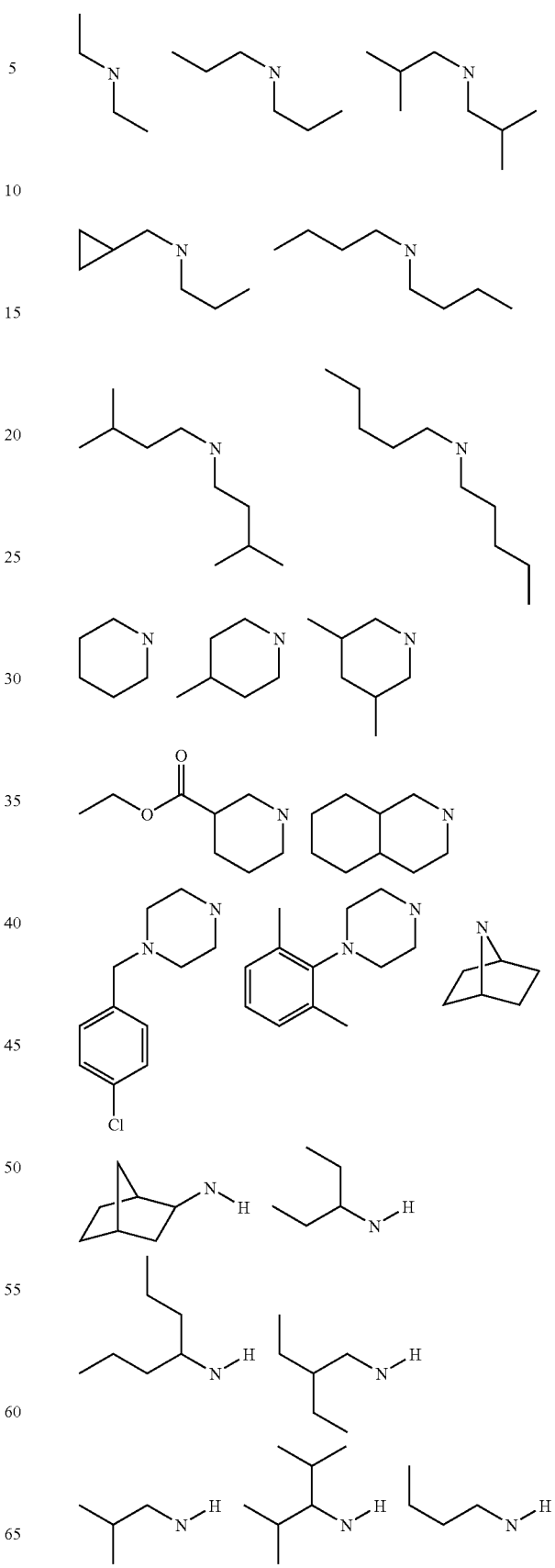

-continued
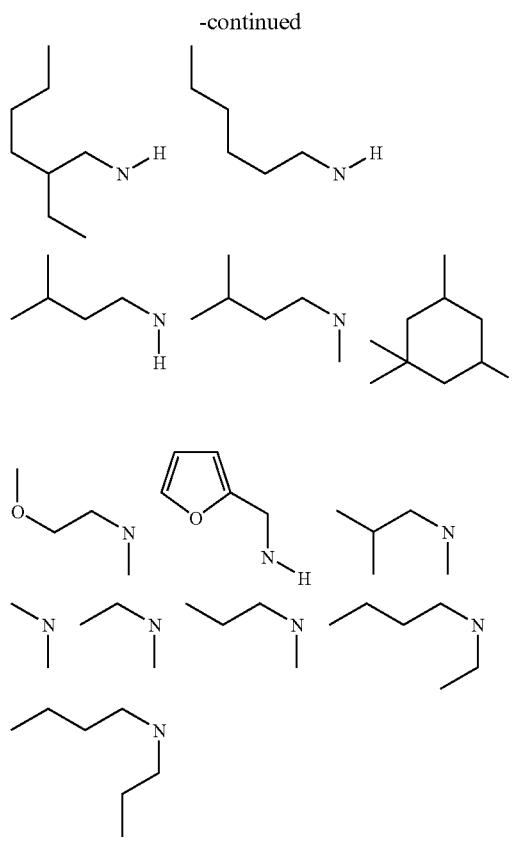
$R_3$ represents one of the radicals below:
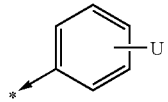
1 or more substitutions chosen from:
U=H, F, Cl, Br, I, $NO_2$, OMe, SMe, Me, Et, iPr, tBu, $CF_3$, $OCF_3$, C(O)OMe, C(O)OEt, C(O)Me, C(O)Et, NHC(O)Me, C(O)NHMe, C(O)$NH_2$, S(O)$_2$$NH_2$, NHC(O)NHMe, NHC(O)NHOMe
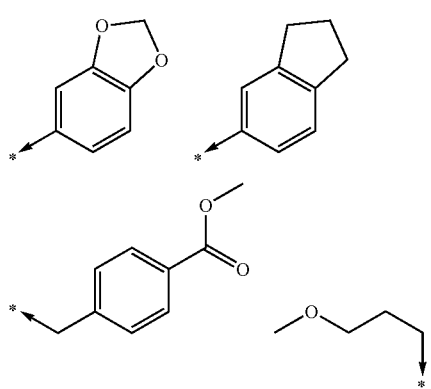
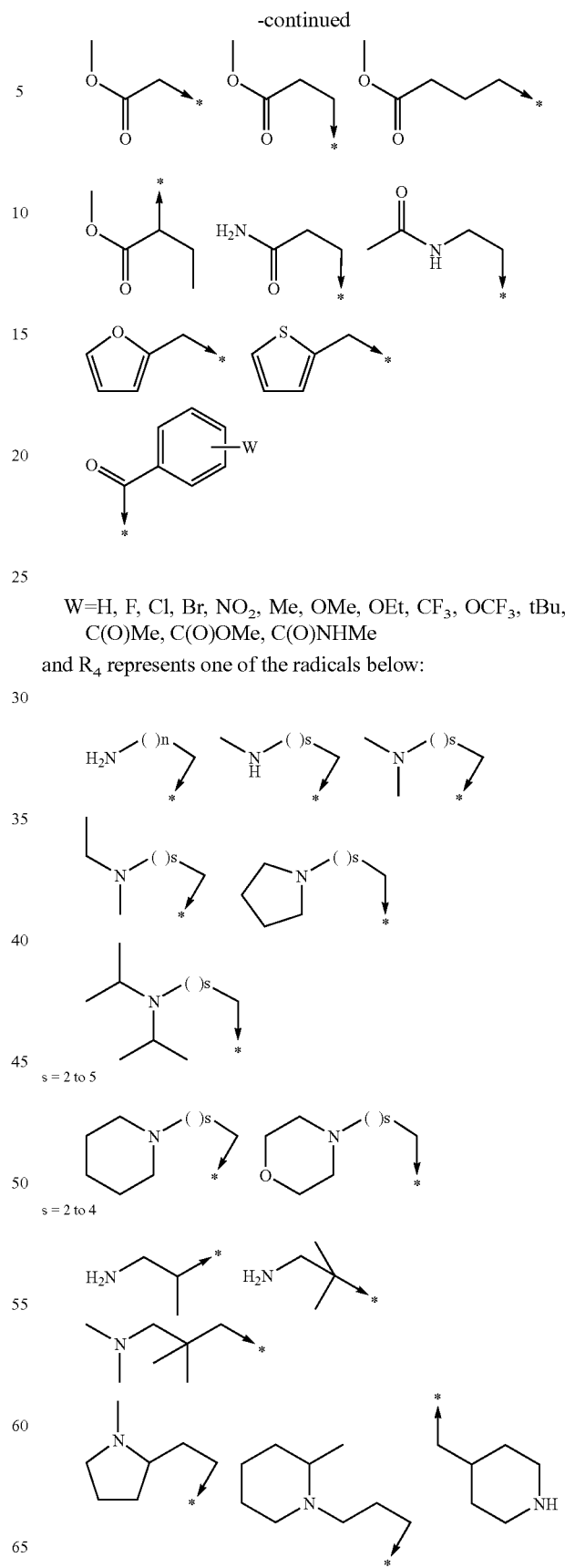
W=H, F, Cl, Br, $NO_2$, Me, OMe, OEt, $CF_3$, $OCF_3$, tBu, C(O)Me, C(O)OMe, C(O)NHMe
and $R_4$ represents one of the radicals below:
s = 2 to 5
s = 2 to 4

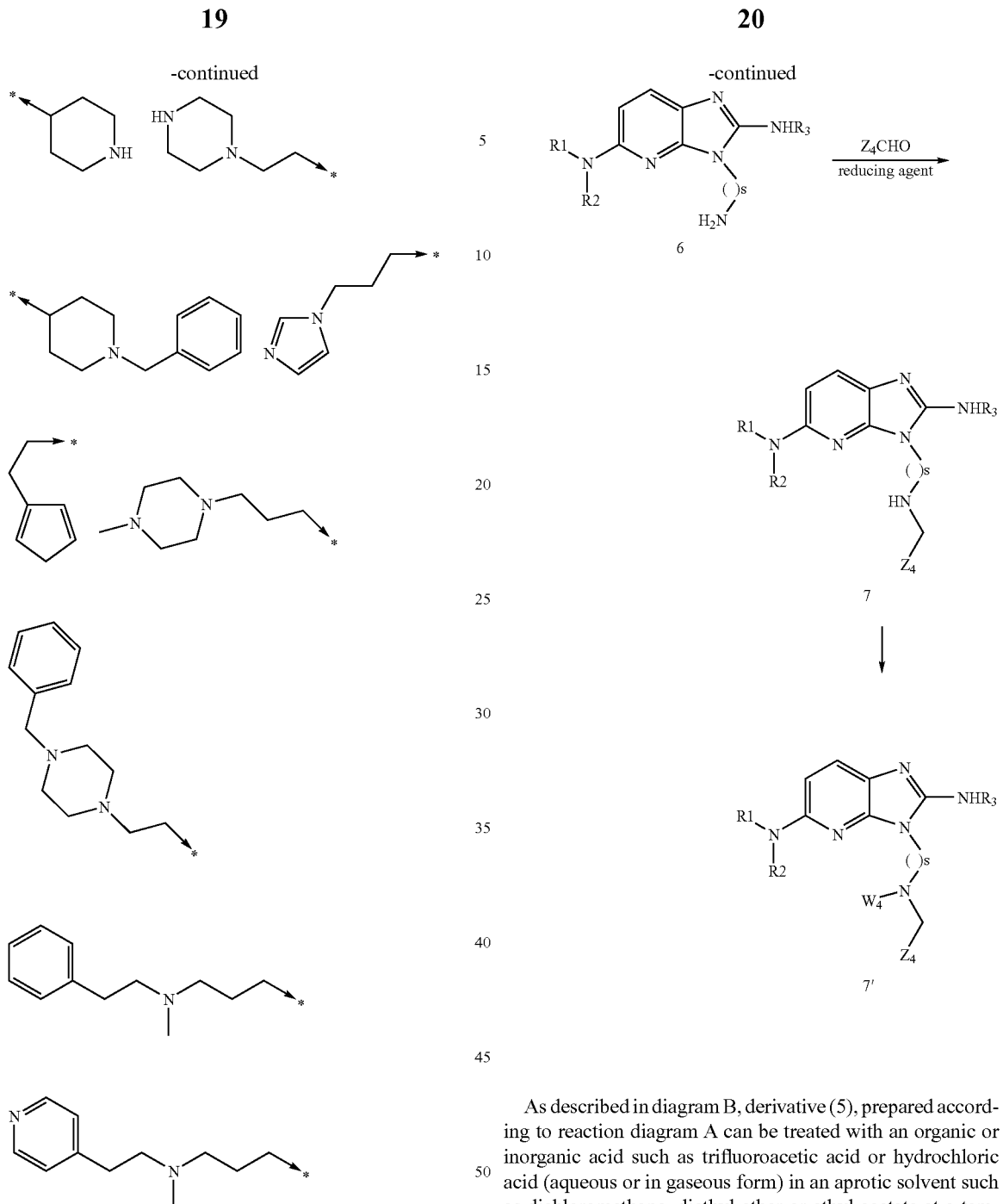

B. Preparation According to Reaction Diagram B:

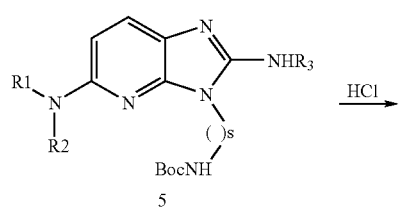

As described in diagram B, derivative (5), prepared according to reaction diagram A can be treated with an organic or inorganic acid such as trifluoroacetic acid or hydrochloric acid (aqueous or in gaseous form) in an aprotic solvent such as dichloromethane, diethyl ether or ethyl acetate at a temperature of 0-20° C. for 0.5 to 5 hours, in order to produce the amine (6). The amine (6) can react with an aldehyde in a protic or aprotic solvent, such as dichloromethane, tetrahydrofuran or methanol, for 1 to 15 hours at a temperature of 0-50° C. The resultant imine is then reduced in situ by a reducing agent supported or not supported on a resin, preferably sodium triacetoxyborohydride, sodium cyanoborohydride or borohydride supported on a resin, with or without the presence of an acid such as acetic acid, at a temperature of 20 to 50° C. for a duration of 0.2 to 5 hours, in order to produce compound (7). The secondary amine (7) can optionally undergo a second reducing amination under the same operating conditions as those described previously in order to produce the tertiary amine (7').

EXAMPLE B1

3-{2-[(4-methoxybenzyl)amino]ethyl}-$N^5$,$N^5$-bis(3-methylbutyl)-$N^2$-(3,4,5-trimethoxyphenyl)-3H-imidazo[4,5-b]pyridine-2,5-diamine

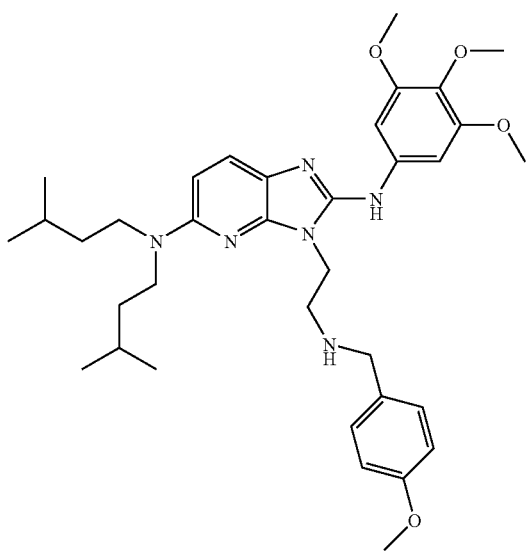

Stage 1: tert-butyl 2-[(6-chloro-3-nitropyridin-2-yl)amino]ethyl carbamate

Potassium carbonate (8.3 g, 1.2 eq) and tert-butyl-N(2-aminoethyl)carbamate (8 g, 1 eq) are added successively to 2,6-dichloro-3-nitropyridine (10.2 g, 1 eq) in solution in toluene (200 ml). After stirring for 4 hours at a temperature of approximately 20° C., the mixture is concentrated under reduced pressure at 40° C. then water (130 ml) and dichloromethane (250 ml) are added. After decantation and extractions, the combined organic phases are washed with salt water, dried over $Na_2SO_4$ then concentrated under reduced pressure at 40° C. Purification of the solid obtained, by flash chromatography on silica gel (eluent: heptane/ethyl acetate 7:3), produces the expected compound in the form of a yellow solid (12.5 g; 79% yield).

MS/LC: calculated MM=316.7; m/z=317.1 (MH+) NMR ($^1$H, 400 MHz, DMSO-$d_6$): δ 1.34 (s, 9H), 3.19 (dd, 2H), 3.56 (dd, 2H), 6.78 (d, 1H), 6.94 (t, 1H), 8.41 (d, 1H), 8.68 (t, 1H).

Stage 2: tert-butyl 2-({6-[bis(3-methylbutyl)amino]-3-nitropyridin-2-yl}amino)ethyl carbamate Potassium carbonate (207 mg, 1.5 eq) and diisoamylamine (188 mg, 1.2 eq) are added successively to a solution of tert-butyl 2-[(6-chloro-3-nitropyridin-2-yl)amino]ethylcarbamate (316 mg, 1 eq) in acetonitrile (10 ml). The mixture is heated to reflux for 5 hours then cooled down to ambient temperature and concentrated under reduced pressure at 40° C. The residue is taken up in dichloromethane (50 ml) and water (15 ml). After decantation and extractions, the combined organic phases are washed with salt water, dried over $Na_2SO_4$ then concentrated under reduced pressure at 40° C. Purification of the residue obtained, by flash chromatography on silica gel (eluent: heptane/ethyl acetate 9:1 to 7:3), produces the expected compound (430 mg; 98% yield).

MS/LC: calculated MM=437.6; m/z=438.3 (MH+) NMR ($^1$H, 400 MHz, DMSO-$d_6$): δ 0.91 (d, 12H), 1.35 (s, 9H), 1.45 (m, 4H), 1.60 (m, 2H), 3.17 (m, 2H), 3.40 (m, 2H), 3.56 (m, 4H), 6.10 (d, 1H), 6.93 (t, 1H), 8.04 (d, 1H), 8.83 (t, 1H).

Stage 4: tert-butyl 2-{5-[bis(3-methylbutyl)amino]-2-[(3,4,5-trimethoxyphenyl)amino]-3H-imidazo[4,5-b]pyridin-3-yl}ethyl carbamate Tert-butyl 2-({6-[bis(3-methylbutyl)amino]-3-nitropyridin-2-yl}amino)ethyl carbamate (400 mg, 1 eq) in solution in a mixture of ethyl acetate/ethanol 2:1 (60 ml), and 10% palladium on carbon (40 mg) are introduced into an autoclave. After stirring for 5 hours under a hydrogen atmosphere (3 bar) at a temperature of approximately 20° C., the mixture is filtered on celite in a flask containing 3,4,5-trimethoxyphenyl-isothiocyanate (248 mg, 1.2 eq). The filtrate is concentrated under reduced pressure at 40° C. then the residue is diluted in tetrahydrofuran (50 ml) and N-cyclohexylcarbodiimide-N-methyl-polystyrene resin (acquired from Novabiochem; load 1.9 mmol/g; 1.92 g, 4 eq) is added. The mixture is heated to reflux for 8 hours then cooled down to ambient temperature and filtered on frit. The filtrate is concentrated under reduced pressure at 40° C. Purification of the residue by flash chromatography on silica gel (eluent: heptane/ethyl acetate 9:1 to 6:4) produces the expected compound (324 mg; 59% yield).

MS/LC: calculated MM=598.8; m/z=599.4 (MH+) NMR ($^1$H, 400 MHz, DMSO-$d_6$): δ 0.93 (d, 12H), 1.28 (s, 9H), 1.45 (m, 4H), 1.60 (m, 2H), 3.29 (m, 2H), 3.43 (m, 4H), 3.61 (s, 3H), 3.77 (s, 6H), 4.17 (t, 2H), 6.24 (d, 1H), 6.90 (t, 1H), 7.21 (s, 2H), 7.45 (d, 1H), 8.54 (s, 1H).

Stage 5: 3-(2-aminoethyl)-$N^5$,$N^5$-bis(3-methylbutyl)-$N^2$-(3,4,5-trimethoxyphenyl)-3H-imidazo[4,5-b]pyridine-2,5-diamine A solution of hydrochloric acid in dioxane (4N, 3 ml) is added to a solution of tert-butyl 2-{5-[bis(3-methylbutyl)amino]-2-[(3,4,5-trimethoxyphenyl)amino]-3H-imidazo[4,5-b]pyridin-3-yl}ethyl carbamate (300 mg) in ethyl acetate (6 ml). After stirring for 4 hours at a temperature of approximately 20° C., the mixture is filtered. The solid obtained is washed with diethyl ether. The hydrochloride thus obtained is taken up in dichloromethane and water saturated with sodium hydrogen carbonate. After decantation and extractions, the combined organic phases are washed with salt water, dried over $Na_2SO_4$ then concentrated under reduced pressure at 40° C. in order to produce the expected compound in the form of a free base (237 mg, 95% yield).

MS/LC: calculated MM=498.7; m/z=499.3 (MH+) NMR ($^1$H, 400 MHz, DMSO-$d_6$): δ 0.93 (d, 12H), 1.45 (m, 4H), 1.59 (m, 2H), 2.98 (t, 2H), 3.35 (t, 4H), 3.61 (s, 3H), 3.77 (s, 6H), 4.10 (t, 2H), 6.23 (d, 1H), 7.16 (s, 2H), 7.44 (d, 1H).

Stage 6: 3-{2-[(4-methoxybenzyl)amino]ethyl}-$N^5$,$N^5$-bis(3-methylbutyl)-$N^2$-(3,4,5-trimethoxyphenyl)-3H-imidazo[4,5-b]pyridine-2,5-diamine A solution of 3-(2-aminoethyl)-$N^5$,$N^5$-bis(3-methylbutyl)-$N^2$-(3,4,5-trimethoxyphenyl)-3H-imidazo[4,5-b]pyridine-2,5-diamine (83 mg, 1 eq) and p-anisaldehyde (25 mg, 1 eq) in dichloromethane (1.5 ml) is stirred for 6 hours at a temperature of approximately 20° C. The mixture is diluted with methanol (2 ml) then sodium triacetoxyborohydride (70 mg, 2 eq) is added. After stirring for 0.5 hour at a temperature of approximately 20° C., dichloromethane (20 ml) and water saturated with sodium hydrogen carbonate (10 ml) are added to the mixture. After decantation and extractions, the combined organic phases are washed with salt water, dried over $Na_2SO_4$ then concentrated under reduced pressure at 40° C. Purification of the residue by flash chromatography on silica gel (eluent: heptane/ethyl acetate 1:1 to 2:8) produces the expected compound (70 mg, 68% yield).

MS/LC: calculated MM=618.8; m/z=619.4 (MH+) NMR ($^1$H, 400 MHz, DMSO-$d_6$): δ 0.92 (d, 12H), 1.44 (m, 4H), 1.57 (m, 2H), 2.89 (t, 2H), 3.44 (t, 4H), 3.60 (s, 3H), 3.70 (m, 8H), 4.19 (t, 2H), 6.23 (d, 1H), 6.80 (d, 2H), 7.06 (s, 2H), 7.18 (d, 2H), 7.45 (d, 1H), 9.90 (m, 1H).

C. Preparation According to Reaction Diagram C:

The compounds (7) for which s=3 can also be prepared according to the following diagram C:

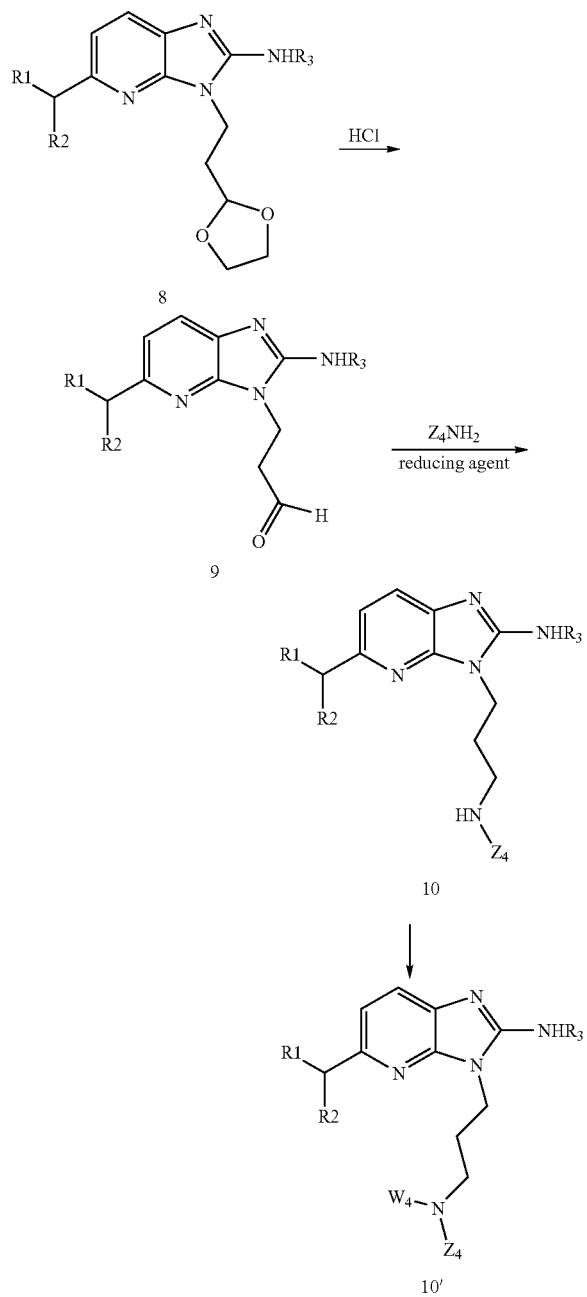

As described in diagram C, derivative (8) prepared according to reaction diagram A can be treated either with an organic acid such as pyridinium tosylate or paratoluenesulphonic acid in an aprotic solvent such as acetone in the presence of water, at a temperature of 20-70° C. for 2 to 12 hours, or by an inorganic acid such as aqueous hydrogen chloride in an aprotic solvent such as tetrahydrofuran at a temperature of 0-20° C. for 6 to 18 hours in order to produce compound (9). The aldehyde (9) can then be treated with an amine in a protic or aprotic solvent such as dichloromethane, tetrahydrofuran or methanol for 1 to 18 hours at a temperature of 20° C. The resultant imine is then reduced in situ by a reducing agent, preferably sodium triacetoxyborohydride or sodium cyanoborohydride, in the presence or absence of an acid such as acetic acid, at a temperature of 20-50° C. for a duration of 0.2 to 6 hours, in order to produce compound (10). The secondary amine (10) can optionally undergo a second reducing amination under the same operating conditions as those described previously in order to produce the tertiary amine (10').

According to reaction diagram B or C, the following compounds can be prepared:

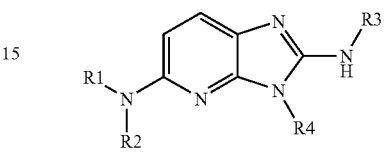

in which $R_1R_2N$ represents one of the radicals below:

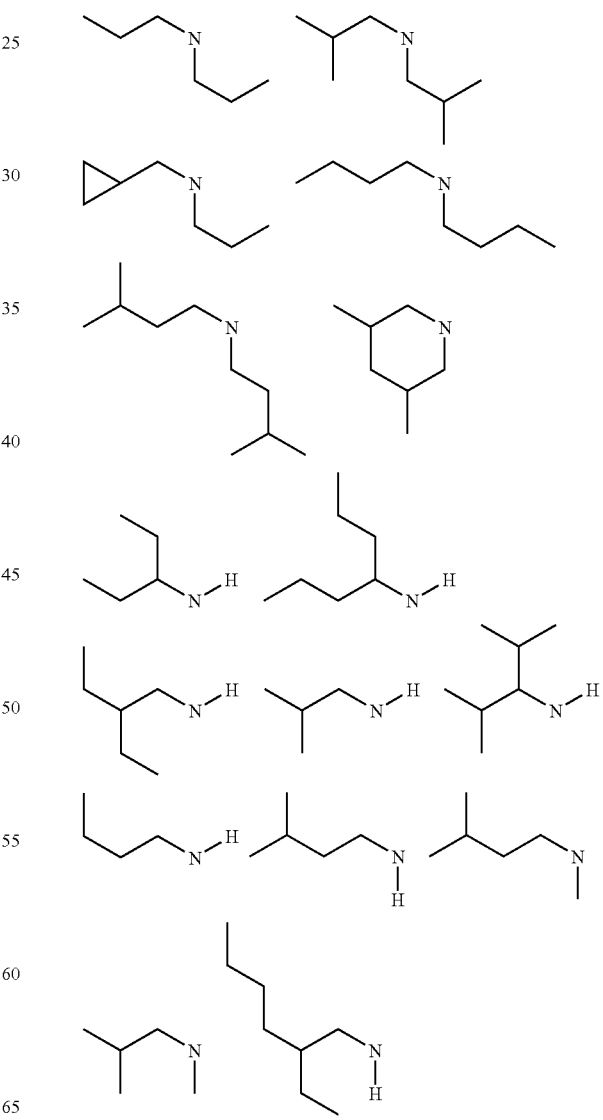

$R_3$ represents one of the radicals below:

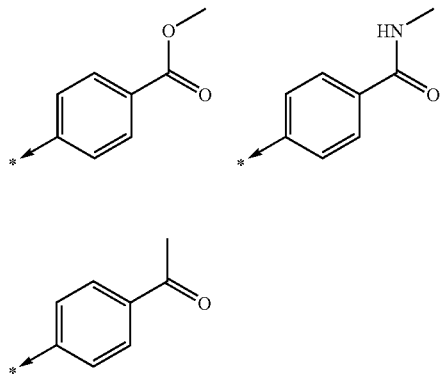

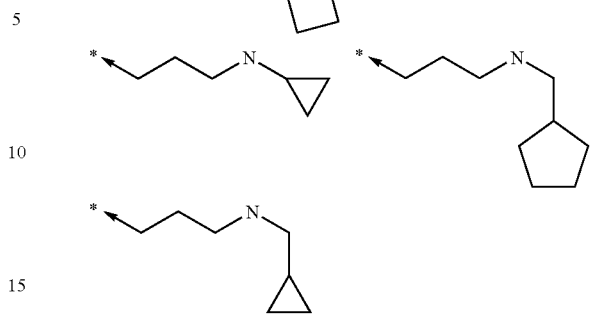

-continued

D. Preparation According to Reaction Diagram D:

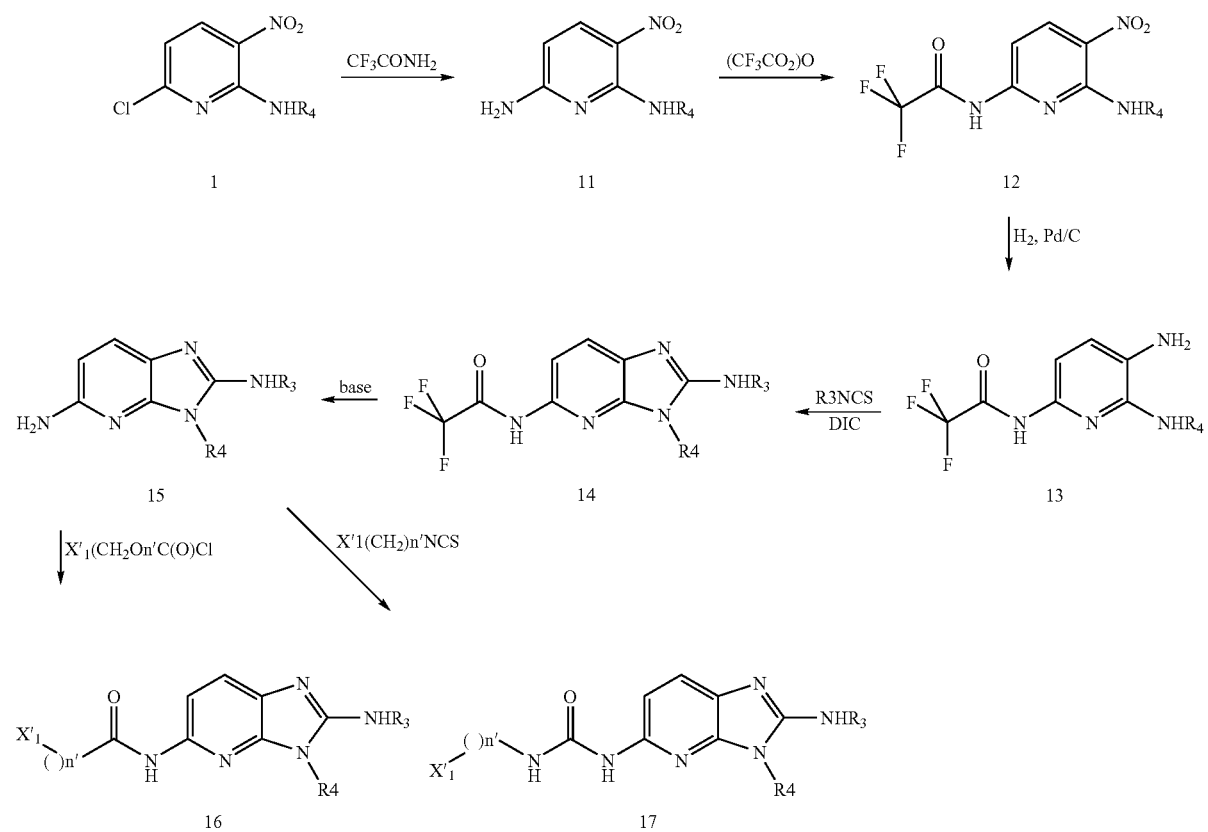

and $R_4$ represents one of the radicals below:

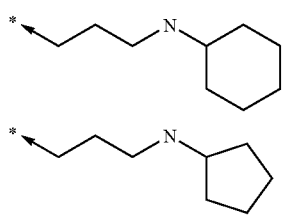

As described in diagram D, the chlorinated derivative (1) prepared according to reaction diagram A, can be converted to aniline (11) by treatment with trifluoroacetamide, in the presence of an inorganic base such as caesium or potassium carbonate and a phase transfer catalyst such as tetrabutylammonium bromide, in a polar aprotic solvent such as dimethylformamide, at a temperature of 80-110° C. for 2-6 hours. The aniline (11) can be protected in the form of trifluoroacetamide by treatment with trifluoroacetic anhydride in the presence of a tertiary amine such as triethylamine or pyridine in an aprotic solvent such as dichloromethane at a temperature of 0-20° C. for 0.2-2 hours, in order to produce compound (12). The nitro derivative (12) is reduced by catalytic hydrogenation in the presence of 10% palladium on carbon in an inert solvent such as methanol, ethanol, ethyl acetate or a mixture of these solvents, at a temperature of 18-25° C., for 2 to 8 hours in order to produce the dianiline (13). Derivative (13) is then treated with an isothiocyanate in the presence of a coupling agent supported or not supported on a resin such as diisopropylcarbodiimide or dicyclohexylcarbodiimide or N-cyclohexylcarbodiimide N-methyl polystyrene resin in an inert solvent such as tetrahydrofuran, methylene chloride, or chloroform at a temperature of 20-70° C. for 2 to 72 hours in order to produce derivative (14). The trifluoroacetamide (14) is hydrolysed in the presence of potassium or sodium carbonate in a polar protic solvent such as methanol or ethanol in the presence of water, at a temperature of 50-80° C. for 8-32 hours in order to produce the aniline (15). The aniline (15) can react with an acid chloride in an aprotic solvent such as dichloromethane or tetrahydrofuran in the presence of a base such as a tertiary amine supported or not supported on a resin, such as triethylamine or morpholino-methylpolystyrene resin, at a temperature of 040° C. for 0.3-2 hours in order to produce the amide (16). The aniline (15) can also react with a isothiocyanate in an aprotic solvent such as tetrahydrofuran at a temperature of 20-70° C. for 5-24 hours in order to produce the thiourea (17).

EXAMPLE D1

N-{3-(2-aminoethyl)-2-[(3,4,5-trimethoxyphenyl)amino]-3H-imidazo[4,5-b]pyridin-5-yl}-2-propyl-pentanamide hydrochloride

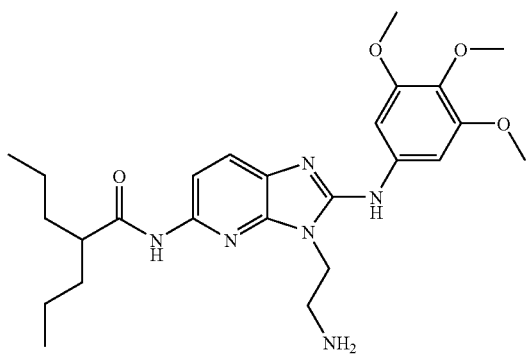

Stage 1: tert-butyl 2-[(6-amino-3-nitropyridin-2-yl)amino]ethyl carbamate

Potassium carbonate (0.87 mg, 1 eq), tetrabutylammonium bromide (0.2 g, 0.1 eq) and trifluoroacetamide (1.4 g, 2 eq) are added successively to a solution of tert-butyl 2-[(6-chloro-3-nitropyridin-2-yl)amino]ethyl carbamate prepared according to Example B1, (2 g, 1 eq) in dimethylformamide (100 ml). The mixture is heated for 4 hours at 100° C. then cooled down to ambient temperature and filtered on frit. The filtrate is concentrated under reduced pressure at 40° C. then water (40 ml) and dichloromethane (100 ml) are added to the residue obtained. After decantation and extractions, the combined organic phases are washed with salt water, dried over $Na_2SO_4$ then concentrated under reduced pressure at 40° C. Purification of the solid obtained, by flash chromatography on silica gel (eluent: heptane/ethyl acetate 6:4), produces the expected compound (1.21 g; 64% yield).

MS/LC: calculated MM=297.3; m/z=298.2 (MH+) NMR ($^1$H, 400 MHz, DMSO-$d_6$): δ 1.35 (s, 9H), 3.17 (dd, 2H), 3.53 (dd, 2H), 5.90 (d, 1H), 6.93 (t, 1H), 7.38 (m, 2H), 7.98 (d, 1H), 8.88 (t, 1H).

Stage 2: tert-butyl 2-({3-nitro-6-[(trifluoroacetyl)amino]pyridin-2-yl}amino)ethyl carbamate Triethylamine (0.59 ml) then trifluoroacetic anhydride (0.56 ml) are added successively to a solution cooled down to 0° C. of tert-butyl 2-[(6-amino-3-nitropyridin-2-yl)amino]ethyl carbamate (840 mg, 1 eq) in dichloromethane (25 ml). After stirring for 1 hour at 0° C., water (10 ml) is added to the mixture. After decantation and extractions, the combined organic phases are washed with salt water, dried over $Na_2SO_4$ then concentrated under reduced pressure at 40° C. The yellow solid obtained is recrystallized from a dichloromethane/heptane mixture and washed with diethyl ether (910 mg; 81% yield).

NMR ($^1$H, 400 MHz, DMSO-$d_6$): δ 1.31 (s, 9H), 3.22 (dd, 2H), 3.62 (dd, 2H), 6.86 (t, 1H), 7.27 (d, 1H), 8.50 (d, 1H), 11.90 (s, 1H).

Stage 3: tert-butyl 2-({3-amino-6-[(trifluoroacetyl)amino]pyridin-2-yl}amino)ethyl carbamate Tert-butyl 2-({3-nitro-6-[(trifluoroacetyl)amino]pyridin-2-yl}amino)ethyl carbamate (900 mg) in solution in a mixture of ethyl acetate/ethanol 2:1 (120 ml), and 10% palladium on carbon (130 mg) are introduced into an autoclave. After stirring for 15 hours under a hydrogen atmosphere (3 bar) at a temperature of approximately 20° C., the catalyst is eliminated by filtration on celite and the filtrate is concentrated under reduced pressure at 40° C. in order to produce the expected compound (820 mg; 98% yield).

MS/LC: calculated MM=363.3; m/z=364.2 (MH+) NMR ($^1$H, 400 MHz, DMSO-$d_6$): δ 1.36 (s, 9H), 3.15 (dd, 2H), 3.37 (dd, 2H), 4.70 (m, 2H), 5.77 (t, 1H), 6.72 (d, 1H), 6.79 (t,1H), 6.88 (d, 1H), 10.81 (s, 1H).

Stage 4: tert-butyl 2-{5-[(trifluoroacetyl)amino]-2-[(3,4,5-trimethoxyphenyl)amino]-3H-imidazo[4,5-b]pyridin-3-yl}ethylcarbamate 3,4,5-trimethoxyphenyl isothiocyanate (600 mg, 1.2 eq) and N-cyclohexylcarbodiimide-N-methyl-polystyrene resin (acquired from Novabiochem; load 1.9 mmol/g; 4.6 g, 4 eq) are added successively to a solution of tert-butyl 2-({3-amino-6-[(trifluoroacetyl)amino]pyridin-2-yl}amino)ethyl carbamate (800 mg, 1 eq) in tetrahydrofuran (50 ml). The mixture is heated to reflux for 24 hours then cooled down to ambient temperature and filtered on frit. The filtrate is concentrated under reduced pressure at 40° C. Purification of the residue by flash chromatography on silica gel (eluent: heptane/ethyl acetate 6:4 to 3:7) produces the expected compound in the form of a cream solid (750 mg; 62% yield).

MS/LC: calculated MM=554.5; m/z=555.2 (MH+) NMR ($^1$H, 400 MHz, DMSO-$d_6$): δ 1.24 (s, 9H), 3.32 (m, 2H), 3.63 (s, 3H), 3.79 (s, 6H), 4.30 (m, 2H), 6.95 (t, 1H), 7.31 (s, 2H), 7.59 (d, 1H), 7.72 (d, 1H), 8.93 (s, 1H), 11.7 (s, 1H).

Stage 5: tert-butyl 2-{5-amino-2-[(3,4,5-trimethoxyphenyl)amino]-3H-imidazo[4,5-b]pyridin-3-yl}ethyl carbamate Potassium carbonate (1.17 g, 10 eq) is added to tert-butyl 2-{5-[(trifluoroacetyl)amino]-2-[(3,4,5-trimethoxyphenyl)amino]-3H-imidazo[4,5-b]pyridin-3-yl}ethyl carbamate (470 mg, 1 eq) in methanol (32 ml) and water (2 ml). The mixture is heated to reflux for 26 hours then cooled down to ambient temperature and concentrated under reduced pressure at 40° C. Water (15 ml) and dichloromethane (50 ml) are added to the residue. After decantation and extractions, the combined organic phases are washed with salt water, dried over Na$_2$SO$_4$ then concentrated under reduced pressure at 40° C. in order to produce the expected compound (379 mg; 97% yield).

MS/LC: calculated MM=458.5; m/z=459.2 (MH+) NMR ($^1$H, 400 MHz, DMSO-d$_6$): δ 1.31 (s, 9H), 3.25 (m, 2H), 3.61 (s, 3H), 3.77 (s, 6H), 4.13 (t, 2H), 5.50 (m, 2H), 6.22 (d, 1H), 7.01 (t, 1H), 7.21 (s, 2H), 7.37 (d, 1H), 8.50 (s, 1H).

Stage 6: tert-butyl 2-{5-[(2-propylpentanoyl)amino]-2-[(3,4,5-trimethoxyphenyl)amino]-3H-imidazo[4,5-b]pyridin-3-yl}ethyl carbamate Morpholino-methylpolystyrene (acquired from Novabiochem; load 3.64 mmol/g; 33 mg, 1.5 eq) and 2-propylpentanoyl chloride (15 mg, 1.2 eq) are added successively to a solution of tert-butyl 2-{5-amino-2-[(3,4,5-trimethoxyphenyl)amino]-3H-imidazo[4,5-b]pyridin-3-yl}ethyl carbamate (37 mg, 1 eq) in dichloromethane (2 ml). The mixture is stirred for 1 hour at a temperature of approximately 20° C. then filtered on frit. The filtrate is concentrated under reduced pressure at 40° C. Purification of the residue by flash chromatography on silica gel (eluent: heptane/ethyl acetate 4:6 to 3:7) produces the expected compound (34 mg; 73% yield).

MS/LC: calculated MM=584.7; m/z=585.3 (MH+) NMR ($^1$H, 400 MHz, DMSO-d$_6$): δ 0.86 (t, 6H), 1.27 (s, 9H), 1.18-1.34 (m, 6H), 1.53 (m, 2H), 2.65 (m, 1H), 3.31 (m, 2H), 3.63 (s, 3H), 3.79 (s, 6H), 4.25 (t, 2H), 7.0 (t, 1H), 7.30 (s, 2H), 7.61 (d, 1H), 7.92 (d, 1H), 8.80 (s, 1H), 10.18 (s, 1H).

Stage 7: N-{3-(2-aminoethyl)-2-[(3,4,5-trimethoxyphenyl)amino]-3H-imidazo[4,5-b]pyridin-5-yl}-2-propylpentanamide hydrochloride A solution of hydrochloric acid in dioxane (4N, 1 ml) is added to a solution of tert-butyl 2-{5-[(2-propylpentanoyl)amino]-2-[(3,4,5-trimethoxyphenyl)amino]-3H-imidazo[4,5-b]pyridin-3-yl}ethyl carbamate (30 mg) in ethyl acetate (1 ml). After stirring for 1 hour at a temperature of approximately 20° C., the mixture is concentrated under reduced pressure at 40° C. The solid obtained is washed with ethyl ether and dried (29 mg, 97% yield).

MS/LC: calculated MM=485.2; m/z=484.6 (MH+) NMR ($^1$H, 400 MHz, DMSO-d$_6$): δ 0.86 (t, 6H), 1.18-1.36 (m, 6H), 1.56 (m, 2H), 2.62 (m, 1H), 3.31 (m, 2H), 3.69 (s, 3H), 3.79 (s, 6H), 4.66 (t, 2H), 7.0 (m, 2H), 7.72 (d, 1H), 8.03 (d, 1H), 8.49 (m, 3H), 10.58 (s, 1H).

EXAMPLE D2

N-{3-(2-aminoethyl)-2-[(3,4,5-trimethoxyphenyl)amino]-3H-imidazo[4,5-b]pyridin-5-yl}-N'-(sec-butyl)thiourea

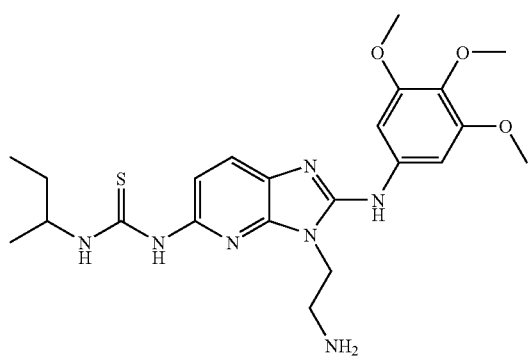

Stage 1: tert-butyl 2-{5-{[(sec-butylamino)carbonothioyl]amino}-2-[(3,4,5-trimethoxyphenyl)amino]-3H-imidazo[4,5-b]pyridin-3-yl}ethyl carbamate A solution of tert-butyl 2-{5-amino-2-[(3,4,5-trimethoxyphenyl)amino]-3H-imidazo[4,5-b]pyridin-3-yl}ethyl carbamate prepared according to Example D1 (37 mg, 1 eq) and sec-butyl isothiocyanate (20 mg, 2 eq) in tetrahydrofuran (3 ml) is heated to reflux for 17 hours then cooled down to ambient temperature and concentrated under reduced pressure at 40° C. Purification of the residue by flash chromatography on silica gel (eluent: heptane/ethyl acetate 4:6 to 3:7) produces the expected compound (30 mg; 65% yield).

MS/LC: calculated MM=573.7; m/z=574.2 (MH+) NMR ($^1$H, 400 MHz, DMSO-d$_6$): δ 0.94 (t, 3H), 1.23 (s, 9H), 1.29 (d, 3H), 1.68 (m, 1H), 1.75 (m, 1H), 3.31 (m, 2H), 3.62 (s, 3H), 3.78 (s, 6H), 4.25 (t, 2H), 4.30 (m, 1H), 6.90 (d, 1H), 6.95 (t, 1H), 7.27 (s, 2H), 7.67 (d, 1H), 8.82 (s, 1H), 10.37 (s, 1H), 11.04 (d, 1H).

Stage 2: N-{3-(2-aminoethyl)-2-[(3,4,5-trimethoxyphenyl)amino]-3H-imidazo[4,5-b]pyridin-5-yl}-N'-(sec-butyl)thiourea hydrochloride A solution of hydrochloric acid in dioxane (4N, 0.7 ml) is added to a solution of tert-butyl 2-{5-{[(sec-butylamino)carbonothioyl]amino}2-[(3,4,5-trimethoxyphenyl)amino]-3H-imidazo[4,5-b]pyridin-3-yl}ethyl carbamate (22 mg) in ethyl acetate (1 ml). After stirring for 1 hour at a temperature of approximately 20° C., the mixture is concentrated under reduced pressure at 40° C. The solid obtained is washed with ethyl ether and dried (20 mg, 91% yield).

MS/LC: calculated MM=473.6; m/z=474.2 (MH+) NMR ($^1$H, 400 MHz, DMSO-d$_6$): δ 0.94 (t, 3H), 1.27 (d, 3H), 1.69 (m, 2H), 3.31 (m, 2H), 3.67 (s, 3H), 3.79 (s, 6H), 4.32 (m, 1H), 4.68 (m, 2H), 7.10 (d, 1H), 7.18 (m, 2H), 7.78 (d, 1H), 8.53 (s, 3H), 10.50 (m, 1H), 10.60 (s, 1H).

According to reaction diagram D and according to the procedure described for N-{3-(2-aminoethyl)-2-[(3,4,5-trimethoxyphenyl)amino]-3H-imidazo[4,5-b]pyridin-5-yl}-2-propylpentanamide hydrochloride, the following compounds can be prepared:

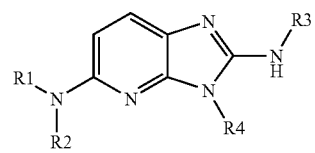

in which $R_1R_2N$ represents one of the radicals below:

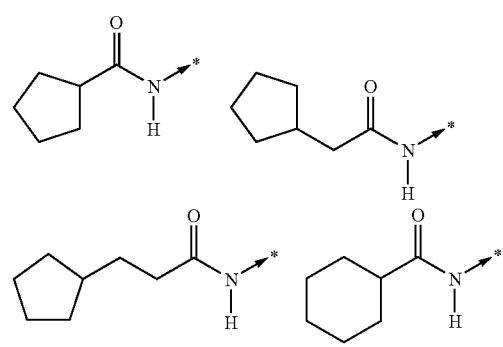

-continued
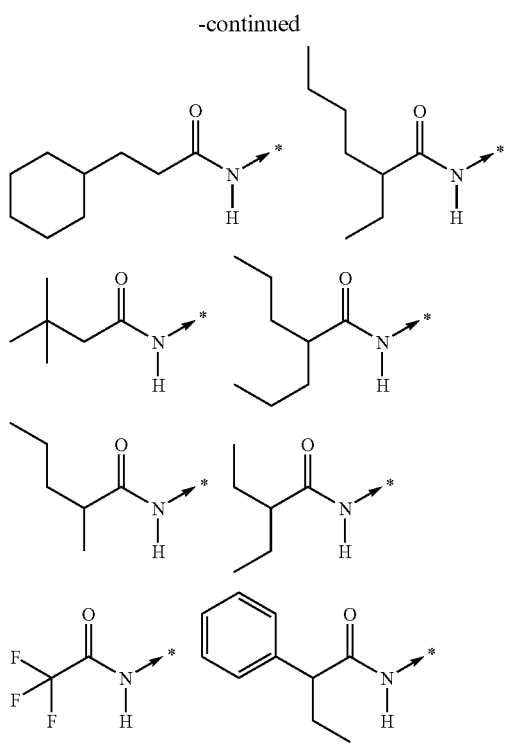
$R_3$ represents one of the radicals below:
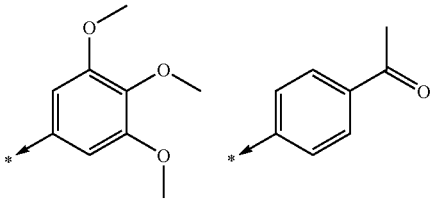
and $R_4$ represents one of the radicals below:
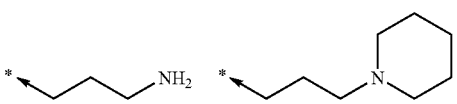
E. Preparation According to Reaction Diagram E:
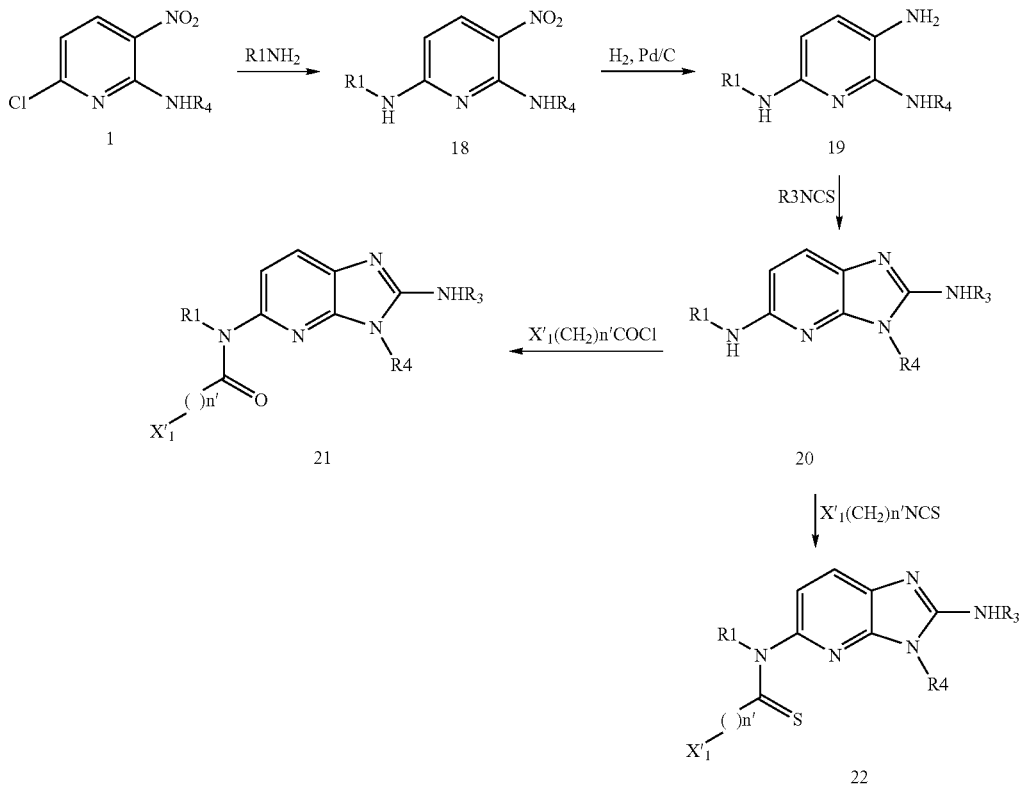

As described in diagram E, the chlorinated derivative (1) prepared according to reaction diagram A, can react with a primary amine, in the presence of an organic base such as a tertiary amine or an inorganic base such as potassium or caesium carbonate, in a polar aprotic solvent such as acetonitrile, dimethylformamide or HMPA at a temperature of 20-70° C. for 2-18 hours in order to produce compound (18). The nitro function of compound (18) is reduced by catalytic hydrogenation in the presence of 10% palladium on carbon in an inert solvent such as methanol, ethanol, ethyl acetate or a mixture of these solvents, at a temperature of 18-25° C., for 2 to 8 hours in order to produce the dianiline (19). Derivative (19) is then treated with an isothiocyanate in the presence of a coupling agent supported or not supported on a resin such as diisopropylcarbodiimide or dicyclohexylcarbodiimide or N-cyclohexylcarbodiimide N-methyl polystyrene resin in an inert solvent such as tetrahydrofuran, methylene chloride, or chloroform at a temperature of 20-70° C. for 2 to 72 hours in order to produce derivative (20). Alternatively, derivative (19) can be treated with an isothiocyanate in an inert solvent such as tetrahydrofuran, methylene chloride, chloroform or ethanol at a temperature of 20-80° C. for 1-16 hours then the resultant thiourea can be treated with yellow mercury(II) oxide in the presence of a catalytic quantity of sulphur in a polar solvent such as methanol or ethanol for 2 to 24 hours at a temperature of 20-80° C. in order to produce (20). Derivative (20) can react with an acid chloride in an aprotic solvent such as dichloromethane or tetrahydrofuran in the presence of a base such as a tertiary amine supported or not supported on a resin, such as triethylamine or morpholino-methylpolystyrene resin at a temperature of 0-40° C. for 0.3-2 hours in order to produce the amide (21). The aniline (20) can also react with an isothiocyanate in an aprotic solvent such as tetrahydrofuran at a temperature of 20-70° C. for 548 hours in order to produce the thiourea (22).

EXAMPLE E1

N-[2-[(4-acetylphenyl)amino]-3-(3-piperidin-1-ylpropyl)-3H-imidazo[4,5-b]pyridin-5-yl]-N-butylbutanamide hydrochloride

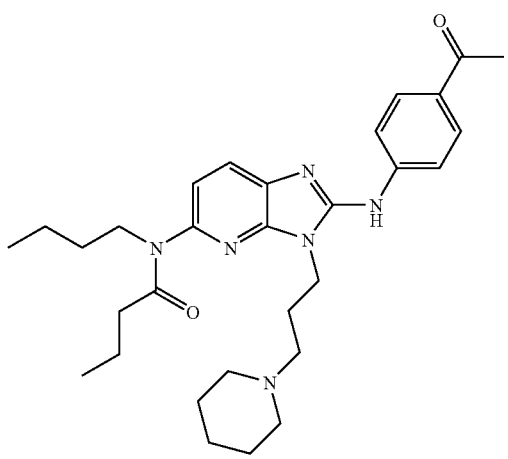

Stage 1: $N^6$-butyl-3-nitro-$N^2$-(3-piperidin-1-ylpropyl)pyridine-2,6-diamine

Potassium carbonate (930 mg, 2 eq) and a solution of 1-butylamine (300 mg, 1.2 eq) in acetonitrile (2 ml) are added successively to a solution of 6-chloro-3-nitro-N-(3-piperidin-1-ylpropyl)pyridin-2-amine (1 g, 1 eq; prepared according to Example A2) in acetonitrile (80 ml). The mixture is heated to reflux for 15 hours then cooled down to ambient temperature and concentrated under reduced pressure at 40° C. The residue is taken up in dichloromethane (200 ml) and water (90 ml). After decantation and extractions, the combined organic phases are washed with salt water, dried over $Na_2SO_4$ then concentrated under reduced pressure at 40° C. Purification of the residue obtained, by flash chromatography on silica gel (eluent: heptane/ethyl acetate 9:1 to 100% ethyl acetate), produces the expected compound (1.1 g; 98% yield).

MS/LC: calculated MM=335.4; m/z=336.4 (MH+) NMR ($^1$H, 400 MHz, DMSO-$d_6$): δ 0.89 (t, 3H), 1.34 (m, 4H), 1.48 (m, 6H), 1.72 (m, 2H), 2.29 (m, 6H), 3.33 (m, 2H), 3.53 (m, 2H), 5.90 (d, 1H), 7.91 (d, 1H), 8.06 (t, 1H), 9.12 (t, 1H).

Stage 2: 1-(4-{[5-(butylamino)-3-(3-piperidin-1-ylpropyl)-3H-imidazo[4,5-b]pyridin-2-yl]amino}phenyl)ethanone $N^6$-butyl-3-nitro-$N^2$-(3-piperidin-1-ylpropyl)pyridine-2, 6-diamine (500 mg) in solution in a mixture of ethyl acetate/ethanol 3:1 (10 ml), and 10% palladium on carbon (50 mg) are introduced into an autoclave. After stirring for 3 hours under a hydrogen atmosphere (3 bar) at a temperature of approximately 20° C., the mixture is filtered on celite in a flask containing a solution of 4-acetylphenyl-isothiocyanate (270 mg, 1 eq) in tetrahydrofuran (10 ml). N-cyclohexylcarbodiimide-N-methyl-polystyrene resin (acquired from Novabiochem; load 1.9 mmol/g; 2.63 g, 3 eq) is added to the filtrate thus obtained. The mixture is heated to reflux for 15 hours, cooled down to ambient temperature then filtered on frit and the filtrate is concentrated under reduced pressure at 40° C. Purification of the residue by flash chromatography on silica gel (eluent: 100% dichloromethane to dichloromethane/methanol 9:1) produces the expected compound (230 mg; 34% yield).

MS/LC: calculated MM=448.6; m/z=449.3 (MH+)

Stage 3: N-[2-[(4-acetylphenyl)amino]-3-(3-piperidin-1-ylpropyl)-3H-imidazo[4,5-b]pyridin-5-yl]-N-butylbutanamide hydrochloride Morpholinomethyl resin (acquired from Novabiochem, load=3.5 mmol/g; 69 mg, 2 eq) and butyryl chloride (17 mg) are added successively to a solution of 1-(4-{[5-(butylamino)-3-(3-piperidin-1-ylpropyl)-3H-imidazo[4,5-b]pyridin-2-yl]amino}phenyl)ethanone (54 mg) in anhydrous dichloromethane (1 ml). After stirring for 30 minutes at ambient temperature, aminomethylpolystyrene resin is added in order to trap the excess of acid chloride. After stirring for 2 hours at ambient temperature, the mixture is filtered and concentrated under reduced pressure at 40° C. The corresponding hydrochloride salt is formed by adding a 1N solution of hydrochloric acid in ethyl ether. The precipitate obtained is filtered and dried in order to produce the expected compound (68 mg).

MS/LC: calculated MM=518.7; m/z=519.4 (MH+).

According to reaction diagram E and according to the procedure described for N-[2-[(4-acetylphenyl)amino]-3-(3-piperidin-1-ylpropyl)-3H-imidazo[4,5-b]pyridin-5-yl]-N-butylbutanamide hydrochloride, the following compounds can be prepared:

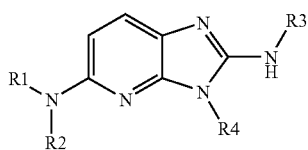

in which $R_1R_2N$ represents one of the radicals below:

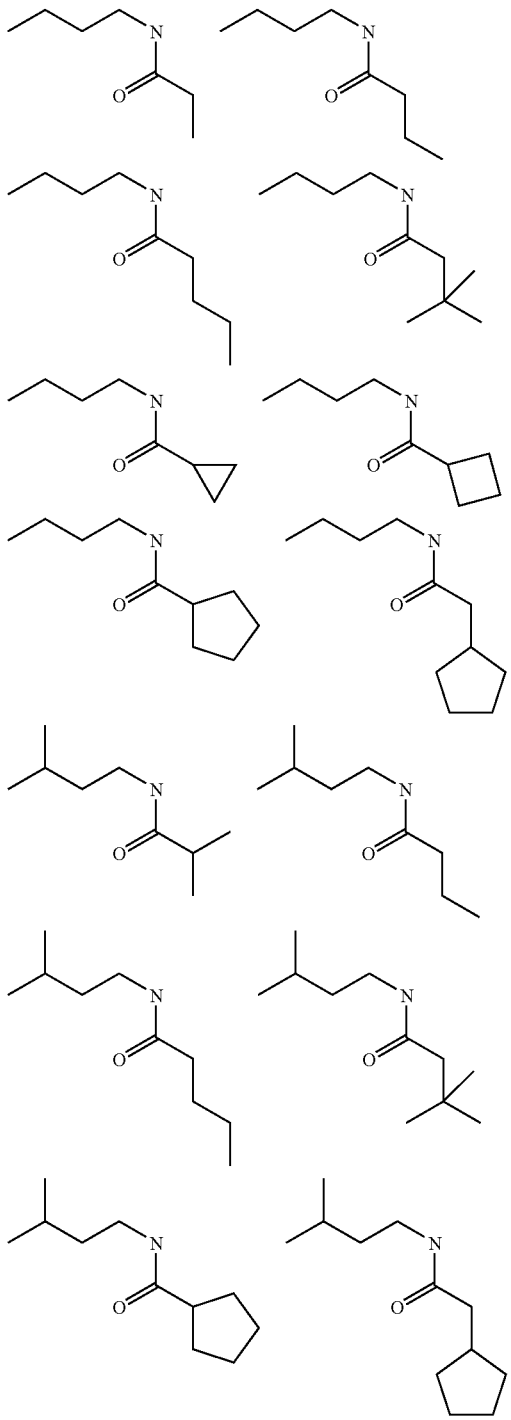

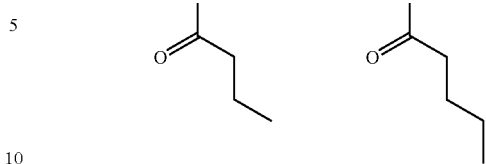

$R_3$ represents one of the radicals below:

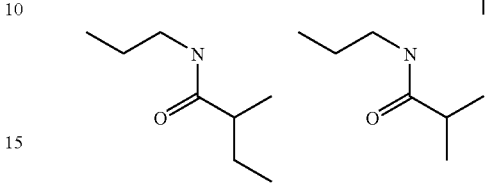

and $R_4$ represents one of the radicals below:

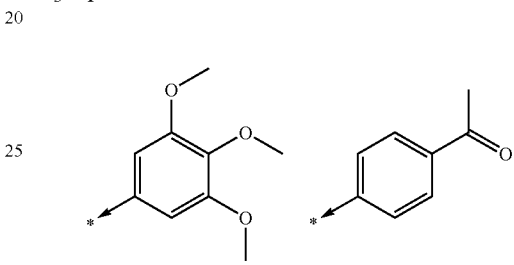

A subject of the present invention is also a process for the preparation of a compound of formula (I) as defined above, characterized in that the compound of general formula:

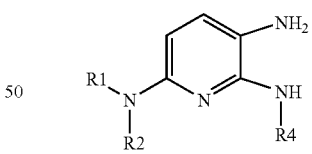

in which $R_1$, $R_2$, $R_4$ have the meaning indicated above, is treated with an isothiocyanate of general formula $R_3N{=}C{=}S$ in which $R_3$ has the meaning above, in the presence of a coupling agent or yellow mercury(II) oxide in the presence of sulphur, for a duration of 3 to 48 hours, in a protic or aprotic solvent, at a temperature of 50 to 80° C.

The coupling agent can be supported such as N-methylcyclohexylcarbodiimide N-methyl polystyrene resin or not supported such as diisopropylcarbodiimide, diethylcarbodiimide or dicyclohexylcarbodiimide. A protic solvent such as methanol or ethanol or an aprotic solvent such as tetrahydrofuran or acetonitrile can be used.

A subject of the invention is also a compound of general formula (II)

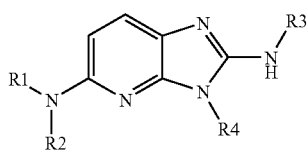

in racemic, or enantiomeric form or any combinations of these forms and in which:
$R_1$ and $R_2$ represent, independently, the hydrogen atom, a $(C_1-C_8)$alkyl radical optionally substituted by hydroxy; $(C_2-C_6)$alkenylalkenyl, a bicycloalkyl or a radical of formula $-(CH_2)_n-X_1$ or $-X-(CH_2)_n-X'_1$;
X represents $-C(O)-$ or $-C(S)-NH-$;
$X_1$ represents a $(C_1-C_6)$alkoxy, $(C_3-C_7)$cycloalkyl, adamantyl, heterocycloalkyl, aryl or heteroaryl radical,
  the $(C_3-C_7)$cycloalkyl, heterocycloalkyl, aryl and heteroaryl radicals being optionally substituted by one or more identical or different substituents chosen from: $-(CH_2)_{n1}-V_1-Y_1$, halo, nitro and cyano;
$V_1$ represents $-O-$, $-S-$ or a covalent bond;
$Y_1$ represents a $(C_1-C_6)$alkyl radical optionally substituted by one or more identical or different halo radicals, or aryl;
n and n' represent an integer from 0 to 6 and n, an integer from 0 to 2 (it being understood that when n is equal to 0, then $X_1$ does not represent the alkoxy radical);
$X'_1$ represents the hydrogen atom; a $(C_1-C_6)$alkyl radical optionally substituted by one or more identical or different halo radicals; $(C_3-C_7)$cycloalkyl; or aryl optionally substituted by one or more identical or different substituents chosen from: halo, nitro, cyano, $(C_1-C_6)$alkyl optionally substituted by one or more identical or different halo radicals, and $(C_1-C_6)$alkoxy optionally substituted by one or more identical or different halo radicals;
or $R_1$ and $R_2$ form together, with the nitrogen atom to which they are attached, a heterobicycloalkyl or a heterocycloalkyl optionally substituted by one or more identical or different substituents chosen from: hydroxy, $(C_1-C_6)$alkyl, $(C_1-C_6)$hydroxyalkyl, $(C_1-C_6)$alkoxy-carbonyl, $-(CH_2)_{n''}-A$, $-C(O)-NV_1'Y_1'$, and heterocycloalkyl; or $R_1$ and $R_2$ form together a radical of formula:

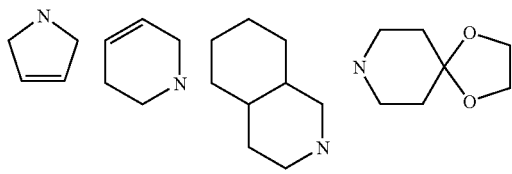

$V_1'$ and $Y_1'$ represent, independently, the hydrogen atom or a $(C_1-C_6)$alkyl radical;
A represents an aryl radical optionally substituted by one or more identical or different substituents chosen from: halo, nitro, cyano, $(C_1-C_6)$alkyl optionally substituted by one or more identical or different halo radicals, and $(C_1-C_6)$alkoxy optionally substituted by one or more identical or different halo radicals;
n" represents an integer from 0 to 2;
$R_3$ represents $-(CH_2)_p-Z_3$ or $-C(O)-Z'_3$ $Z_3$ represents a $(C_1-C_6)$alkyl, $(C_2-C_6)$alkenylalkenyl, $(C_1-C_6)$alkoxy, $(C_1-C_6)$alkoxy-carbonyl, $(C_1-C_6)$alkyl-amino-carbonyl, $(C_3-C_7)$cycloalkyl, heterocycloalkyl, aryl or heteroaryl radical,
the $(C_3-C_7)$cycloalkyl and heterocycloalkyl radicals being optionally substituted by one or more identical or different $(C_1-C_6)$alkyl radicals,
the aryl radical being optionally substituted by one or more identical or different substituents chosen from: halo, nitro, azido or $-(CH_2)_{p'}-V_3-Y_3$;
$V_3$ represents $-O-$, $-S-$, $-C(O)-$, $-C(O)-O-$, $-NH-C(O)-$, $-C(O)-NR'_3-$, $-NH-C(O)-NR'_3-$, $-NH-C(O)-NR'_3-O-$ (to illustrate a preference which is not exemplified) or a covalent bond;
$Y_3$ represents the hydrogen atom or a $(C_1-C_6)$alkyl radical optionally substituted by one or more identical or different halo radicals;
or $Z_3$ represents a radical of formula

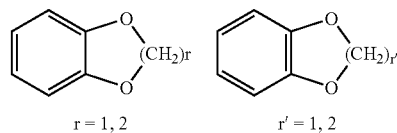

$Z'_3$ represents an aryl radical optionally substituted by one or more identical or different substituents chosen from: halo, nitro and $-(CH_2)_{p''}-V'_3-Y'_3$;
$V'_3$ represents $-O-$, $-C(O)-$, $-C(O)-O-$, $-C(O)-NR'_3-$, $-NH-C(O)-$, $-NH-C(O)-NR'_3-$ or a covalent bond;
$Y'_3$ represents the hydrogen atom or a $(C_1-C_6)$alkyl radical optionally substituted by one or more identical or different halo radicals;
$R'_3$ represents the hydrogen atom, a $(C_1-C_6)$alkyl or $(C_1-C_6)$alkoxy radical;
p, p' and p" represent, independently, an integer from 0 to 4;
$R_4$ represents a radical of formula $-(CH_2)_s-R'_4$;
$R'_4$ represents a heterocycloalkyl containing at least one nitrogen atom and optionally substituted by $(C_1-C_6)$alkyl or aralkyl; a heteroaryl containing at least one nitrogen atom and optionally substituted by $(C_1-C_6)$alkyl; or a radical of formula $-NW_4W'_4$
$W_4$ represents the hydrogen atom or $(C_1-C_8)$alkyl;
$W'_4$ represents a radical of formula $-(CH_2)_{s'}-Z_4$;
$Z_4$ represents the hydrogen atom, $(C_1-C_8)$alkyl, $(C_2-C_6)$ alkenyl alkenyl; $(C_3-C_7)$cycloalkyl optionally substituted by one or more identical or different $(C_1-C_6)$alkyl substituents; cyclohexene; heteroaryl, aryl optionally substituted by one or more identical or different radicals chosen from: $-(CH_2)_{s''}-V_4-Y_4$, halo and nitro;
$V_4$ represents $-O-$, $-S-$, $-NH-C(O)-$, $-NV_4'-$ or a covalent bond;
$Y_4$ represents a hydrogen atom or a $(C_1-C_6)$alkyl radical optionally substituted by one or more identical or different halo radicals;
$V_4'$ represents a hydrogen atom or a $(C_1-C_6)$alkyl;
s" represents an integer from 0 to 4;
or $Z_4$ represents a radical of formula

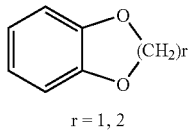

r = 1, 2 s and s' represent, independently, an integer from 0 to 6;

or a pharmaceutically acceptable salt thereof.

Preferably, the invention relates to compounds of formula II as defined above and in which $R_1$ and $R_2$ represent, independently, the hydrogen atom, a $(C_1-C_8)$alkyl radical, a bicycloalkyl or a radical of formula —$(CH_2)_n$—$X_1$ or —X—$(CH_2)_n$—$X'_1$;

X represents —C(O)— or —C(S)—NH—;

$X_1$ represents a $(C_1-C_6)$alkoxy, $(C_3-C_7)$cycloalkyl or heteroaryl radical;

$X'_1$ represents the hydrogen atom, a $(C_1-C_6)$alkyl radical optionally substituted by one or more identical or different halo radicals, $(C_3-C_7)$cycloalkyl or aryl radical;

or $R_1$ and $R_2$ form together, with the nitrogen atom to which they are attached, a heterobicycloalkyl or a heterocycloalkyl optionally substituted by one or more identical or different substituents chosen from: $(C_1-C_6)$alkyl, $(C_1-C_6)$alkoxy-carbonyl and —$(CH_2)_{n''}$-A;

A represents an aryl radical optionally substituted by one or more identical or different substituents chosen from: halo and $(C_1-C_6)$alkyl;

n" represents an integer from 0 to 3;

$R_3$ represents —$(CH_2)_p$-$Z_3$ or —C(O)-$Z'_3$ $Z_3$ aryl optionally substituted by one or more identical or different substituents chosen from: halo, nitro and —$(CH_2)_{p'}$—$V_3$—$Y_3$;

$V_3$ represents —O—, —S—, —C(O)—, —C(O)—O—, —NH—C(O)—, —C(O)—$NR'_3$— or a covalent bond;

$Y_3$ represents the hydrogen atom or a $(C_1-C_6)$alkyl radical optionally substituted by one or more identical or different halo radicals;

or $Z_3$ represents a radical of formula

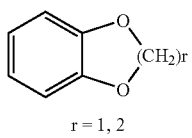

r = 1, 2

$Z'_3$ represents an aryl radical optionally substituted by one or more identical or different substituents chosen from: halo and —$(CH_2)_{p''}$—$V'_3$—$Y'_3$;

$V'_3$ represents —O— or a covalent bond;

$Y'_3$ represents the hydrogen atom or a $(C_1-C_6)$alkyl radical;

$R'_3$ represents the hydrogen atom;

p, p' and p" represent, independently, an integer from 0 to 4;

$R_4$ represents a radical of formula —$(CH_2)_s$—$R'_4$ $R'_4$ represents a heterocycloalkyl containing at least one nitrogen atom; or a radical of formula —$NW_4W'_4$ $W_4$ represents the hydrogen atom or $(C_1-C_8)$allyl;

$W'_4$ represents a radical of formula —$(CH_2)_{s'}$-$Z_4$;

$Z_4$ represents the hydrogen atom, $(C_1-C_8)$alkyl or aryl optionally substituted by one or more identical or different radicals chosen from: —$(CH_2)_{s''}$—$V_4$—$Y_4$;

$V_4$ represents —O—;

$Y_4$ represents a $(C_1-C_6)$alkyl radical optionally substituted by one or more identical or different halo radicals;

s" represents an integer from 0 to 4;

s and s' represent, independently, an integer from 0 to 6; or a pharmaceutically acceptable salt thereof, and more particularly the cycloalkyl radical is chosen from cyclopropyl and cyclohexyl; and/or the bicycloalkyl radical is bicyclo[2,2,1]heptane, and/or the heteroaryl radical is the furyl radical, and/or the aryl radical is the phenyl radical, and/or the heterobicycloalkyl is 7-aza-bicyclo[2,2,1]heptane, and/or the heterocycloalkyl is chosen from piperidine and piperazine.

Very preferentially also, the invention relates to compounds of formula II as defined above and in which $R_1$ and $R_2$ represent, independently, the hydrogen atom, a $(C_1-C_8)$alkyl radical or a radical of formula —$(CH_2)_n$—$X_1$;

$X_1$ represents a $(C_3-C_7)$cycloalkyl radical and more particularly cyclopropyl or cyclohexyl;

or $R_1$ and $R_2$ form together, with the nitrogen atom to which they are attached, a heterocycloalkyl optionally substituted by one or more identical or different $(C_1-C_6)$alkyl substituents; and/or $R_3$ represents —$(CH_2)_p$-$Z_3$ $Z_3$ represents a $(C_1-C_6)$alkoxy-carbonyl, $(C_1-C_6)$alkyl-amino-carbonyl, or phenyl radical optionally substituted by one or more identical or different substituents chosen from: nitro and —$(CH_2)_{p'}$—$V_3$—$Y_3$;

$V_3$ represents —O—, —C(O)—, —C(O)—O—, —NH—C(O)—, —C(O)—$NR'_3$—, or —NH—C(O)—$NR'_3$— or —NH—C(O)—$NR'_3$—O—;

$Y_3$ represents the hydrogen atom or a $(C_1-C_6)$alkyl radical optionally substituted by one or more identical or different halo radicals;

$R'_3$ represents the hydrogen atom;

p and p' represent, independently, an integer from 0 to 4; and/or $R_4$ represents a radical of formula —$(CH_2)_s$—$R'_4$ $R'_4$ represents a heterocycloalkyl containing at least one nitrogen atom and optionally substituted by $(C_1-C_6)$alkyl; or a radical of formula —$NW_4W'_4$ $W_4$ represents the hydrogen atom or $(C_1-C_8)$alkyl;

$W'_4$ represents a radical of formula —$(CH_2)_{s'}$-$Z_4$;

$Z_4$ represents the hydrogen atom, $(C_1-C_8)$alkyl, $(C_3-C_7)$cycloalkyl;

s and s' represent, independently, an integer from 0 to 6;

and more particularly the cycloalkyl is chosen from cyclopropyl and cyclohexyl, and/or the heterocycloalkyl is chosen from: pyrrolidine, piperidine, morpholine, piperazine; or a pharmaceutically acceptable salt thereof.

Compounds I and II of the present invention possess useful pharmacological properties. This is how it was discovered that compounds I of the present invention possess a good affinity for certain sub-types of melanocortin receptors, in particular MC4 receptors.

The compounds of the present invention can thus be used in different therapeutic applications. They can advantageously be used in order to treat the pathological states or diseases in which one or more melanocortin receptors are involved such as inflammatory states, weight disorders (obesity, cachexia, anorexia), sexual activity disorders (erective disorders), pain, but also mental disorders (anxiety, depression), drug addiction, skin diseases (acne, dermatoses, melanomas). Hereafter, in the experimental part, there is an illustration of the pharmacological properties of the compounds of the invention.

A subject of the present Application is also pharmaceutical compositions containing, as active ingredient, at least one product of formula I as defined above, as well as the pharmaceutically acceptable salts of said product of formula I, in combination with a pharmaceutically acceptable support.

By pharmaceutically acceptable salt, is meant in particular addition salts of inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. Also included in the field of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

A subject of the present Application is also the use of the compounds according to the present invention, for the preparation of a medicament for the treatment of weight disorders such as obesity, cachexia and more particularly cancer cachexia, AIDS cachexia, old age cachexia, cardiac cachexia, renal cachexia, rheumatoid arthritis cachexia, and anorexia, the treatment of pain and more particularly neuropathic pain, the treatment of mental disorders such as anxiety and depression, the treatment of sexual activity disorders such as erective disorders.

The pharmaceutical composition can be in the form of a solid, for example, powders, granules, tablets, gelatin capsules or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or the glycols, as well as their mixtures, in varying proportions, in water, added to oils or pharmaceutically acceptable fats. The sterile liquid compositions can be used for intramuscular, intraperitoneal or subcutaneous injections and the sterile compositions can also be administered by intravenous injection.

All the technical and scientific terms used in the present text have the meaning known to a person skilled in the art. Moreover, all the patents (or patent applications) as well as the other bibliographical references are incorporated by way of reference.

Experimental Part:

The compounds according to the invention obtained according to the procedures of Examples A, B, C, D and E previously described, are shown in the table below.

The compounds are characterized by their retention time (rt) and their molecular peak determined by mass spectrometry (MH+).

For the mass spectrometry, a single quadripole mass spectrometer (Micromass, Platform model) equipped with an electrospray source is used with a resolution of 0.8 Da at 50% valley. Calibration is carried out monthly between the masses 80 and 1000 Da using a calibrating mixture of sodium iodide and rubidium iodide in solution in an isopropanol/water mixture (1/1 Vol.)

For the liquid chromatography, a Waters system including an in-line degasser, a Waters 600 quaternary pump, a Gilson 233 plate sampling injector and a Waters PAD 996 UV detector, are used.

The elution conditions used are the following:

Eluent A water+0.04% trifluoroacetic acid B acetonitrile

| T (min) | A % | B % |
|---------|-----|-----|
| 1       | 95  | 5   |
| 8.5     | 5   | 95  |
| 10.5    | 5   | 95  |
| 10.6    | 95  | 5   |
| 14.9    | 95  | 5   |
| 15.0    | 95  | 5   |

Flow rate: 1 ml/min
Injection: 10 μl
Column: Uptisphere ODS 3 μm 75*4.6 mm i.d.

These examples are presented in order to illustrate the above procedures and should in no event be considered as a limit to the scope of the invention.

| Examples | Molecular structures | [M + H]+ | rt (min) |
|----------|---------------------|----------|----------|
| 1 | 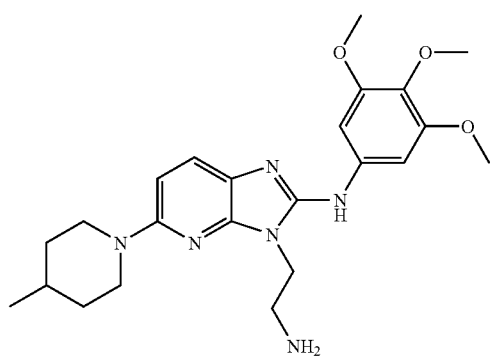 | 441.2 | 7.5 |

-continued

| Examples | Molecular structures | [M + H]+ | rt (min) |
|---|---|---|---|
| 2 | 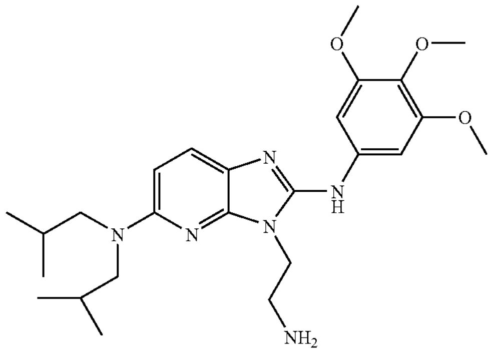 | 471.3 | 8.0 |
| 3 | 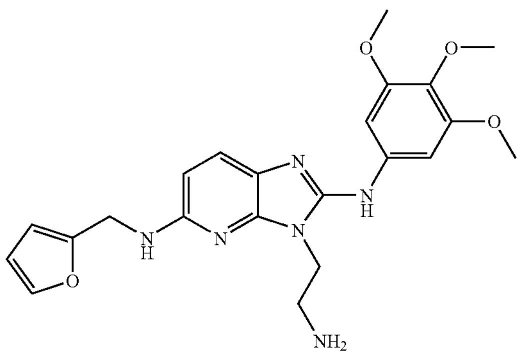 | 439.2 | 7.3 |
| 4 | 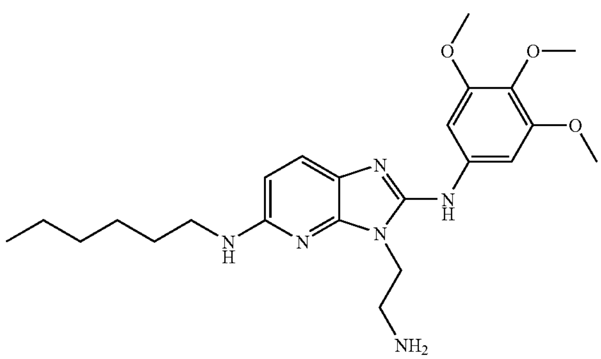 | 443.2 | 7.8 |
| 5 | 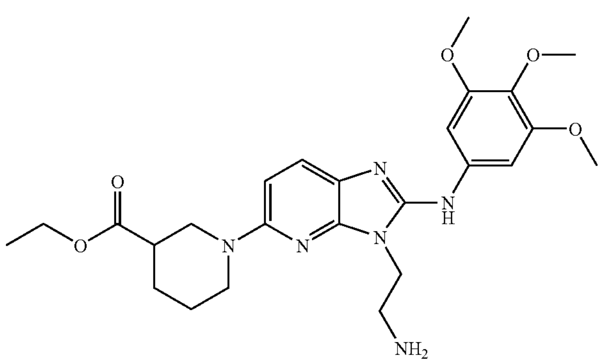 | 499.2 | 7.5 |

| Examples | Molecular structures | [M + H]+ | rt (min) |
|---|---|---|---|
| 6 | 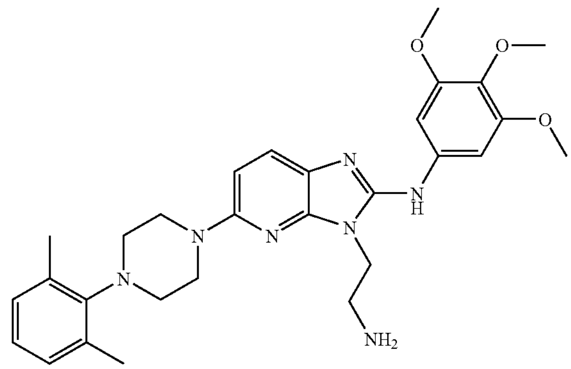 | 532.3 | 8.2 |
| 7 | 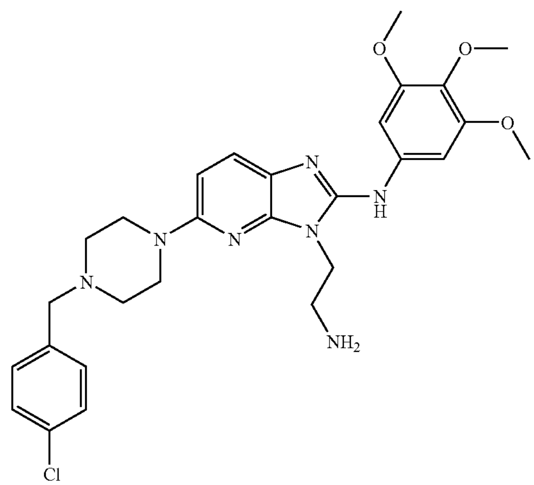 | 552.2 | 7.2 |
| 8 | 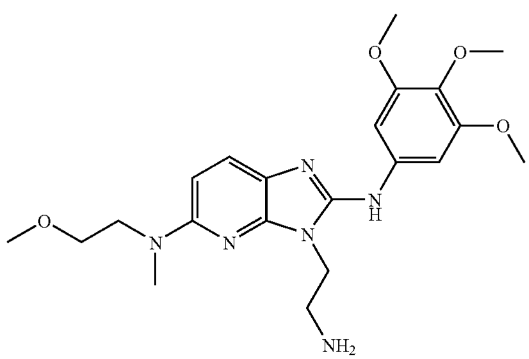 | 417.1 | 7.0 |
| 9 | 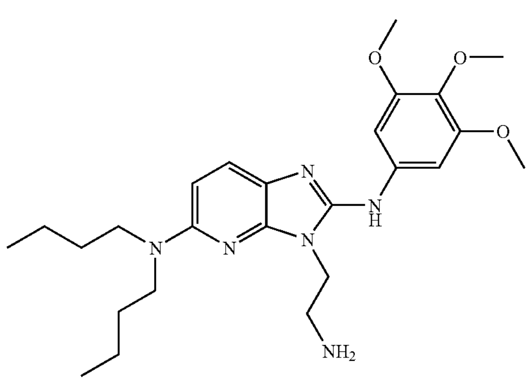 | 471.3 | 8.0 |

-continued
| Examples | Molecular structures | [M + H]+ | rt (min) |
|---|---|---|---|
| 10 | 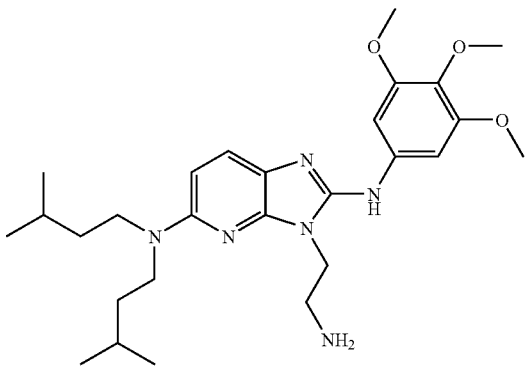 | 499.3 | 8.4 |
| 11 | 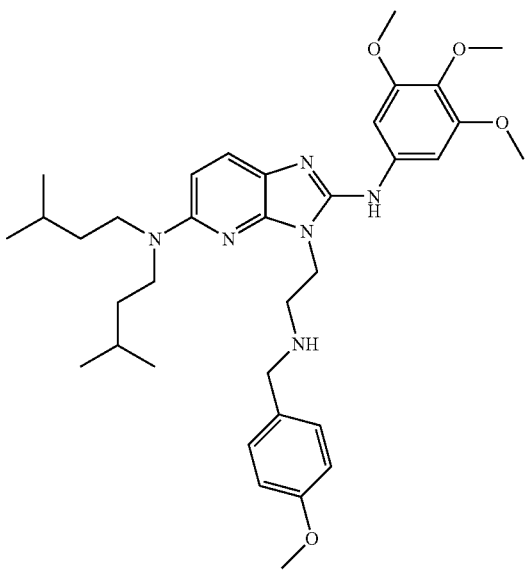 | 619.4 | 8.9 |
| 12 | 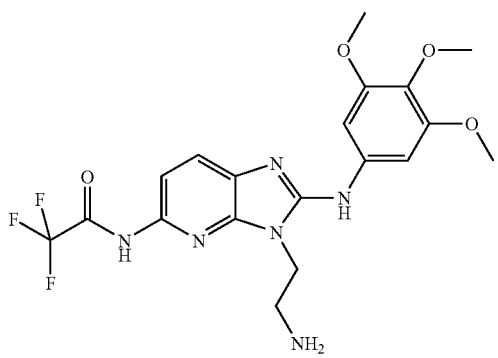 | 455.1 | 7.5 |

-continued

| Examples | Molecular structures | [M + H]+ | rt (min) |
|---|---|---|---|
| 13 | 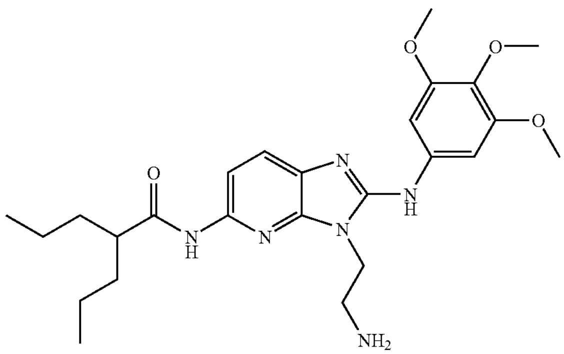 | 485.2 | 7.8 |
| 14 | 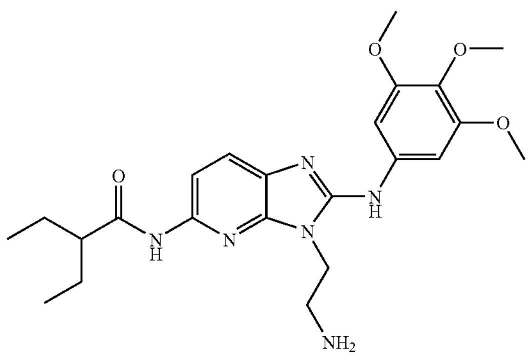 | 457.2 | 7.5 |
| 15 | 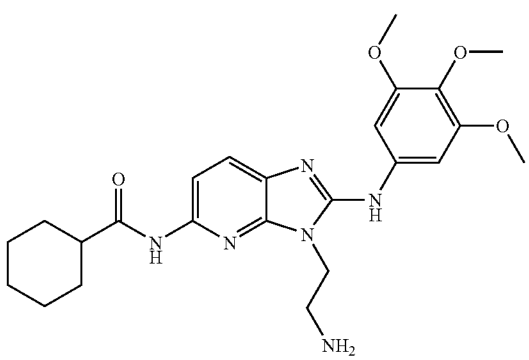 | 469.2 | 7.6 |
| 16 | 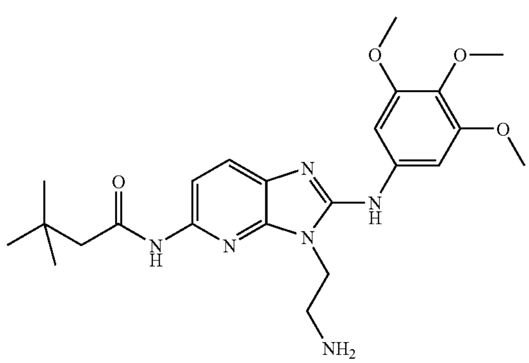 | 457.3 | 7.5 |

-continued

| Examples | Molecular structures | [M + H]+ | rt (min) |
|---|---|---|---|
| 17 | 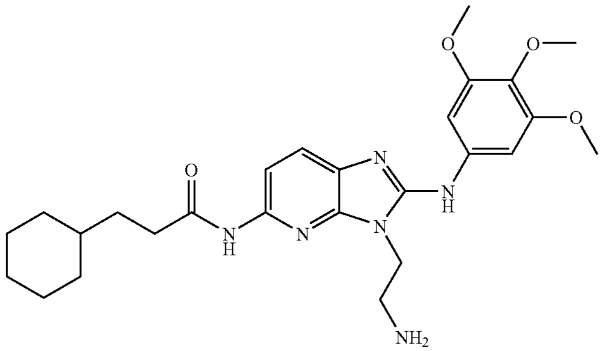 | 497.3 | 8.0 |
| 18 | 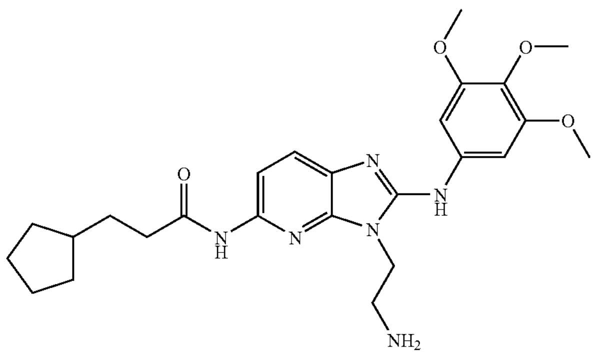 | 483.3 | 7.8 |
| 19 | 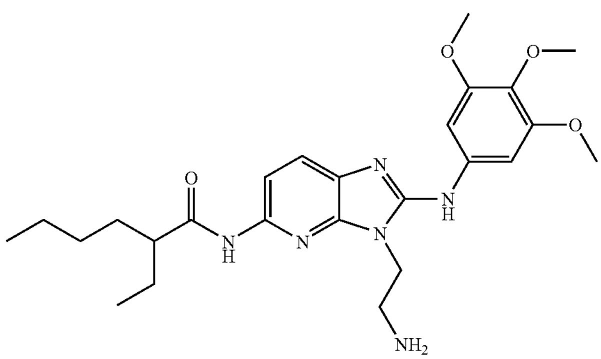 | 485.3 | 7.8 |
| 20 | 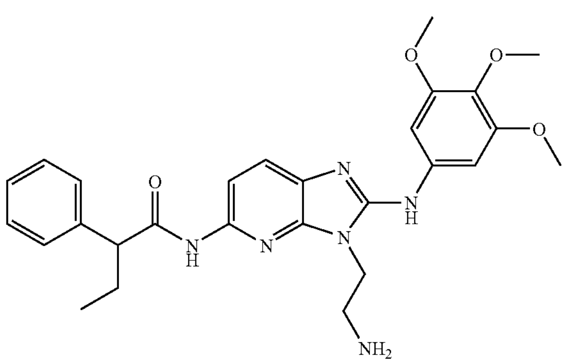 | 505.2 | 7.8 |

-continued

| Examples | Molecular structures | [M + H]+ | rt (min) |
|---|---|---|---|
| 21 | 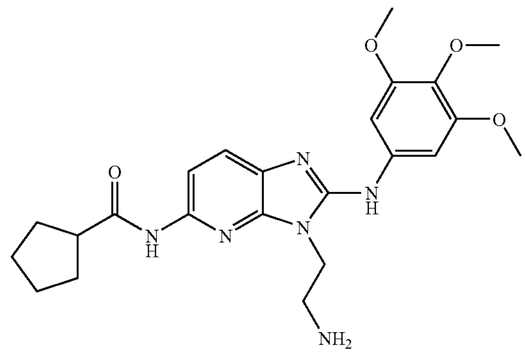 | 455.2 | 7.5 |
| 22 | 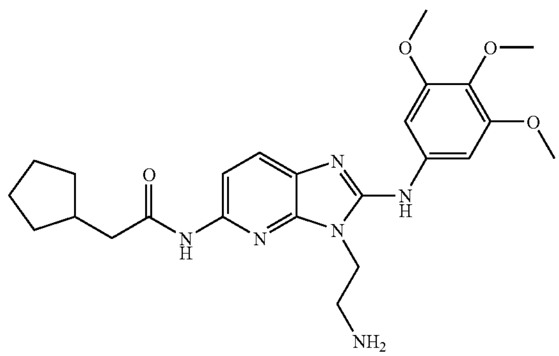 | 469.2 | 7.6 |
| 23 | 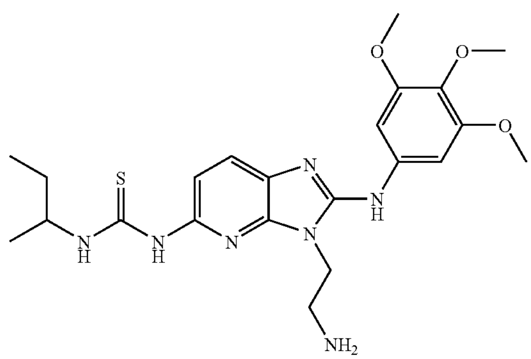 | 474.2 | 7.6 |
| 24 | 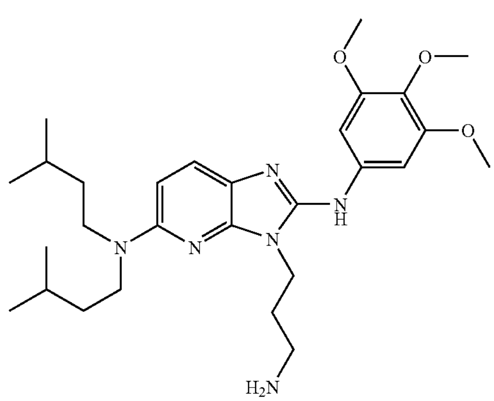 | 513.3 | 8.5 |

| Examples | Molecular structures | [M + H]+ | rt (min) |
|---|---|---|---|
| 25 | 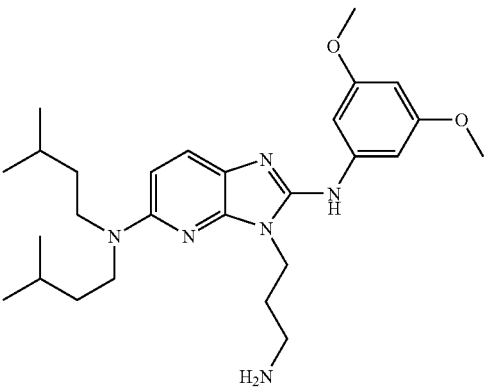 | 483.3 | 8.6 |
| 26 | 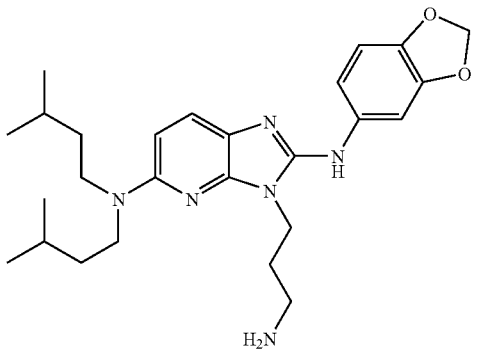 | 467.3 | 8.4 |
| 27 | 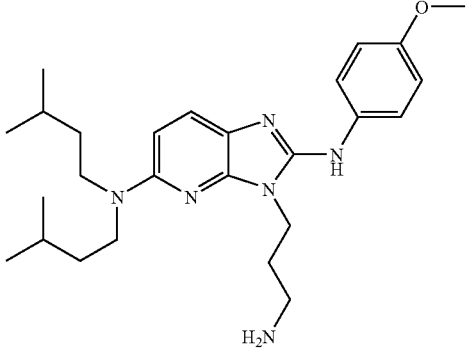 | 453.3 | 8.5 |
| 28 | 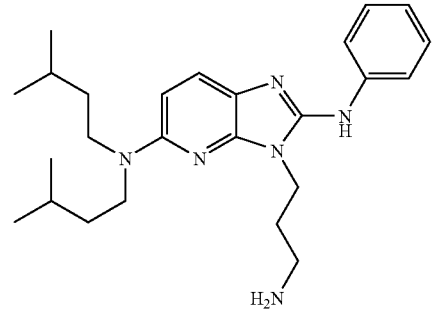 | 423.3 | 8.5 |

-continued

| Examples | Molecular structures | [M + H]+ | rt (min) |
|---|---|---|---|
| 29 | 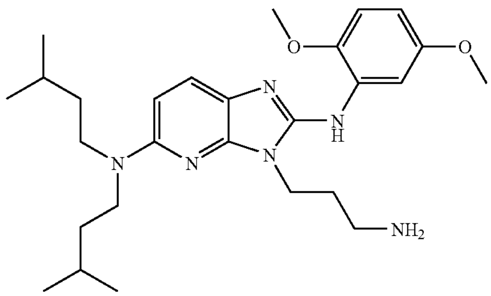 | 483.3 | 8.6 |
| 30 | 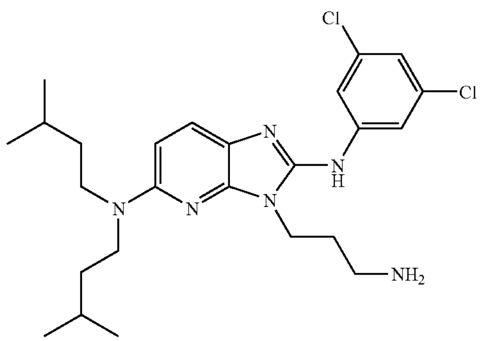 | 491.2 | 9.4 |
| 31 | 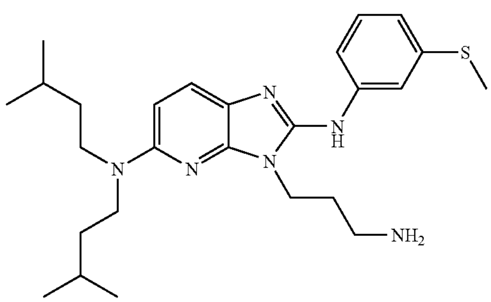 | 469.3 | 8.7 |
| 32 | 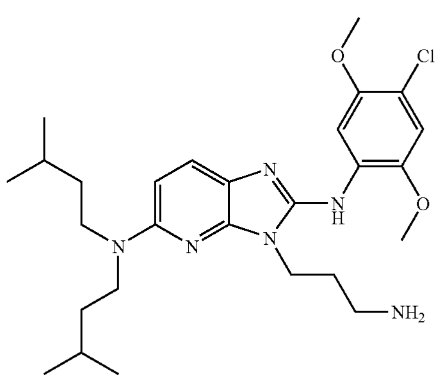 | 517.3 | 8.7 |

-continued

| Examples | Molecular structures | [M + H]+ | rt (min) |
|---|---|---|---|
| 33 | 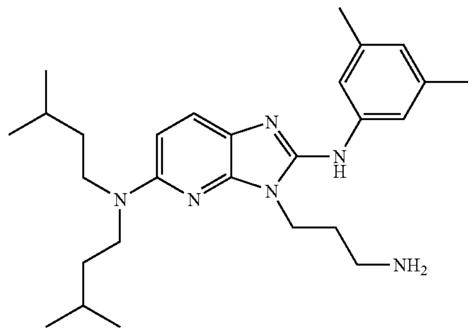 | 453.3 | 8.5 |
| 34 | 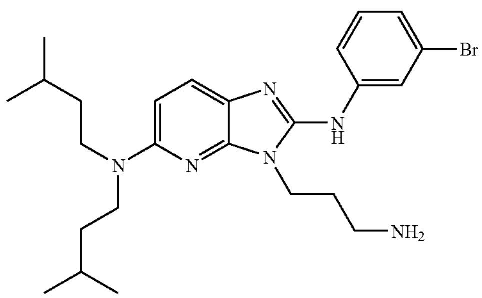 | 501.2 | 8.8 |
| 35 | 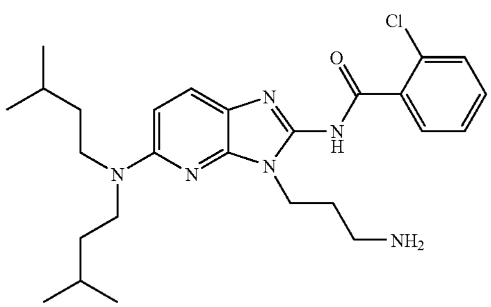 | 485.2 | 10.2 |
| 36 | 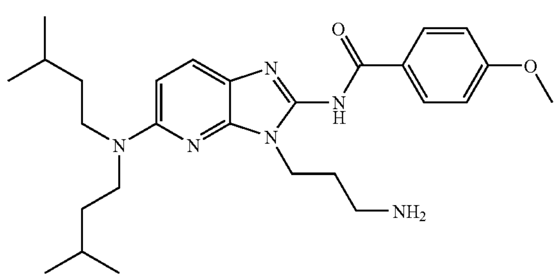 | 465.3 | 10.5 |
| 37 | 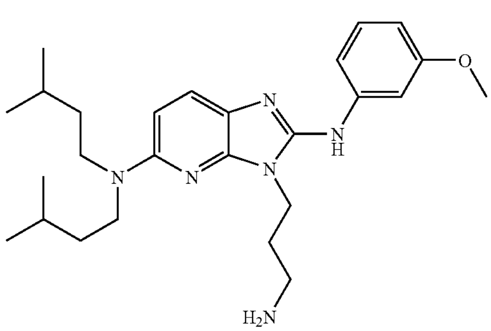 | 453.2 | 8.5 |

-continued

| Examples | Molecular structures | [M + H]+ | rt (min) |
|---|---|---|---|
| 38 | 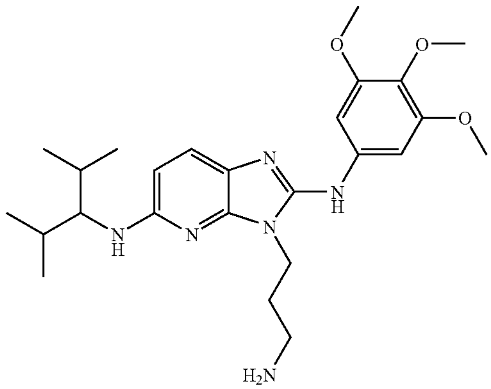 | 471.3 | 7.3 |
| 39 | 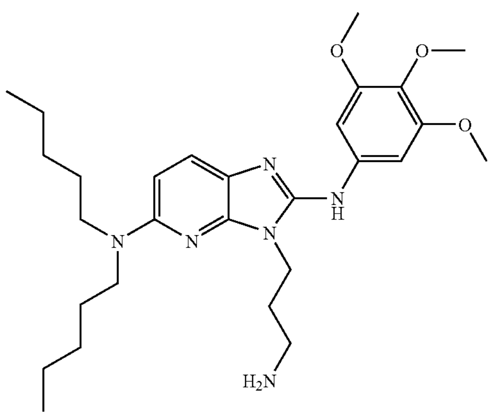 | 513.3 | 7.8 |
| 40 | 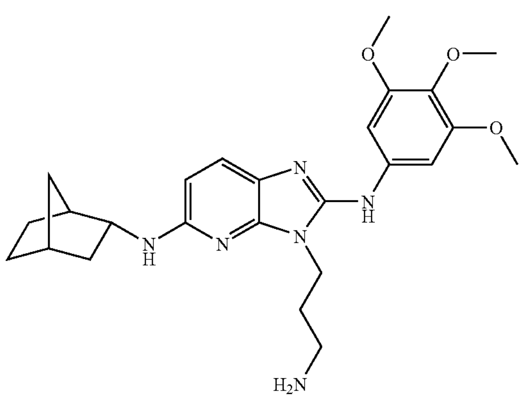 | 467.3 | 7.2 |

-continued

| Examples | Molecular structures | [M + H]+ | rt (min) |
|---|---|---|---|
| 41 | 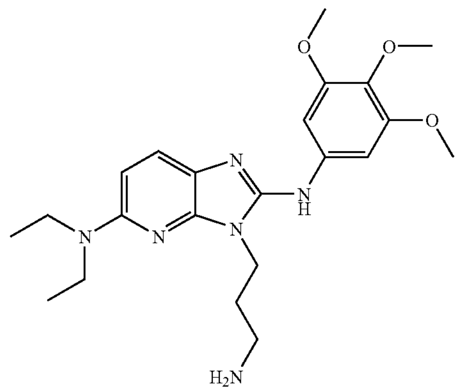 | 429.2 | 7.0 |
| 42 | 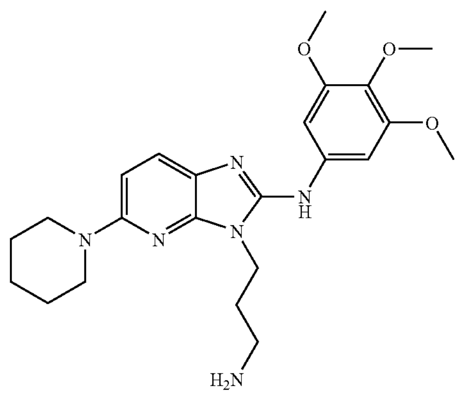 | 441.2 | 7.0 |
| 43 | 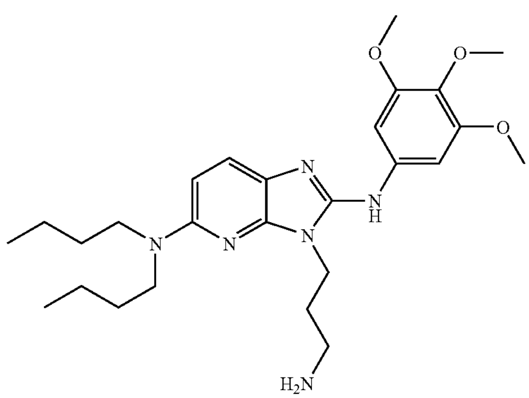 | 485.3 | 7.5 |
| 44 | 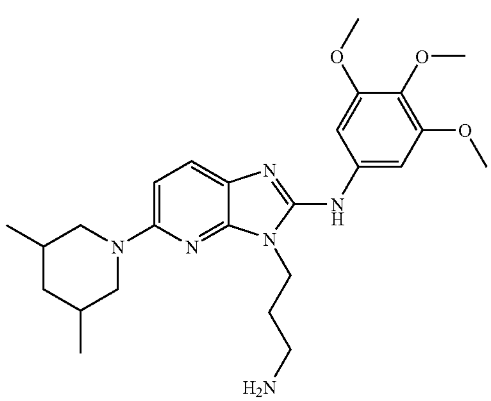 | 469.3 | 7.3 |

| Examples | Molecular structures | [M + H]+ | rt (min) |
|---|---|---|---|
| 45 | 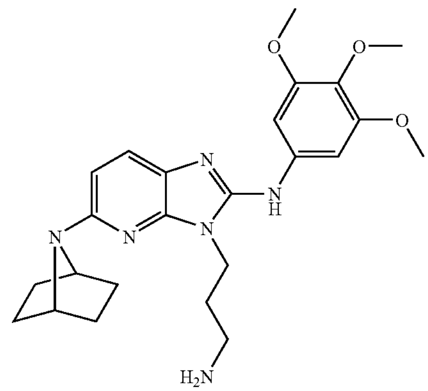 | 453.2 | 7.0 |
| 46 | 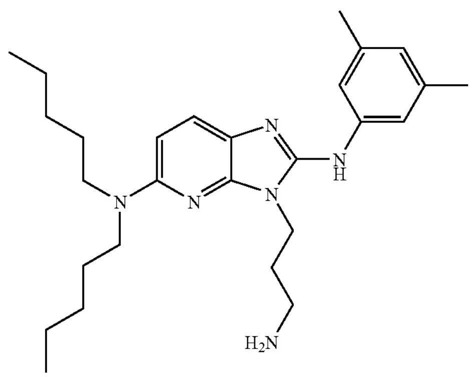 | 451.3 | 8.0 |
| 47 | 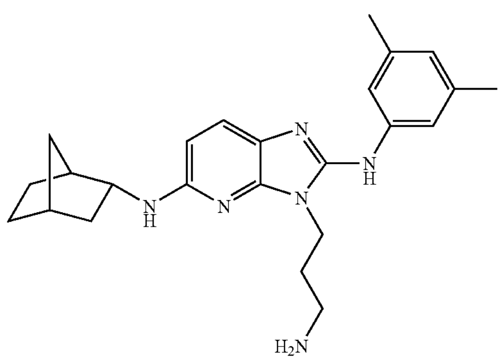 | 405.2 | 7.4 |
| 48 | 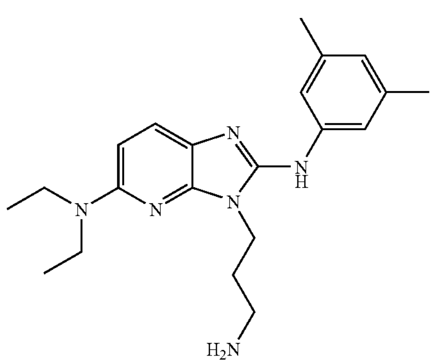 | 367.2 | 7.2 |

-continued

| Examples | Molecular structures | [M + H]+ | rt (min) |
|---|---|---|---|
| 49 | 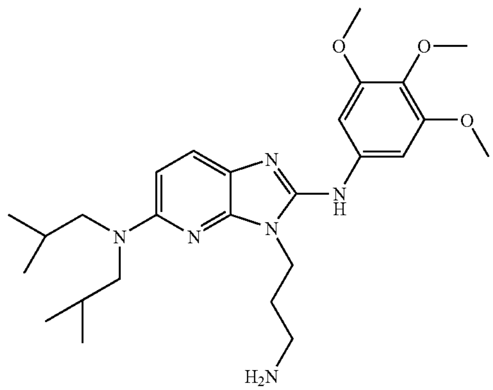 | 485.2 | 7.5 |
| 50 | 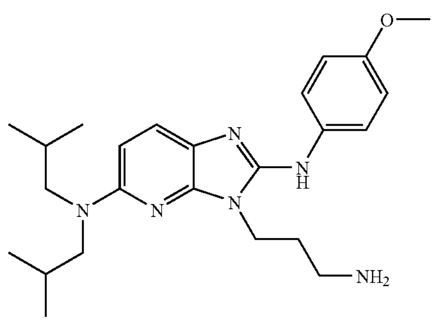 | 425.3 | 8.2 |
| 51 | 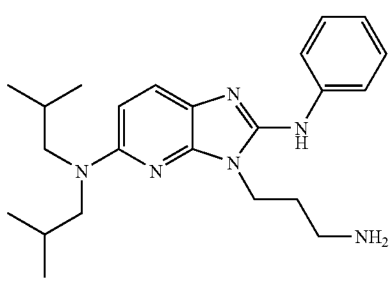 | 395.3 | 8.0 |
| 52 | 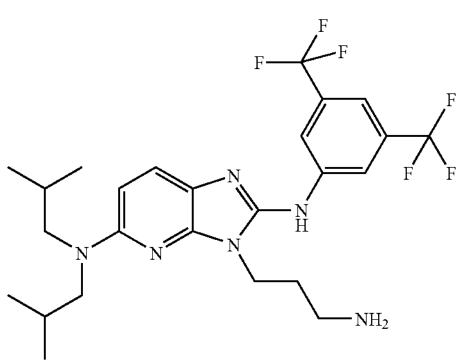 | 531.2 | 9.6 |

| Examples | Molecular structures | [M + H]+ | rt (min) |
|---|---|---|---|
| 53 | 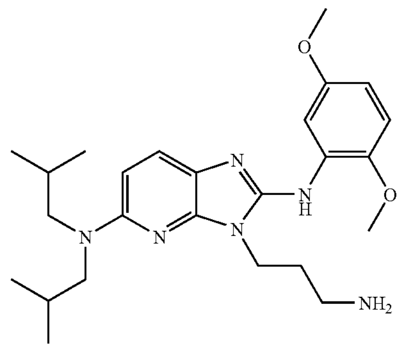 | 455.3 | 8.2 |
| 54 | 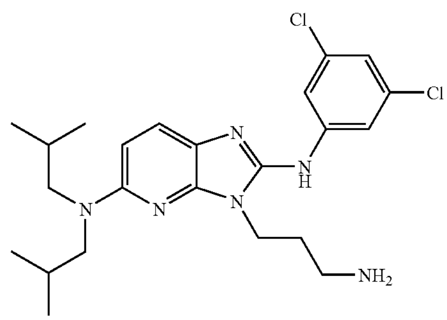 | 463.2 | 8.8 |
| 55 | 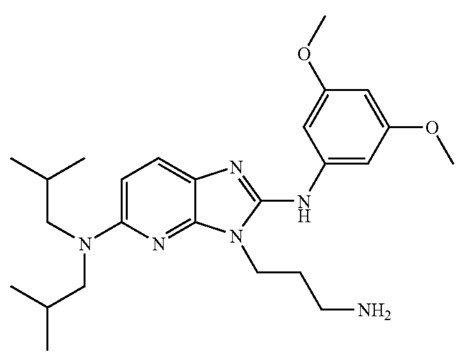 | 455.3 | 8.2 |
| 56 | 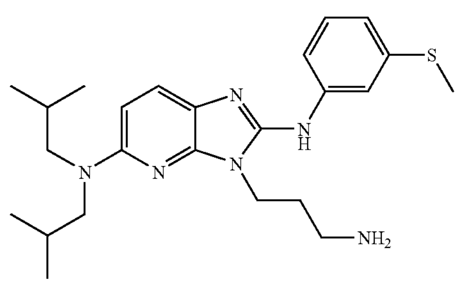 | 441.3 | 8.2 |

-continued

| Examples | Molecular structures | [M + H]+ | rt (min) |
|----------|---------------------|----------|----------|
| 57 | 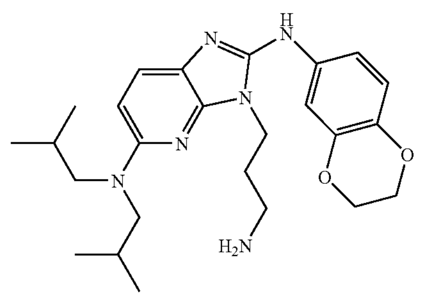 | 453.3 | 8.1 |
| 58 | 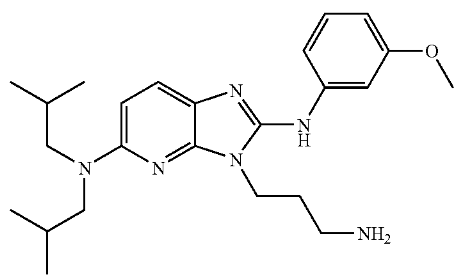 | 425.3 | 8.1 |
| 59 | 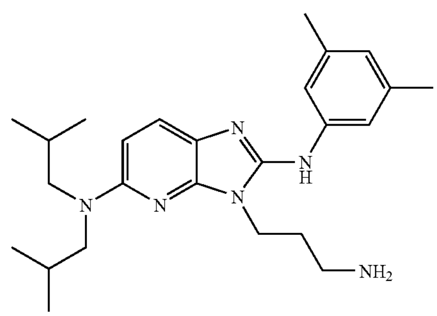 | 423.3 | 8.3 |
| 60 | 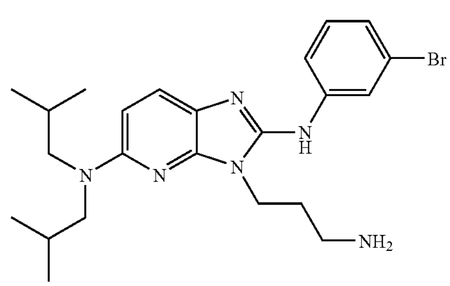 | 473.2 | 8.3 |
| 61 | 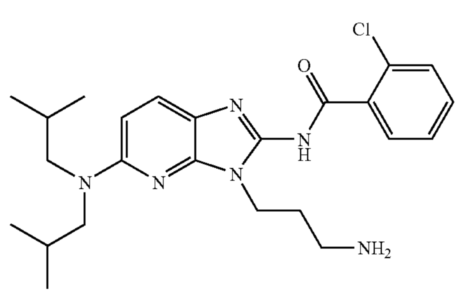 | 457.2 | 9.4 |

-continued

| Examples | Molecular structures | [M + H]+ | rt (min) |
|---|---|---|---|
| 62 | 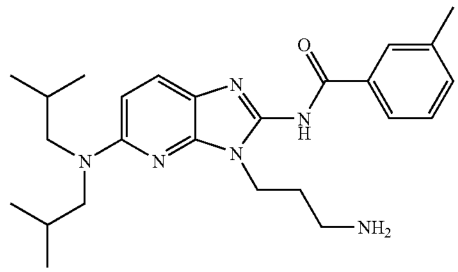 | 437.2 | 9.8 |
| 63 | 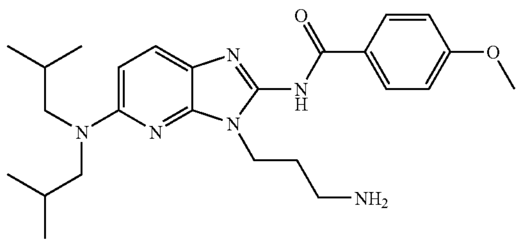 | 453.3 | 9.6 |
| 64 | 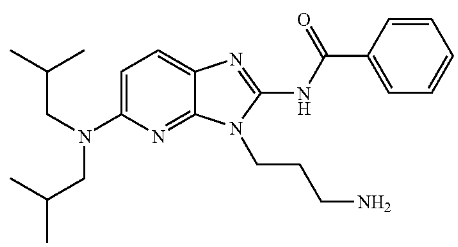 | 423.2 | 9.6 |
| 65 | 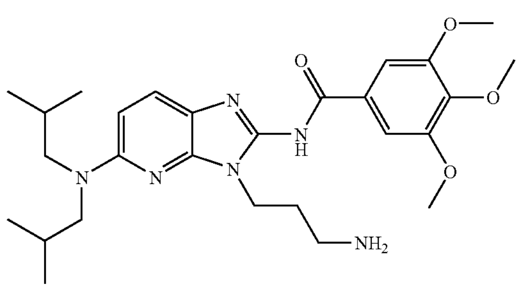 | 513.3 | 9.6 |
| 66 | 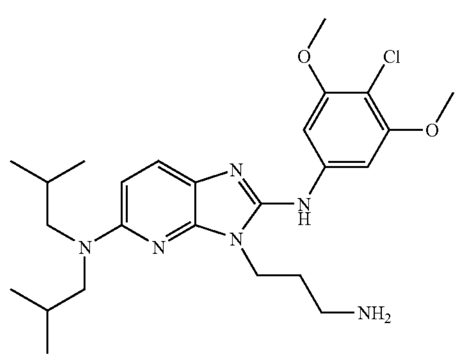 | 489.2 | 8.4 |

-continued

| Examples | Molecular structures | [M + H]+ | rt (min) |
|---|---|---|---|
| 67 | 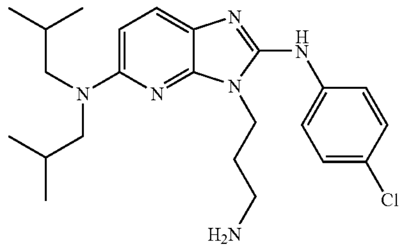 | 429.2 | 8.2 |
| 68 | 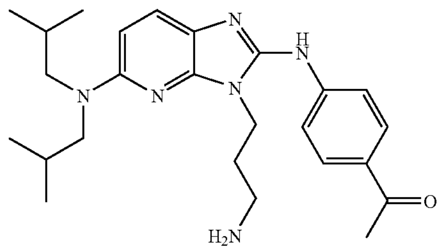 | 437.3 | 8.1 |
| 69 | 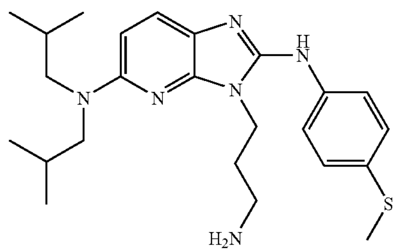 | 441.2 | 8.2 |
| 70 | 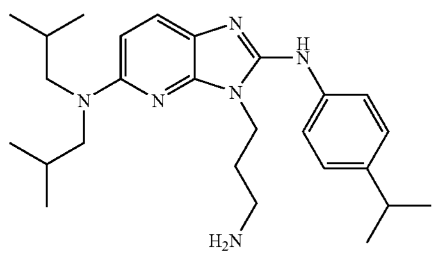 | 437.2 | 8.4 |
| 71 | 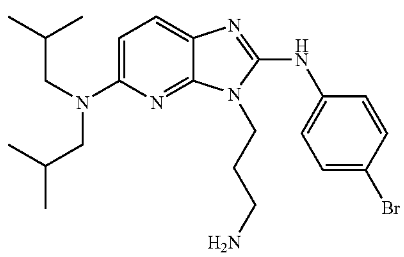 | 473.1 | 8.3 |
| 72 | 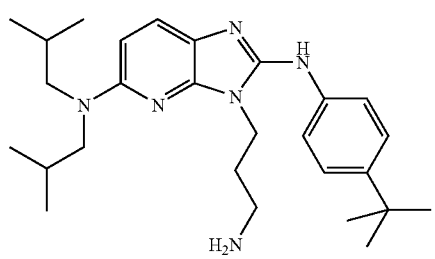 | 451.2 | 8.5 |

| Examples | Molecular structures | [M + H]+ | rt (min) |
|---|---|---|---|
| 73 | 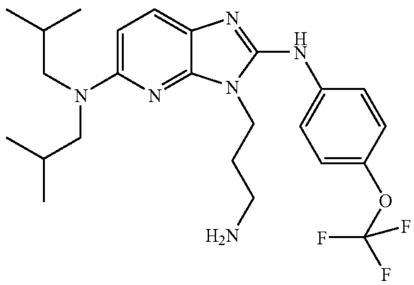 | 479.2 | 8.4 |
| 74 | 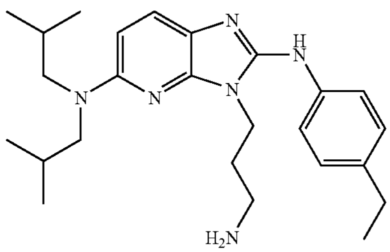 | 423.3 | 8.3 |
| 75 | 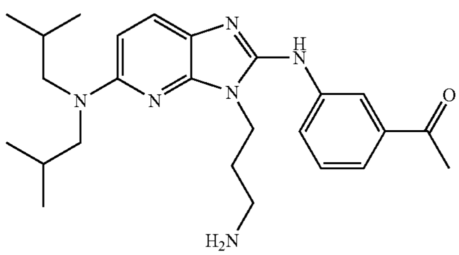 | 437.2 | 8.0 |
| 76 | 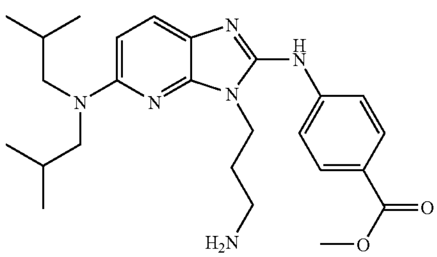 | 453.2 | 8.2 |
| 77 | 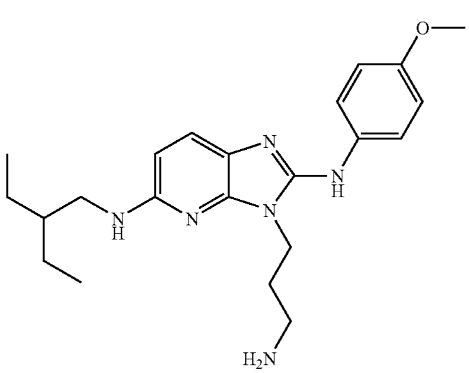 | 397.1 | 7.8 |

-continued

| Examples | Molecular structures | [M + H]+ | rt (min) |
|---|---|---|---|
| 78 | 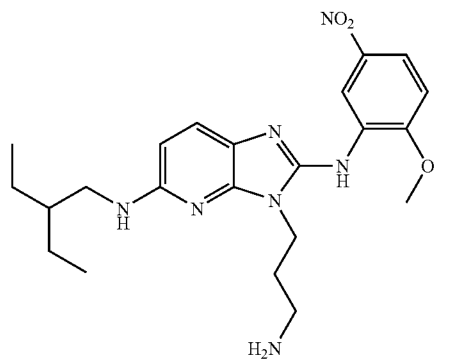 | 442.1 | 7.9 |
| 79 | 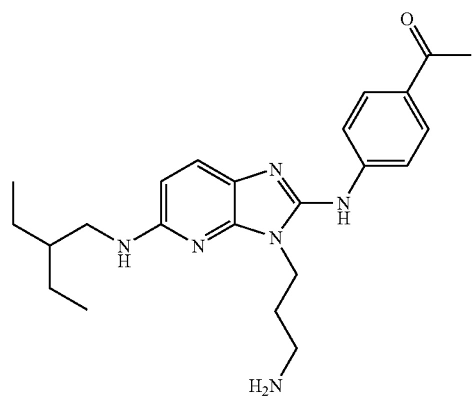 | 409.0 | 7.8 |
| 80 | 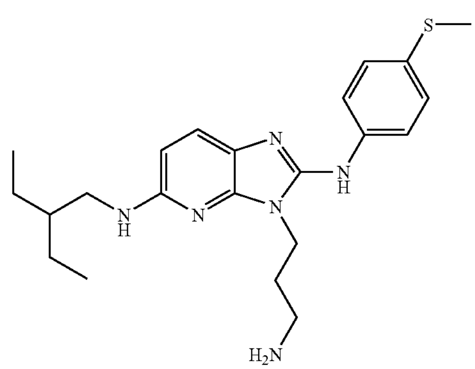 | 413.0 | 7.9 |
| 81 | 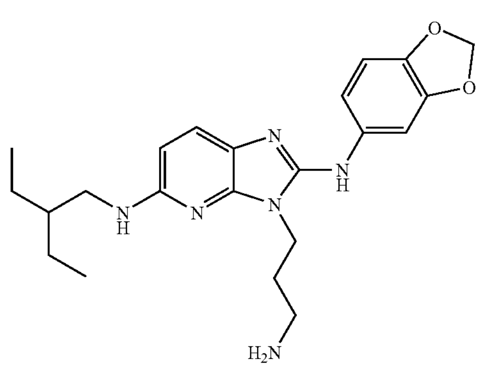 | 411.0 | 7.8 |

-continued

| Examples | Molecular structures | [M + H]+ | rt (min) |
|---|---|---|---|
| 82 | 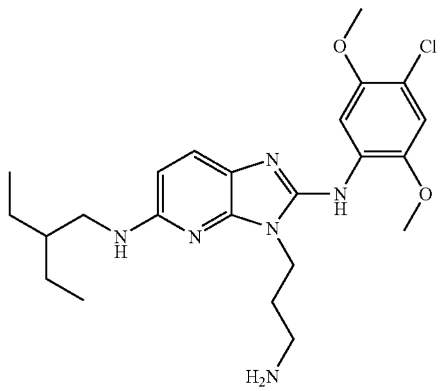 | 461.0 | 7.9 |
| 83 | 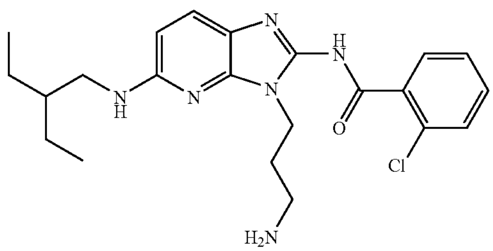 | 429.0 | 8.7 |
| 84 | 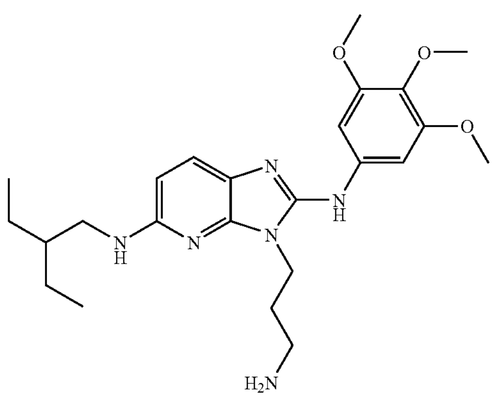 | 457.1 | 7.8 |
| 85 | 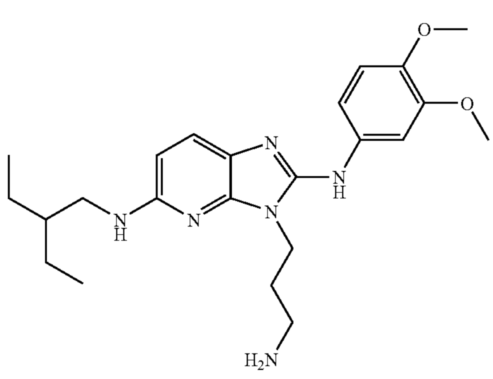 | 427.1 | 7.7 |

-continued

| Examples | Molecular structures | [M + H]+ | rt (min) |
| --- | --- | --- | --- |
| 86 | 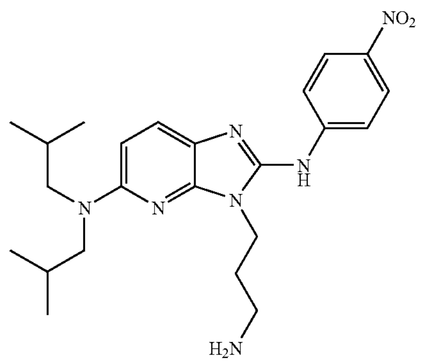 | 440.0 | 8.7 |
| 87 | 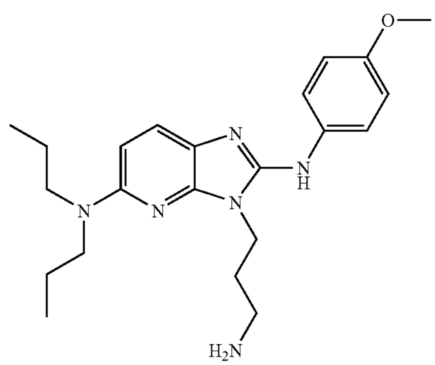 | 397.1 | 7.8 |
| 88 | 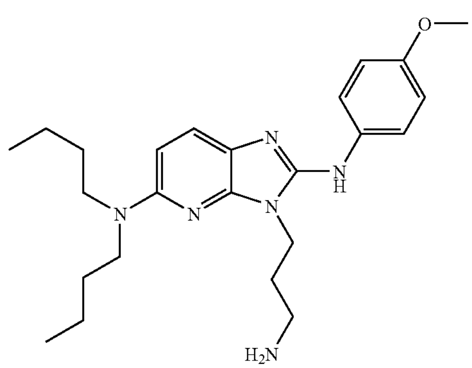 | 425.1 | 8.2 |
| 89 | 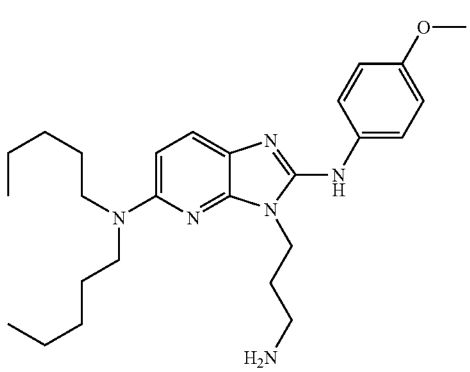 | 453.1 | 8.5 |

-continued

| Examples | Molecular structures | [M + H]+ | rt (min) |
|---|---|---|---|
| 90 | 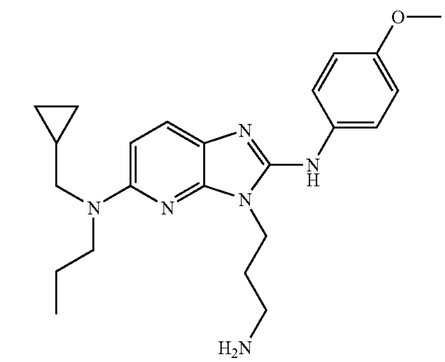 | 409.2 | 7.8 |
| 91 | 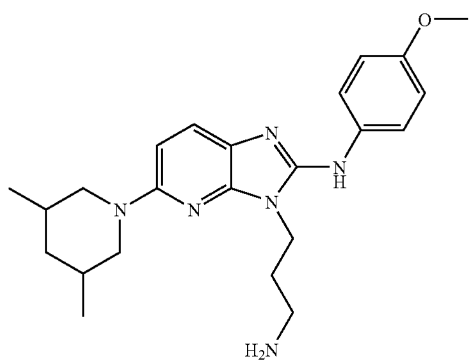 | 409.2 | 7.8 |
| 92 | 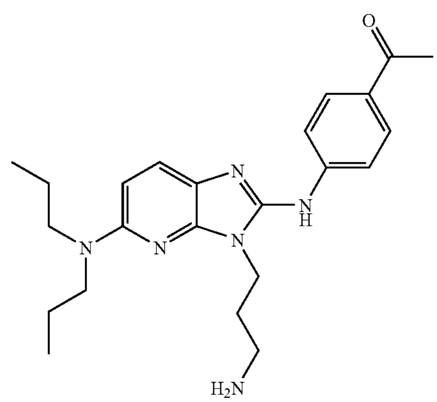 | 409.0 | 7.8 |
| 93 | 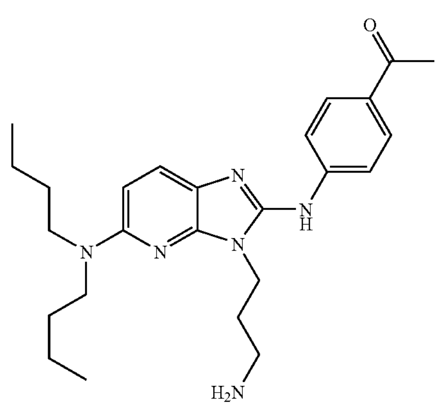 | 437.0 | 8.1 |

-continued

| Examples | Molecular structures | [M + H]+ | rt (min) |
|---|---|---|---|
| 94 | 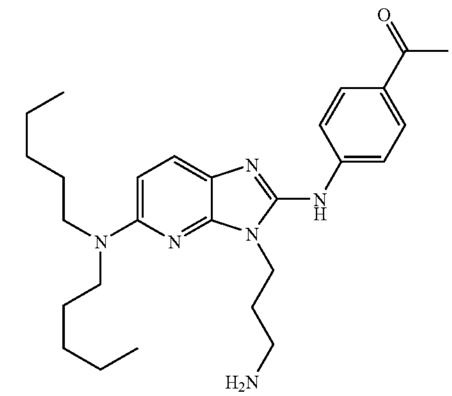 | 465.2 | 8.5 |
| 95 | 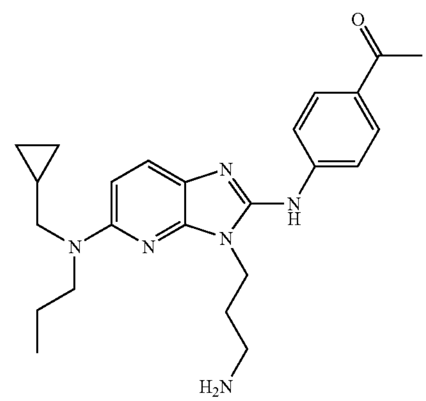 | 421.0 | 7.8 |
| 96 | 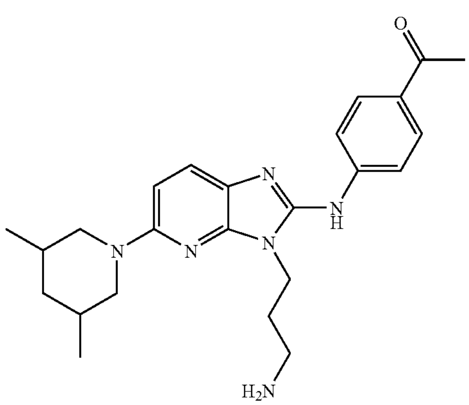 | 421.2 | 7.8 |

-continued

| Examples | Molecular structures | [M + H]+ | rt (min) |
|---|---|---|---|
| 97 | 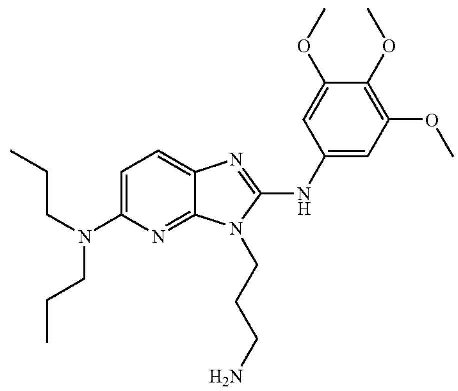 | 457.1 | 7.8 |
| 98 | 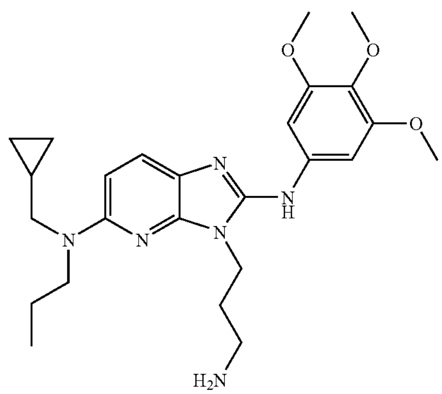 | 469.1 | 7.8 |
| 99 | 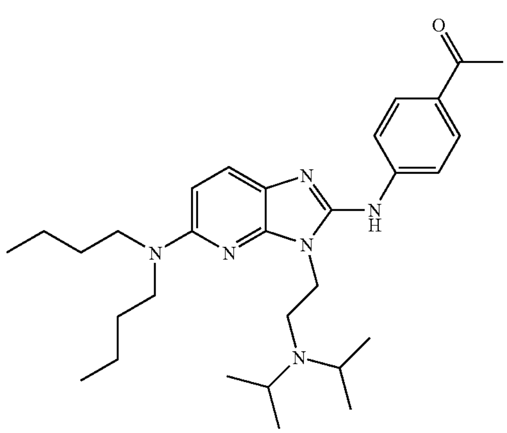 | 507.3 | 9.1 |

-continued

| Examples | Molecular structures | [M + H]+ | rt (min) |
|---|---|---|---|
| 100 | 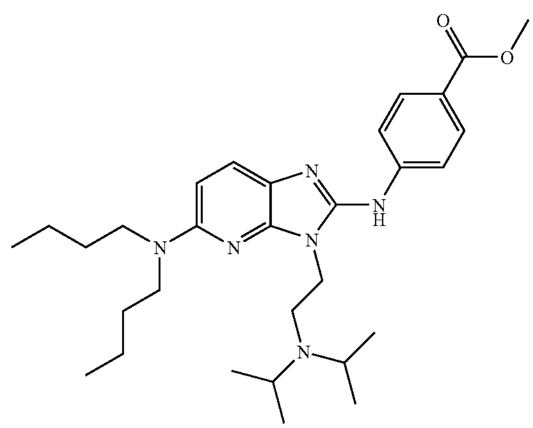 | 523.3 | 9.3 |
| 101 | 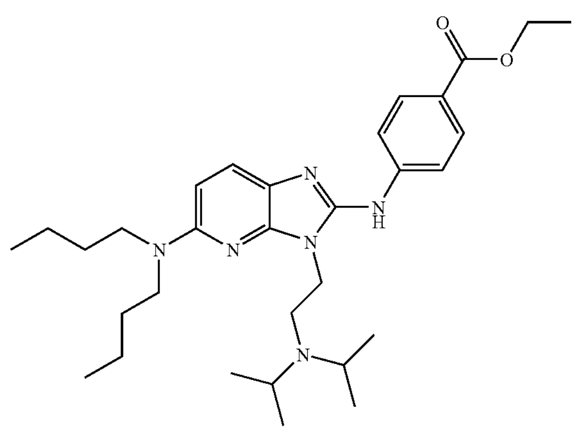 | 537.3 | 9.5 |
| 102 | 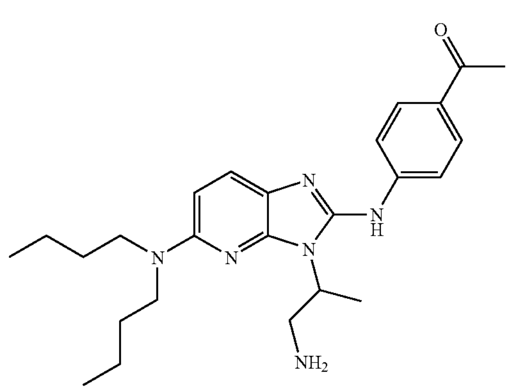 | 437.2 | 8.4 |

| Examples | Molecular structures | [M + H]+ | rt (min) |
|---|---|---|---|
| 103 | 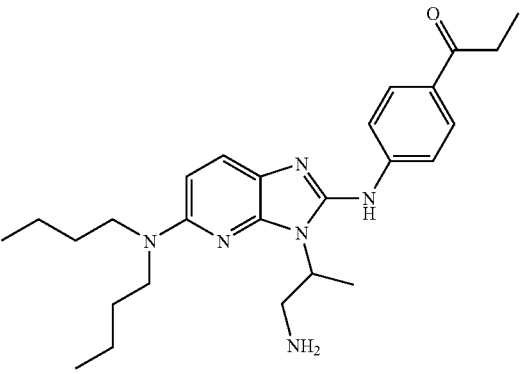 | 451.3 | 8.6 |
| 104 | 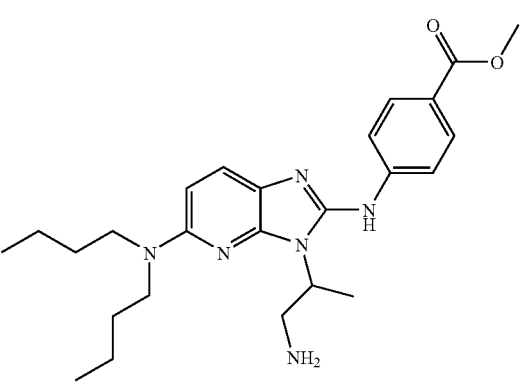 | 453.3 | 8.6 |
| 105 | 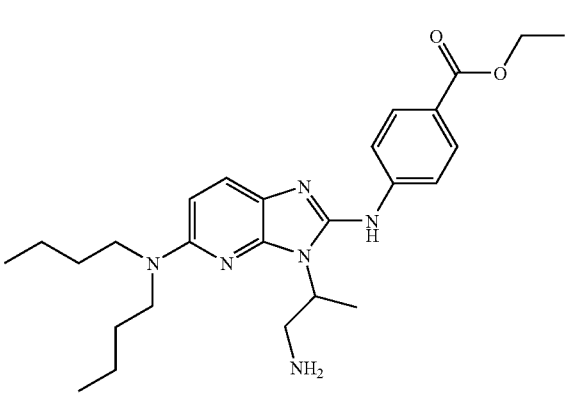 | 467.3 | 8.8 |
| 106 | 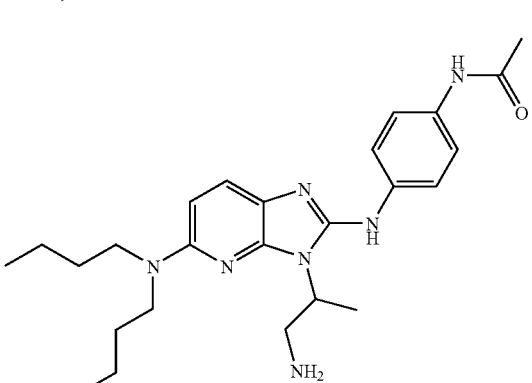 | 452.3 | 8.0 |

-continued

| Examples | Molecular structures | [M + H]+ | rt (min) |
|---|---|---|---|
| 107 | 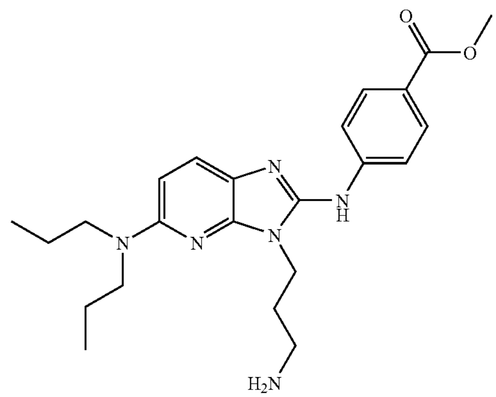 | 425.2 | 7.9 |
| 108 | 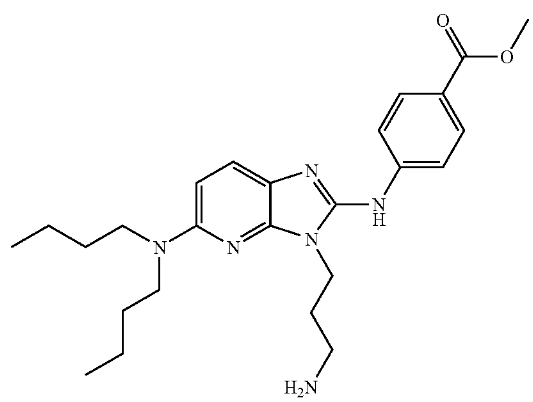 | 453.3 | 8.2 |
| 109 | 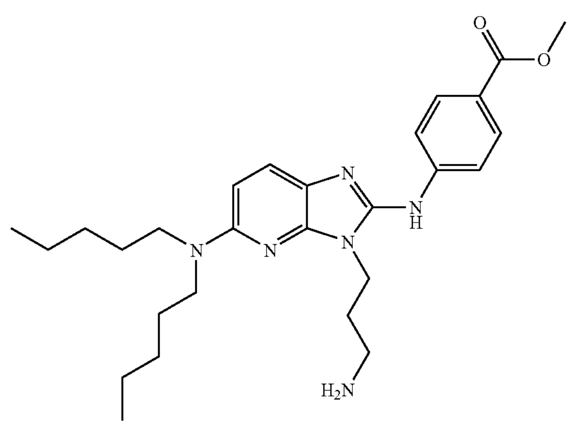 | 481.3 | 8.7 |

-continued

| Examples | Molecular structures | [M + H]+ | rt (min) |
|---|---|---|---|
| 110 | 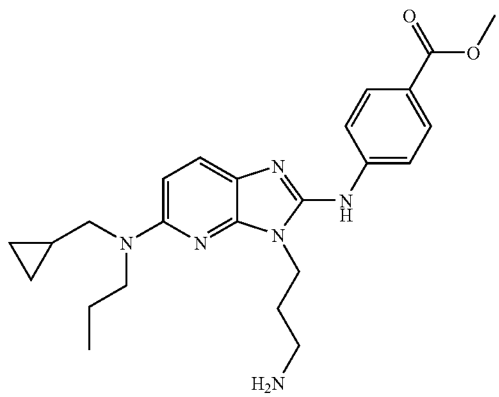 | 437.2 | 7.9 |
| 111 | 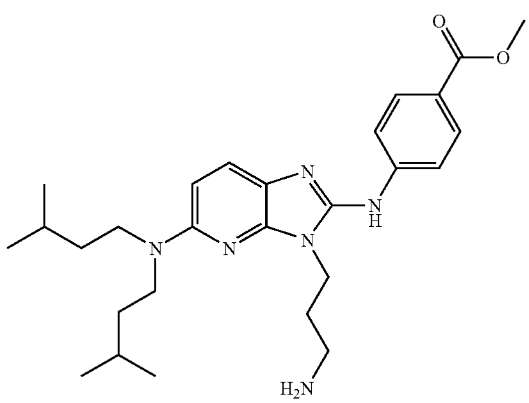 | 481.3 | 8.6 |
| 112 | 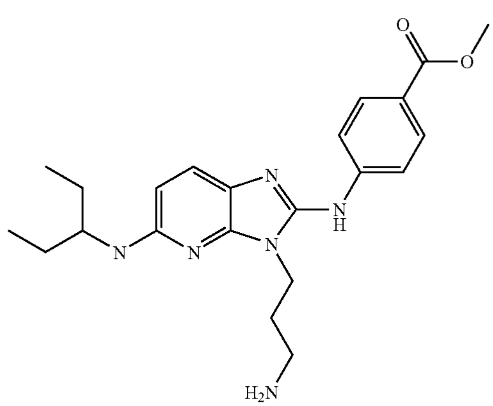 | 411.2 | 7.7 |

-continued
| Examples | Molecular structures | [M + H]+ | rt (min) |
|---|---|---|---|
| 113 | 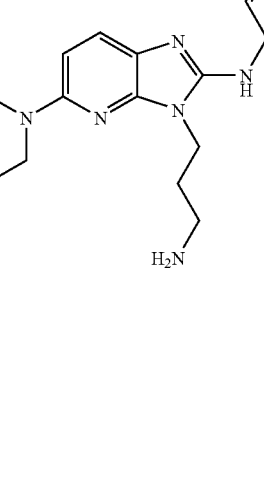 | 437.2 | 8.0 |
| 114 | 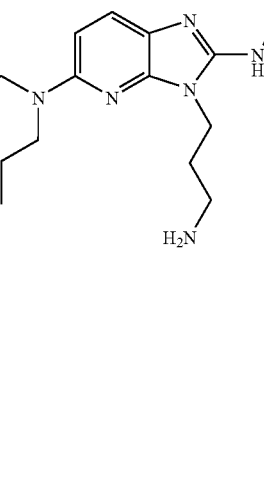 | 423.2 | 8.3 |
| 115 | 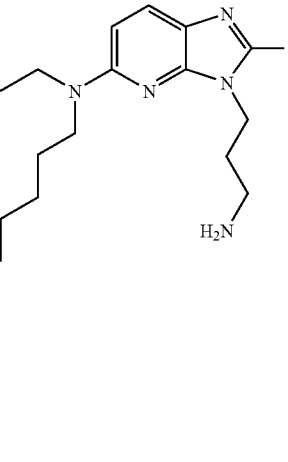 | 479.3 | 9.0 |

-continued
| Examples | Molecular structures | [M + H]+ | rt (min) |
|---|---|---|---|
| 116 | 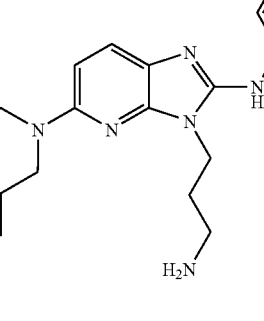 | 435.2 | 8.3 |
| 117 | 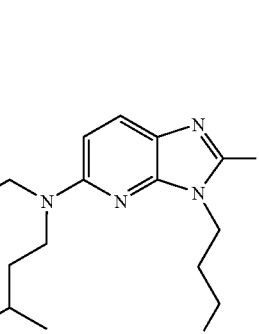 | 479.3 | 8.9 |
| 118 | 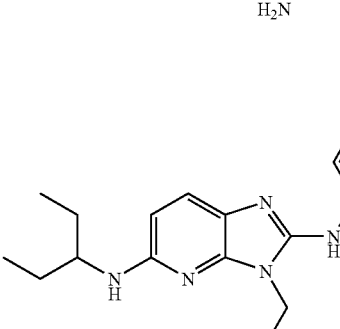 | 409.2 | 8.1 |
| 119 | 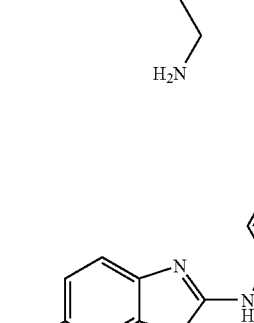 | 435.2 | 8.3 |

-continued
| Examples | Molecular structures | [M + H]+ | rt (min) |
|---|---|---|---|
| 120 | 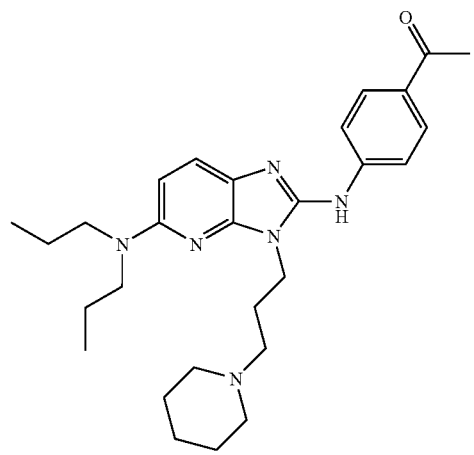 | 477.2 | 8.1 |
| 121 | 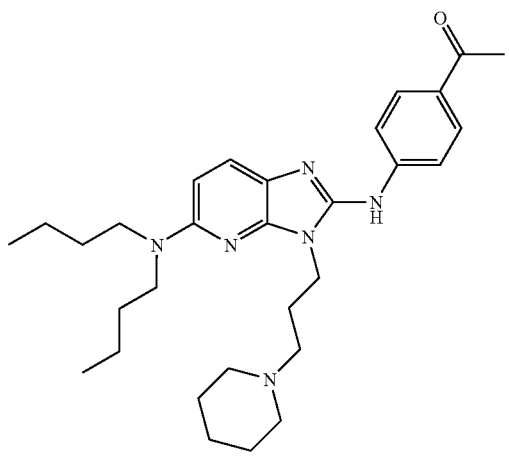 | 505.2 | 8.5 |
| 122 | 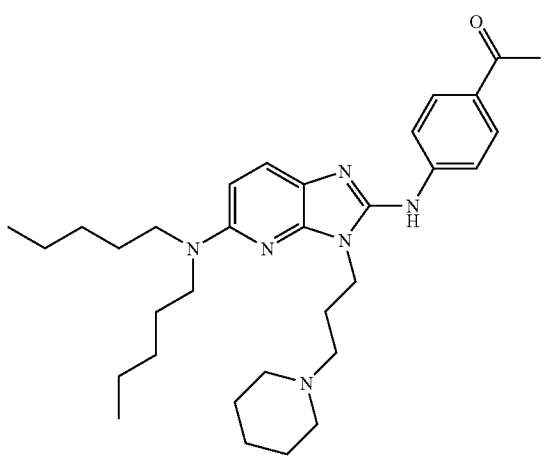 | 533.3 | 9.0 |

-continued
| Examples | Molecular structures | [M + H]+ | rt (min) |
|---|---|---|---|
| 123 | 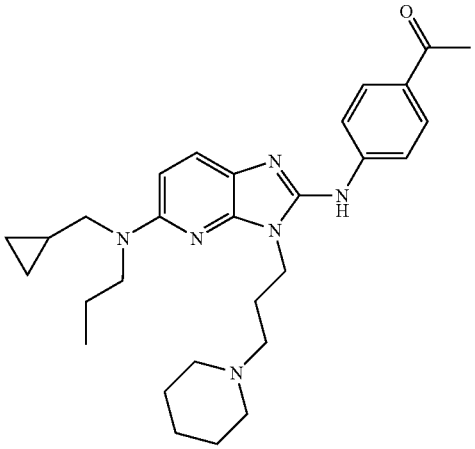 | 489.2 | 8.1 |
| 124 | 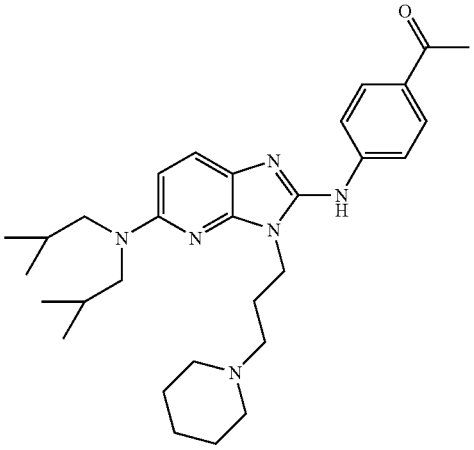 | 505.3 | 8.4 |
| 125 | 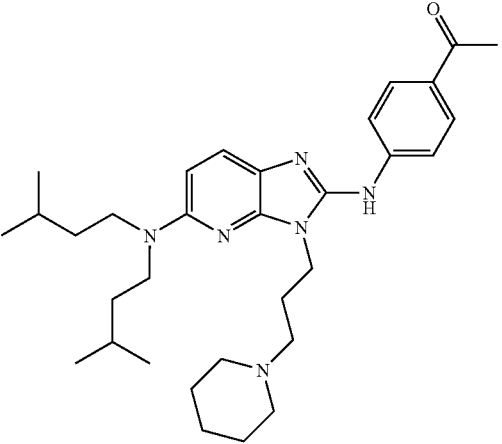 | 533.3 | 8.9 |

-continued

| Examples | Molecular structures | [M + H]+ | rt (min) |
|---|---|---|---|
| 126 | 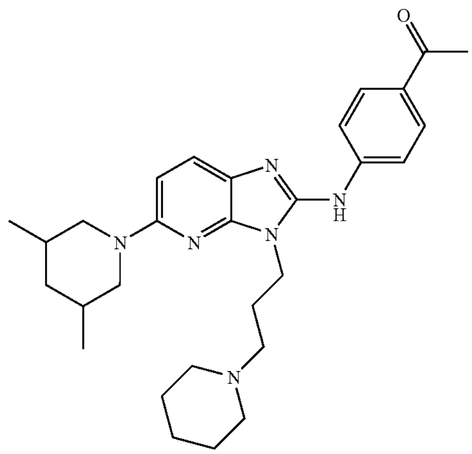 | 489.2 | 8.2 |
| 127 | 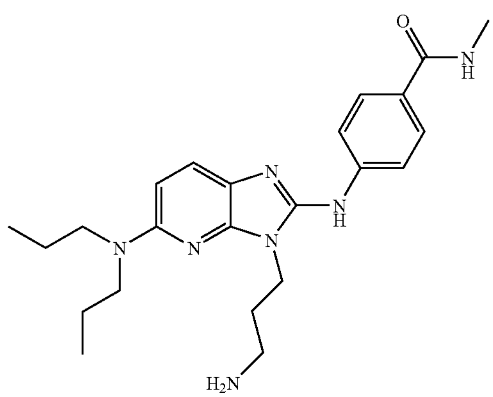 | 424.3 | 7.6 |
| 128 | 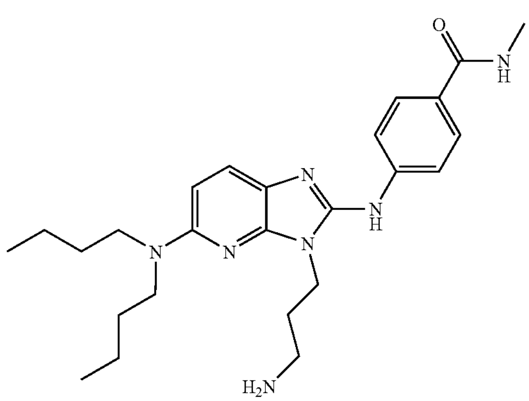 | 452.3 | 7.9 |

-continued

| Examples | Molecular structures | [M + H]+ | rt (min) |
|---|---|---|---|
| 129 | 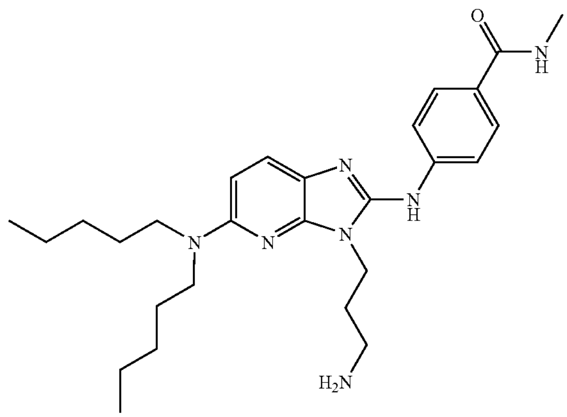 | 480.4 | 8.3 |
| 130 | 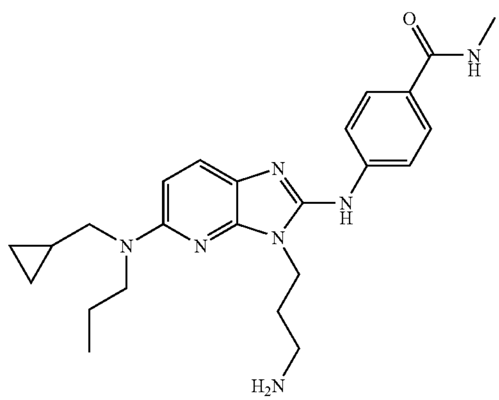 | 436.3 | 7.6 |
| 131 | 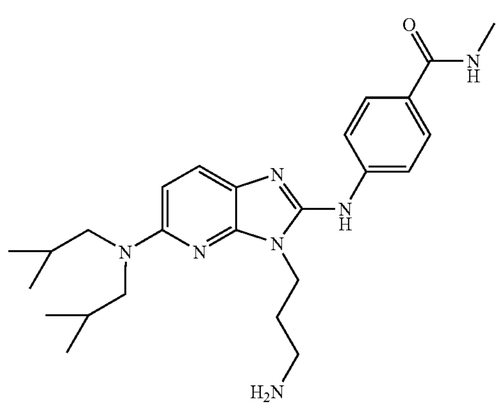 | 452.3 | 7.9 |

-continued

| Examples | Molecular structures | [M + H]+ | rt (min) |
|---|---|---|---|
| 132 | 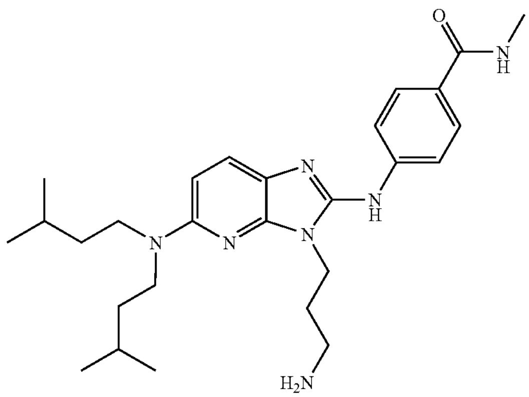 | 480.4 | 8.2 |
| 133 | 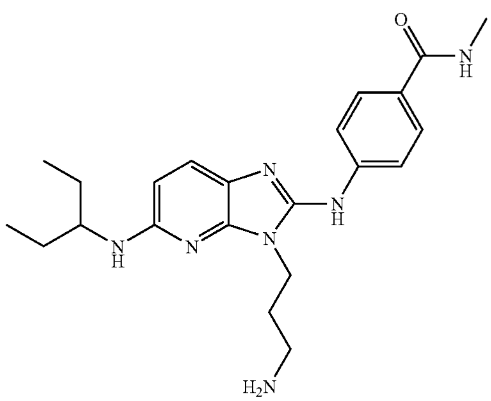 | 410.3 | 7.4 |
| 134 | 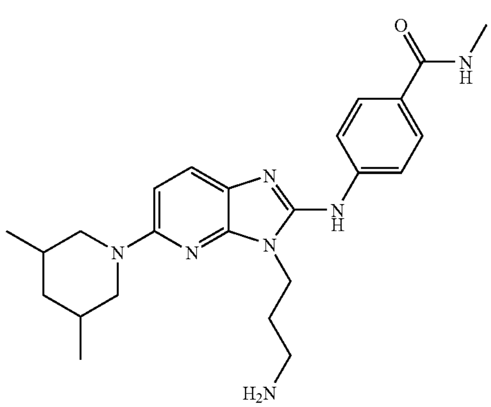 | 436.3 | 7.6 |

-continued
| Examples | Molecular structures | [M + H]+ | rt (min) |
|---|---|---|---|
| 135 | 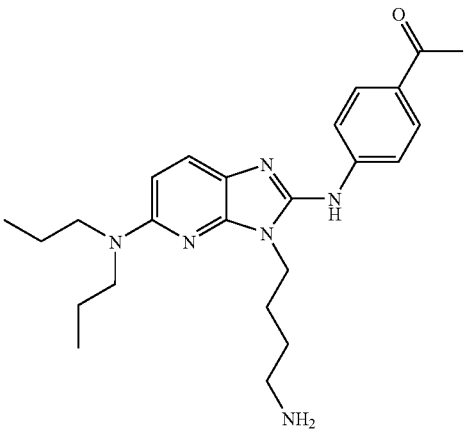 | 423.1 | 7.8 |
| 136 | 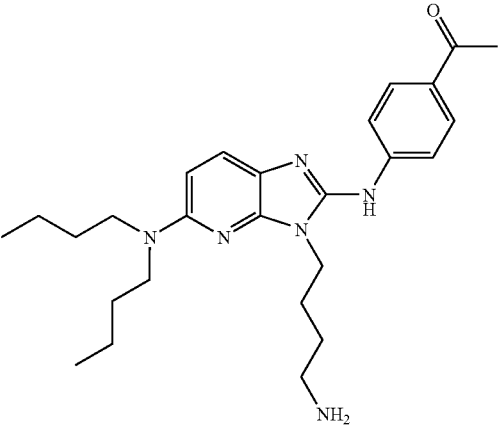 | 451.1 | 8.2 |
| 137 | 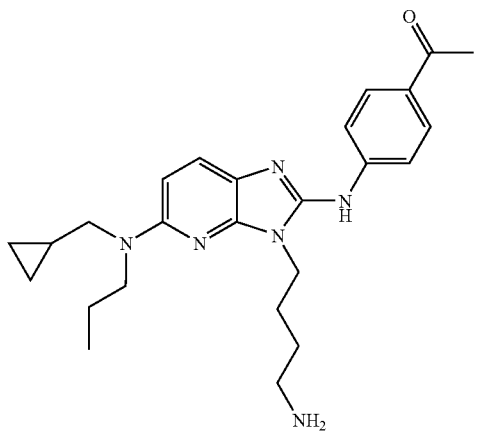 | 435.1 | 7.8 |

-continued

| Examples | Molecular structures | [M + H]+ | rt (min) |
|---|---|---|---|
| 138 | 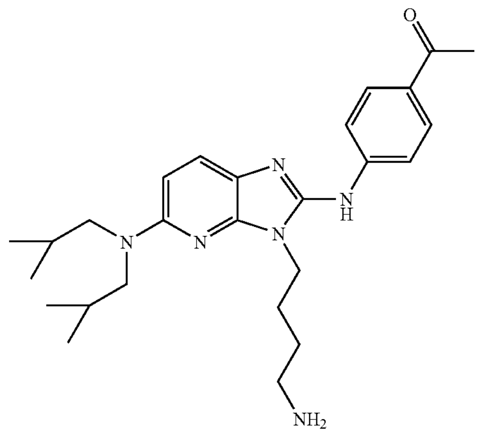 | 451.2 | 8.1 |
| 139 | 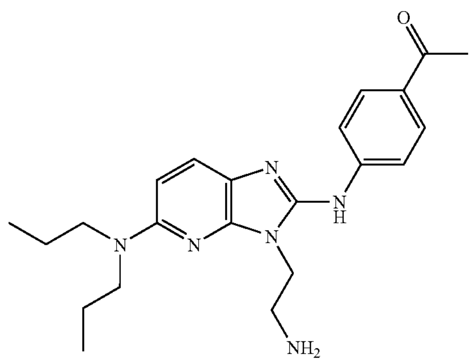 | 395.0 | 7.9 |
| 140 | 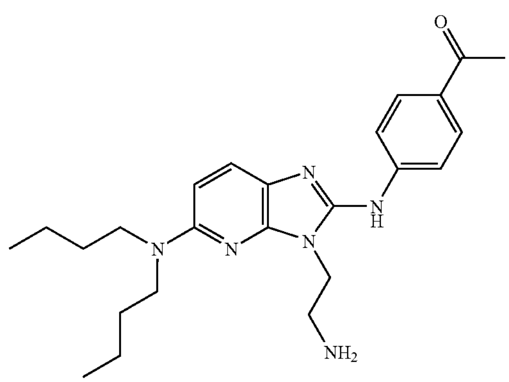 | 423.0 | 8.3 |
| 141 | 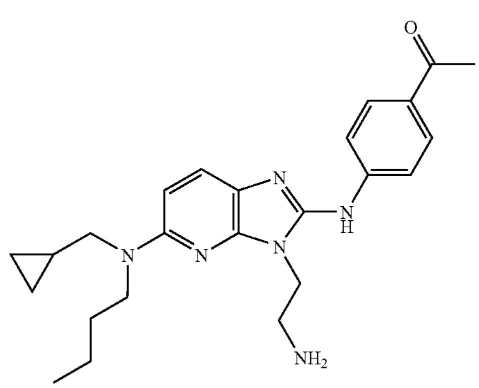 | 407.0 | 7.9 |

-continued

| Examples | Molecular structures | [M + H]+ | rt (min) |
|---|---|---|---|
| 142 | 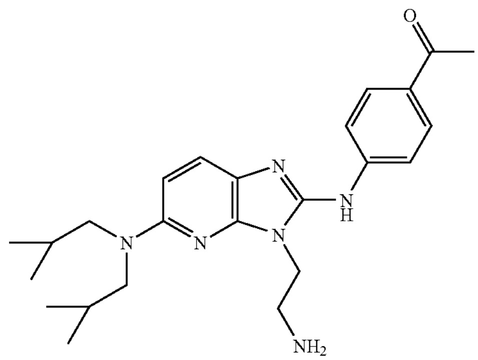 | 423.0 | 8.3 |
| 143 | 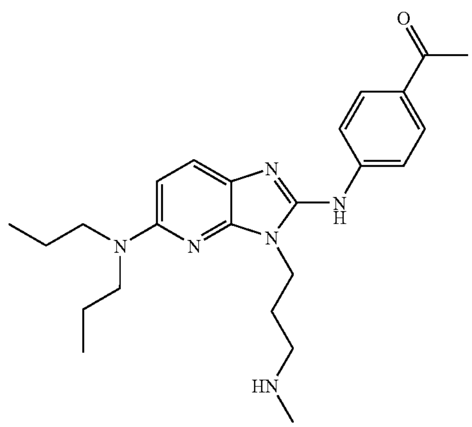 | 423.2 | 7.9 |
| 144 | 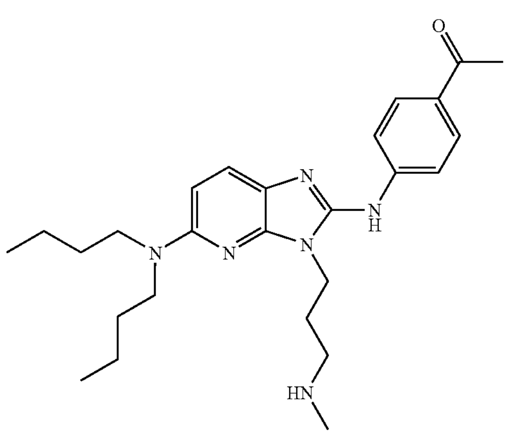 | 451.2 | 8.3 |

-continued
| Examples | Molecular structures | [M + H]+ | rt (min) |
|---|---|---|---|
| 145 | 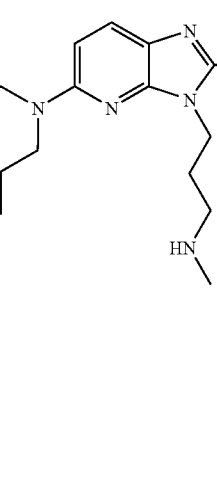 | 435.2 | 7.9 |
| 146 | 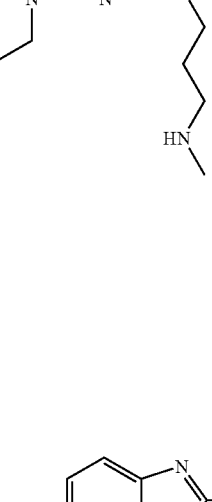 | 451.3 | 8.2 |
| 147 | 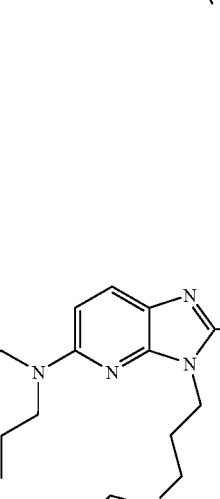 | 479.2 | 8.0 |

-continued

| Examples | Molecular structures | [M + H]+ | rt (min) |
|---|---|---|---|
| 148 | 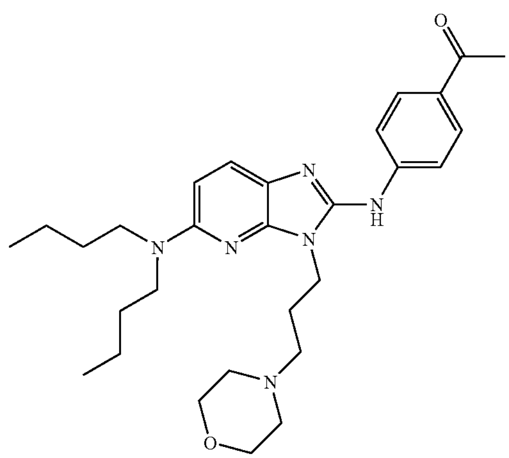 | 507.3 | 8.4 |
| 149 | 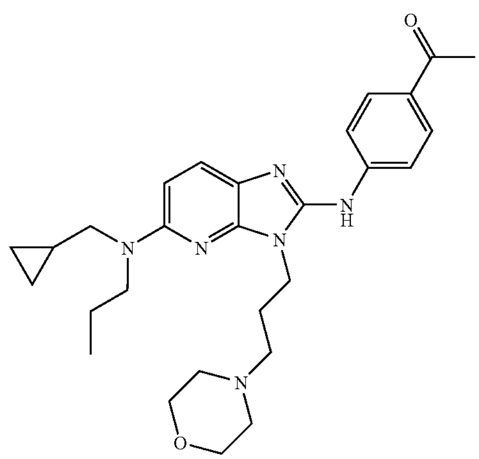 | 491.3 | 8.0 |
| 150 | 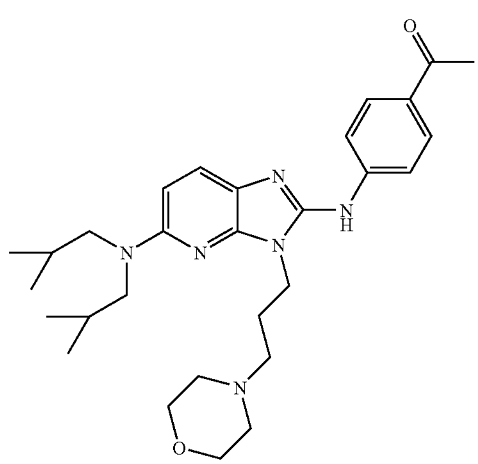 | 507.3 | 8.4 |

-continued

| Examples | Molecular structures | [M + H]+ | rt (min) |
|---|---|---|---|
| 151 | 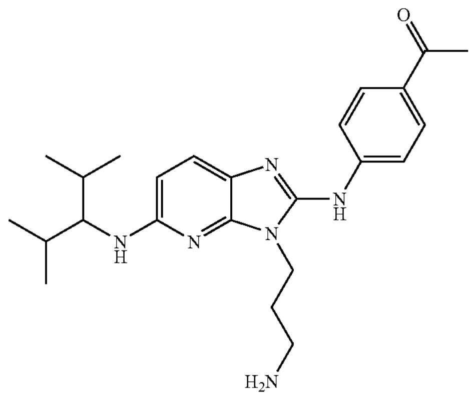 | 423.3 | 7.3 |
| 152 | 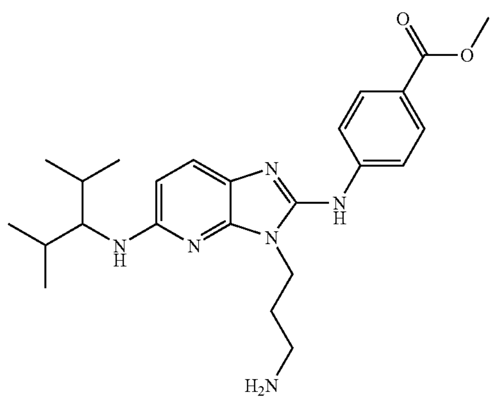 | 439.3 | 7.2 |
| 153 | 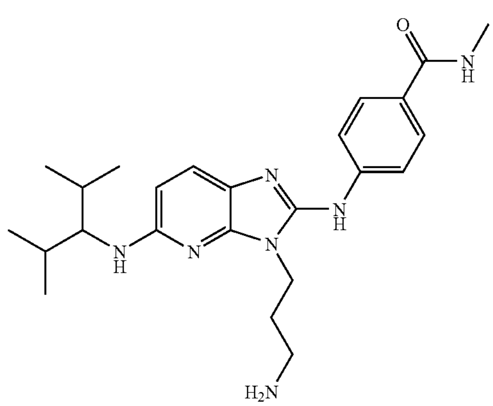 | 438.3 | 7.2 |

-continued

| Examples | Molecular structures | [M + H]+ | rt (min) |
|---|---|---|---|
| 154 | 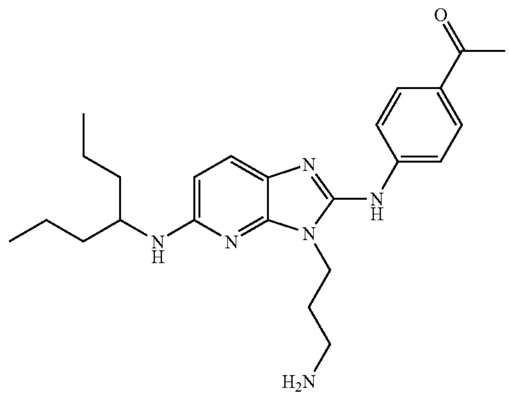 | 423.2 | 7.4 |
| 155 | 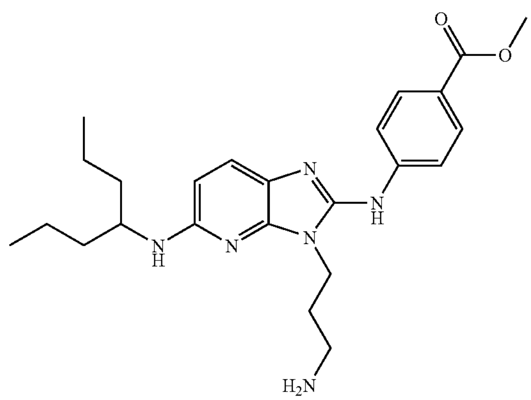 | 439.3 | 7.5 |
| 156 | 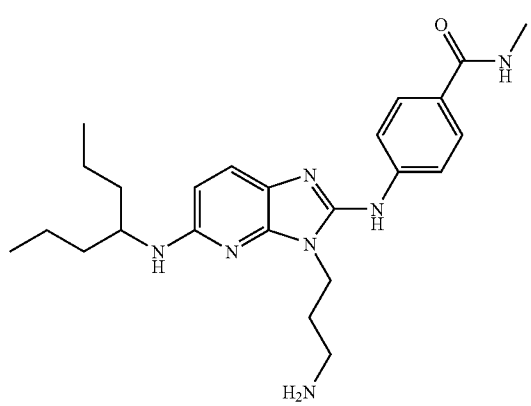 | 438.3 | 7.2 |

| Examples | Molecular structures | [M + H]+ | rt (min) |
|---|---|---|---|
| 157 | 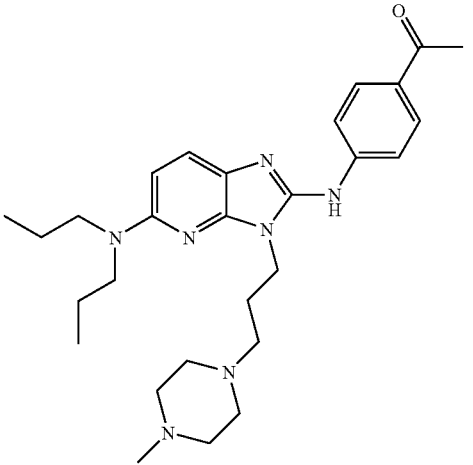 | 492.4 | 7.3 |
| 158 | 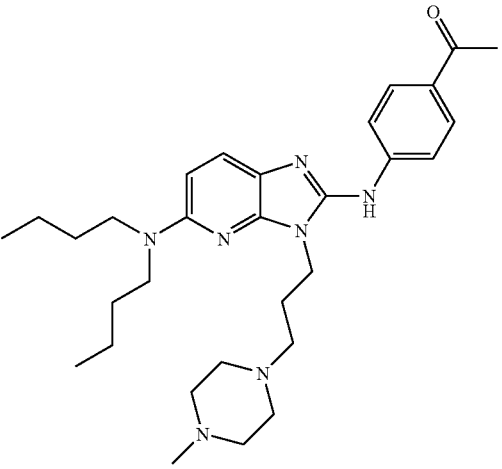 | 520.4 | 7.6 |
| 159 | 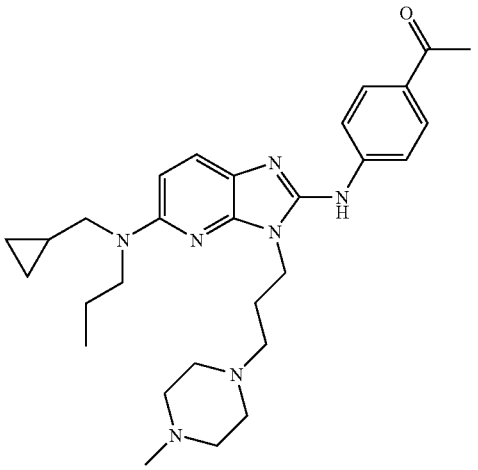 | 504.4 | 7.3 |

-continued
| Examples | Molecular structures | [M + H]+ | rt (min) |
|---|---|---|---|
| 160 | 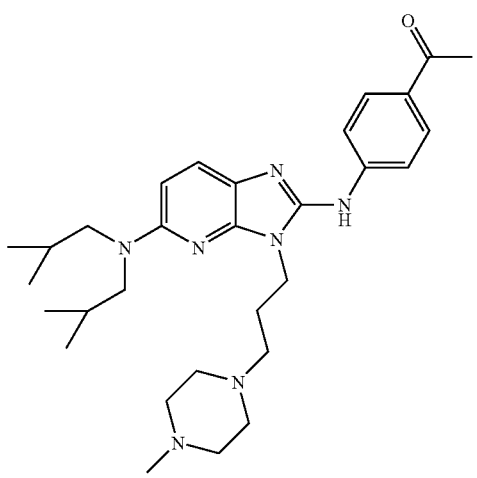 | 520.4 | 7.6 |
| 161 | 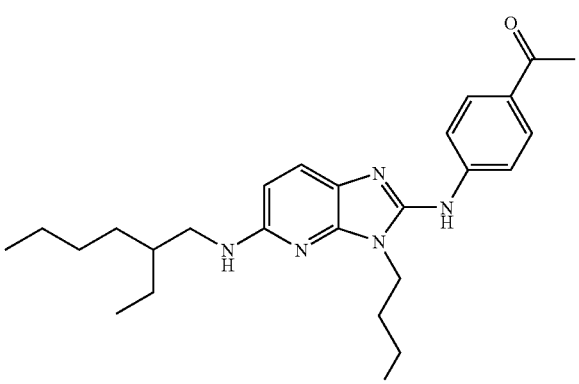 | 437.3 | 8.3 |
| 162 | 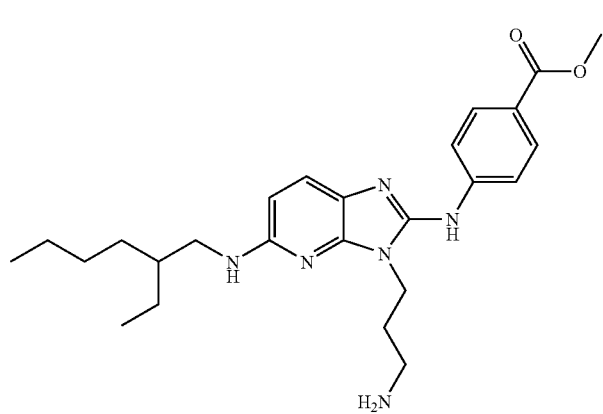 | 453.3 | 8.4 |

-continued

| Examples | Molecular structures | [M + H]+ | rt (min) |
|----------|---------------------|----------|----------|
| 163 | 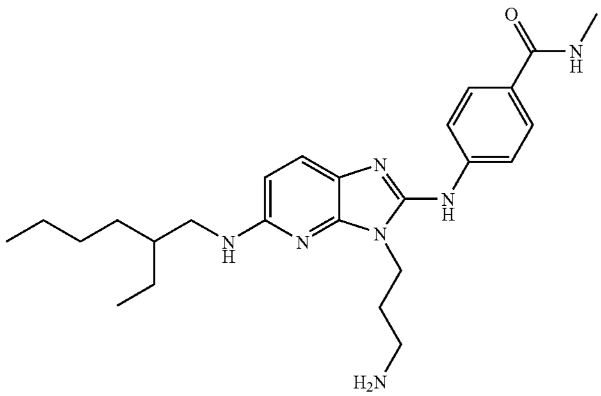 | 452.3 | 8.0 |
| 164 | 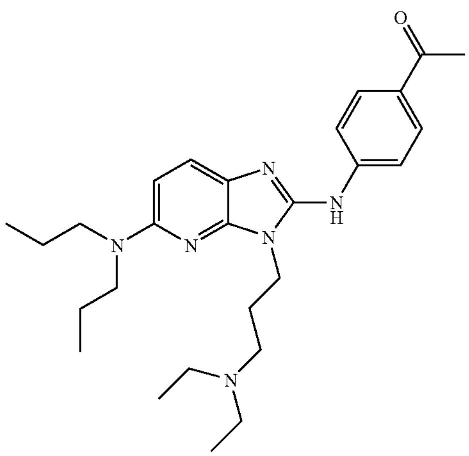 | 465.3 | 8.0 |
| 165 | 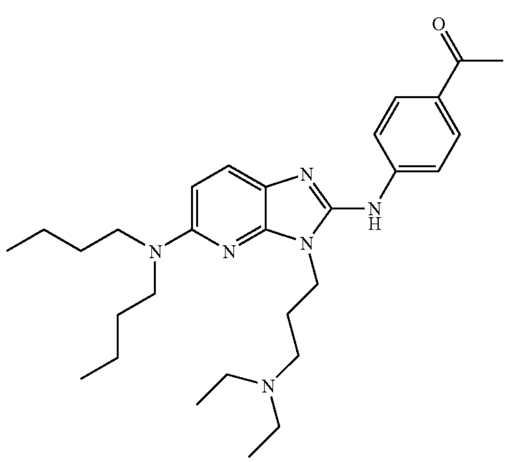 | 493.4 | 8.5 |

-continued

| Examples | Molecular structures | [M + H]+ | rt (min) |
|---|---|---|---|
| 166 | 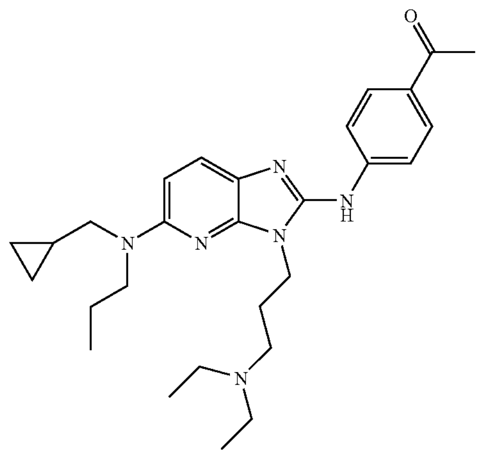 | 477.3 | 8.1 |
| 167 | 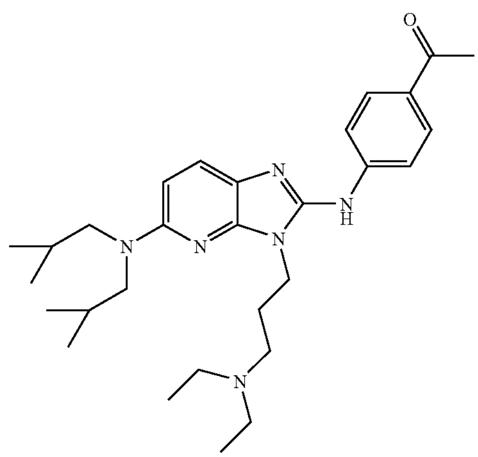 | 493.4 | 8.4 |
| 168 | 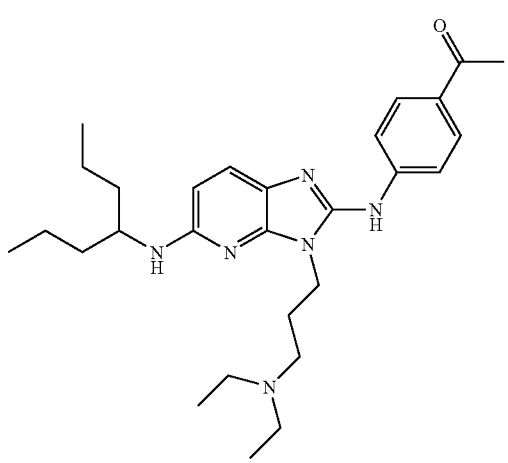 | 479.4 | 8.2 |

-continued
| Examples | Molecular structures | [M + H]+ | rt (min) |
|---|---|---|---|
| 169 | 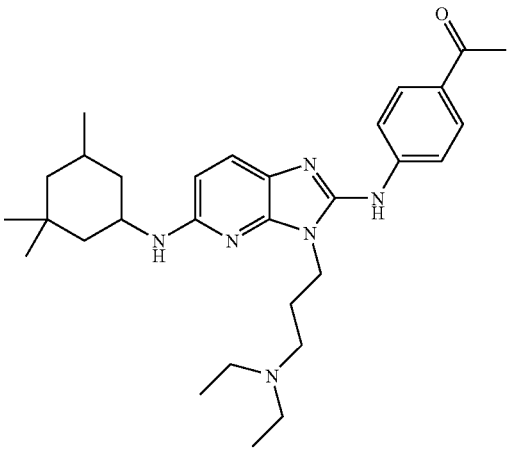 | 505.4 | 8.4 |
| 170 | 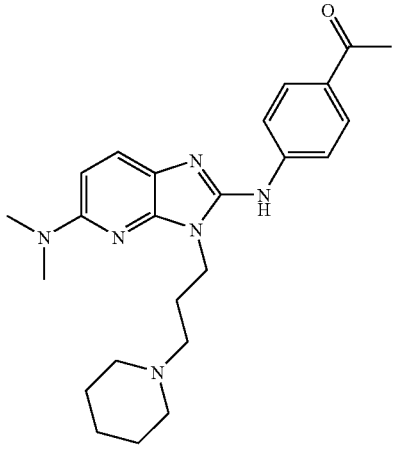 | 421.3 | 7.4 |
| 171 | 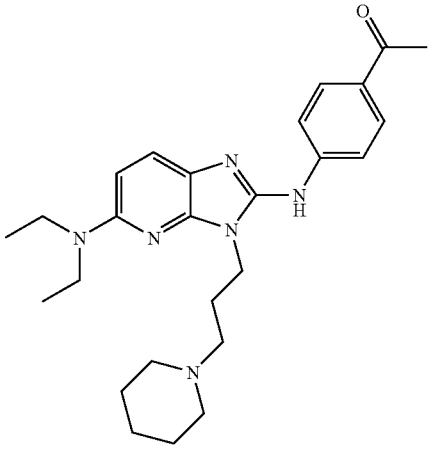 | 449.4 | 7.6 |

-continued

| Examples | Molecular structures | [M + H]+ | rt (min) |
|---|---|---|---|
| 172 | 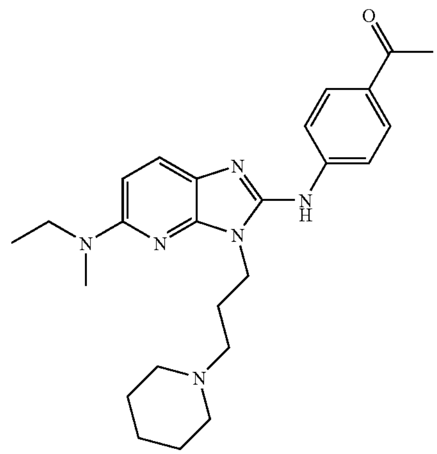 | 435.3 | 7.5 |
| 173 | 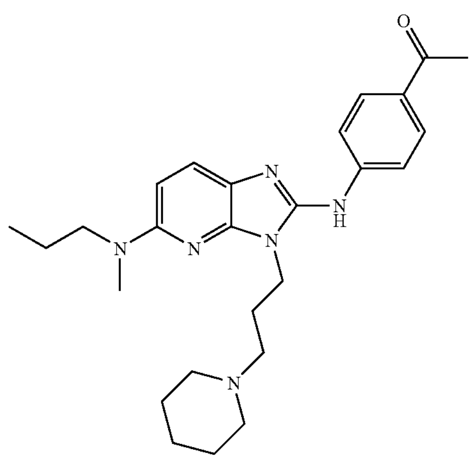 | 449.4 | 7.7 |
| 174 | 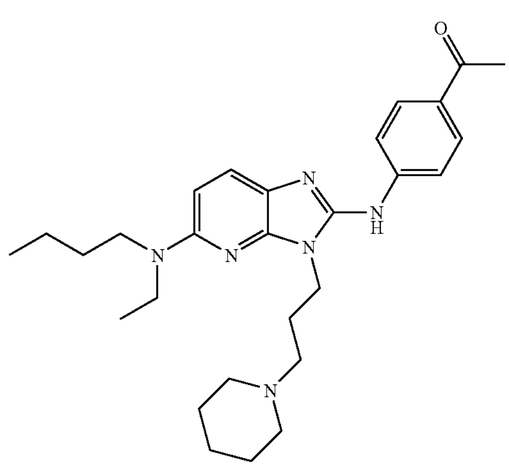 | 477.4 | 8.0 |

-continued

| Examples | Molecular structures | [M + H]+ | rt (min) |
|---|---|---|---|
| 175 | 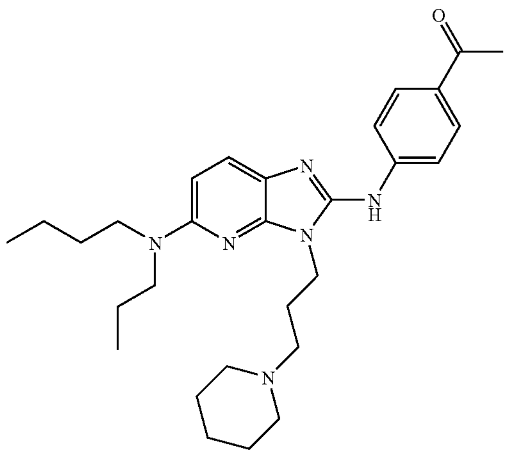 | 491.4 | 8.3 |
| 176 | 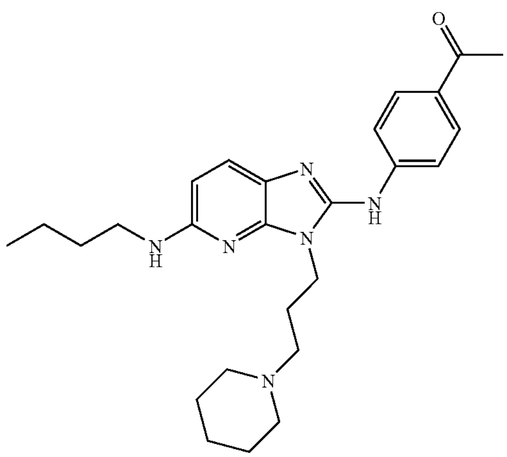 | 449.4 | 7.6 |
| 177 | 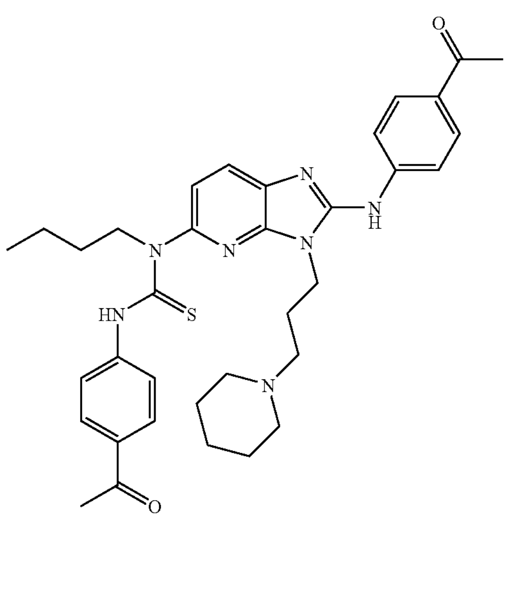 | 626.4 | 8.8 |

-continued

| Examples | Molecular structures | [M + H]+ | rt (min) |
|---|---|---|---|
| 178 | 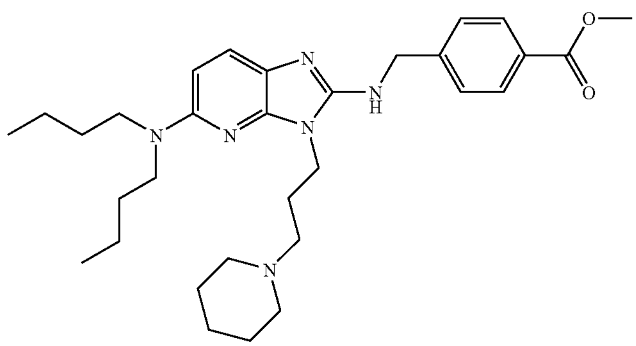 | 535.4 | 8.4 |
| 179 | 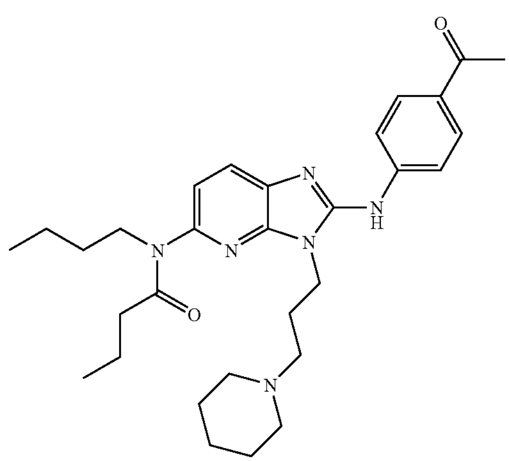 | 519.4 | 8.8 |
| 180 | 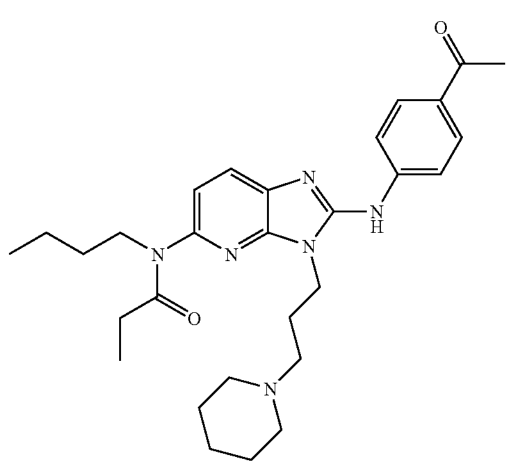 | 505.3 | 8.6 |

| Examples | Molecular structures | [M + H]+ | rt (min) |
|---|---|---|---|
| 181 | 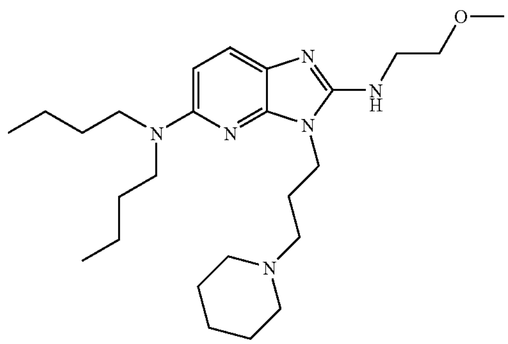 | 445.4 | 8.4 |
| 182 | 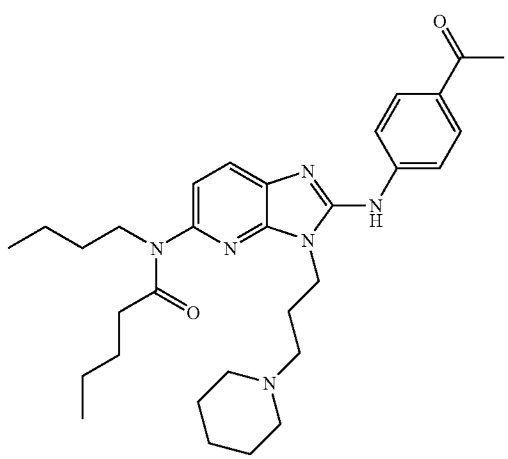 | 533.3 | 8.9 |
| 183 | 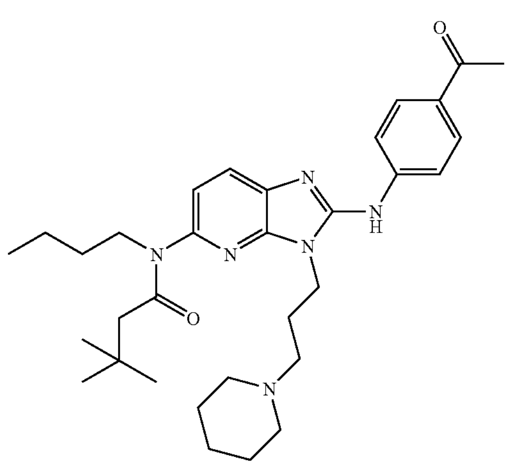 | 547.4 | 9.1 |

-continued
| Examples | Molecular structures | [M + H]+ | rt (min) |
|---|---|---|---|
| 184 | 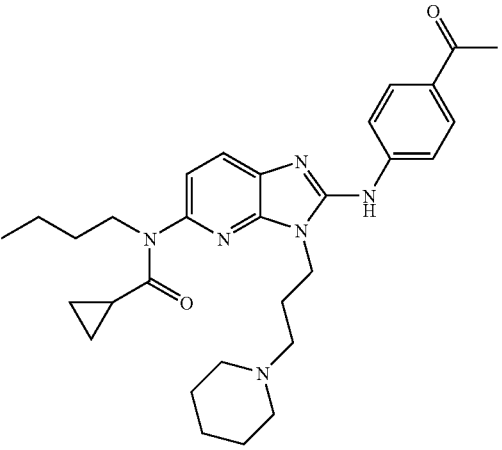 | 517.3 | 8.5 |
| 185 | 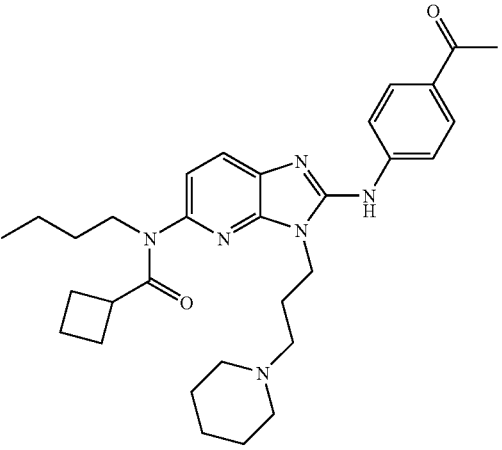 | 531.3 | 8.7 |
| 186 | 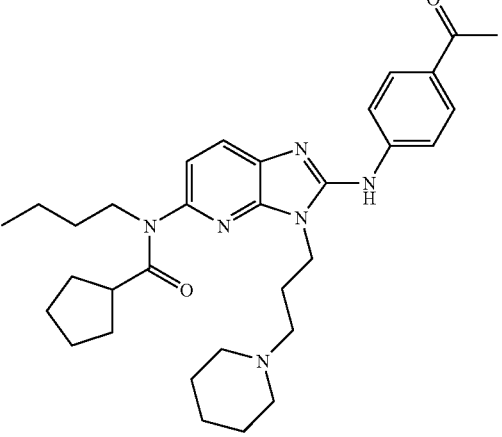 | 545.3 | 8.9 |

-continued

| Examples | Molecular structures | [M + H]+ | rt (min) |
|---|---|---|---|
| 187 | 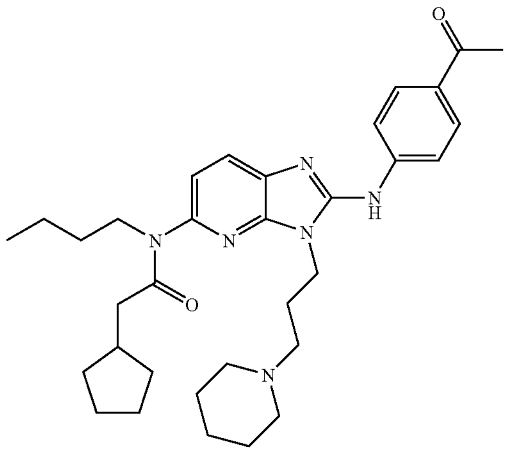 | 559.4 | 9.1 |
| 188 | 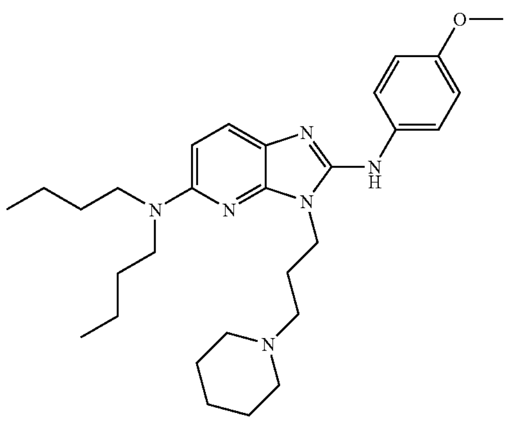 | 493.4 | 8.7 |
| 189 | 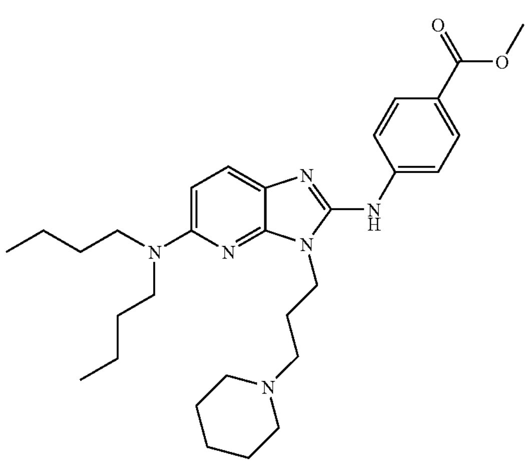 | 521.4 | 8.8 |

-continued

| Examples | Molecular structures | [M + H]+ | rt (min) |
| --- | --- | --- | --- |
| 190 | 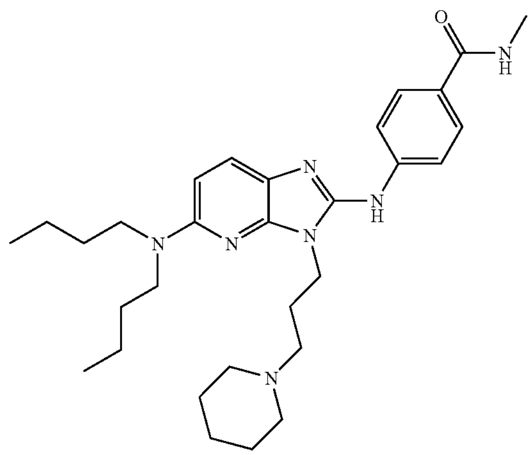 | 520.4 | 8.4 |
| 191 | 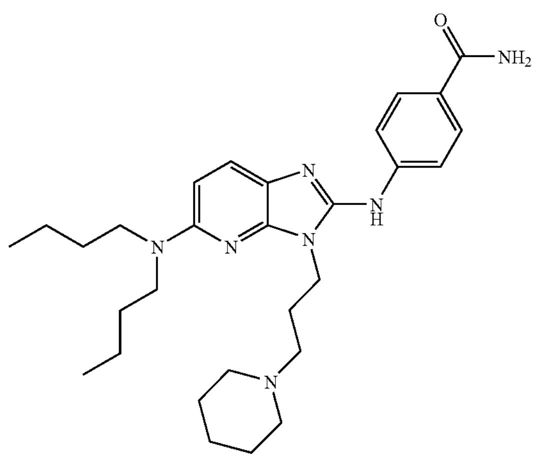 | 506.4 | 8.4 |
| 192 | 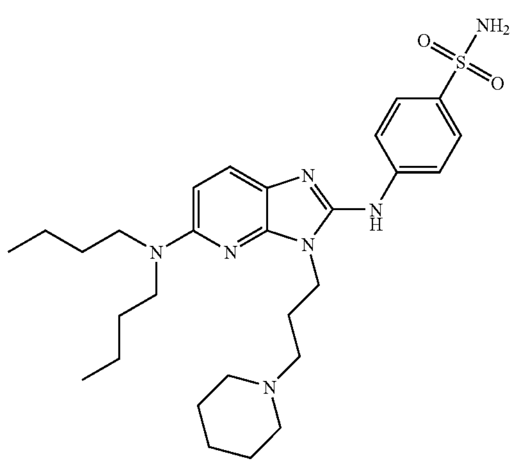 | 542.3 | 8.6 |

-continued

| Examples | Molecular structures | [M + H]+ | rt (min) |
|---|---|---|---|
| 193 | 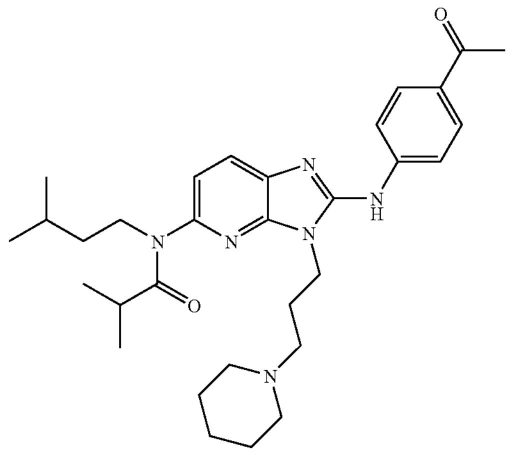 | 533.3 | 8.9 |
| 194 | 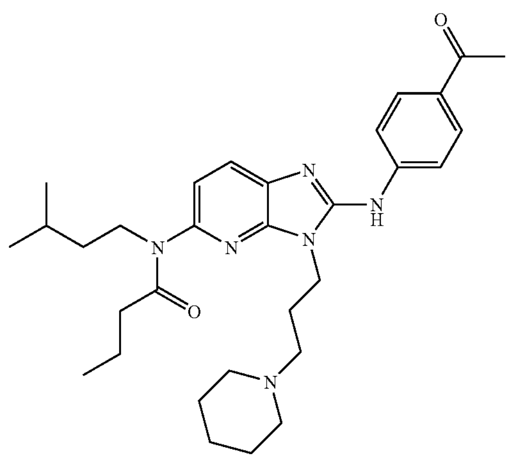 | 533.3 | 8.9 |
| 195 | 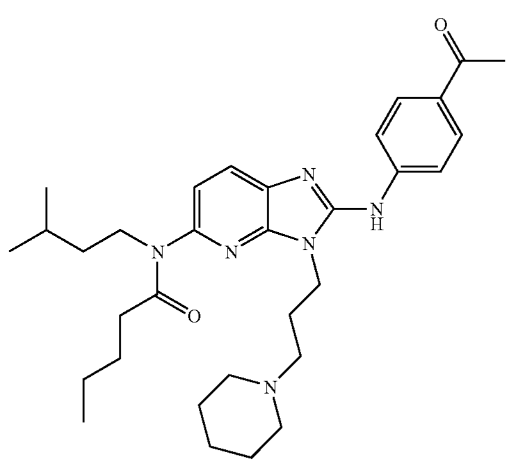 | 547.3 | 9.1 |

-continued

| Examples | Molecular structures | [M + H]+ | rt (min) |
|---|---|---|---|
| 196 | 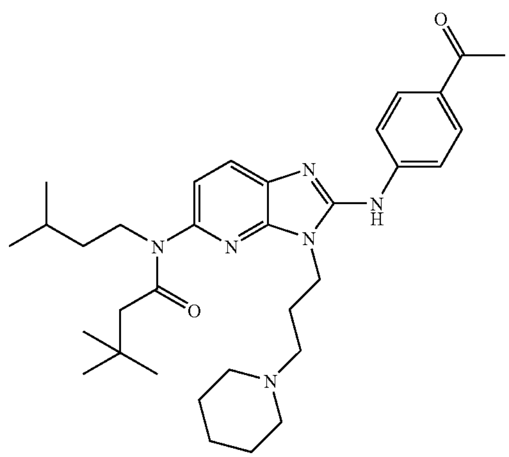 | 561.4 | 9.4 |
| 197 | 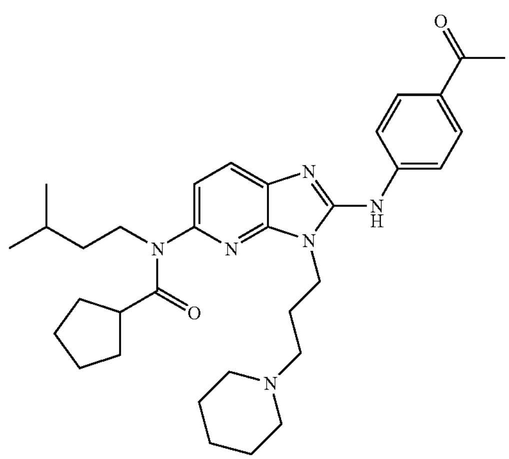 | 559.4 | 9.2 |
| 198 | 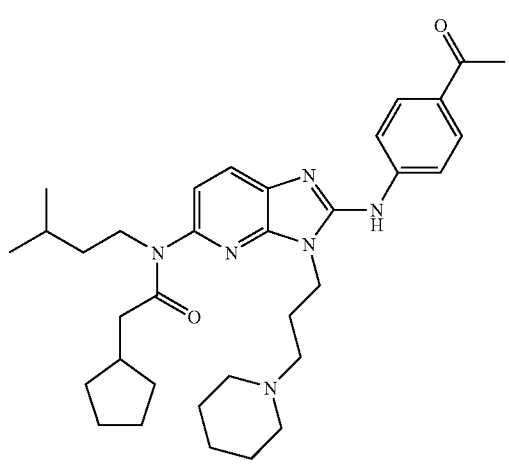 | 573.4 | 9.4 |

-continued

| Examples | Molecular structures | [M + H]+ | rt (min) |
|---|---|---|---|
| 199 | 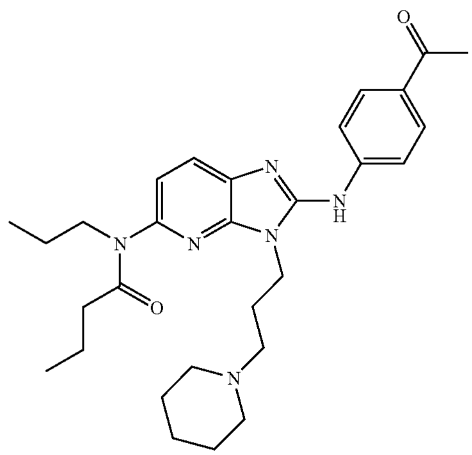 | 505.3 | 8.4 |
| 200 | 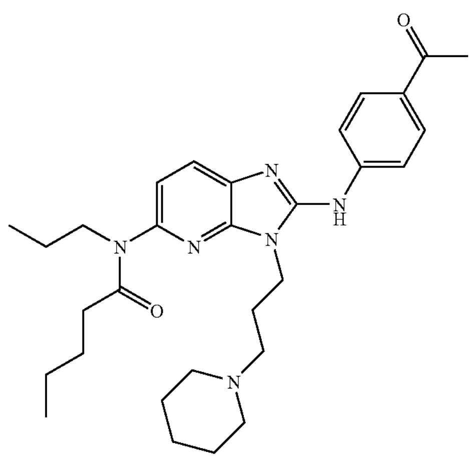 | 519.3 | 8.7 |
| 201 | 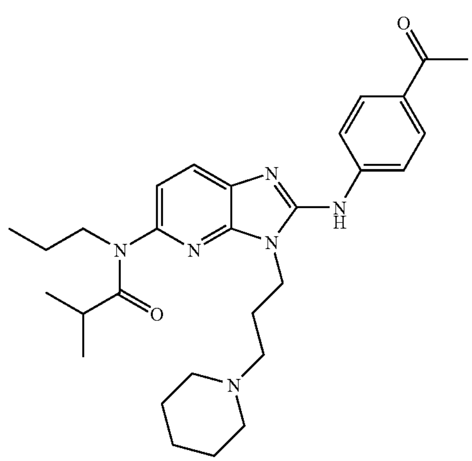 | 505.3 | 8.4 |

| Examples | Molecular structures | [M + H]+ | rt (min) |
|---|---|---|---|
| 202 | 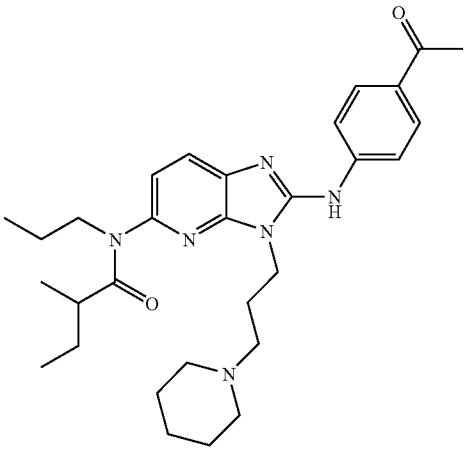 | 519.3 | 8.6 |
| 203 | 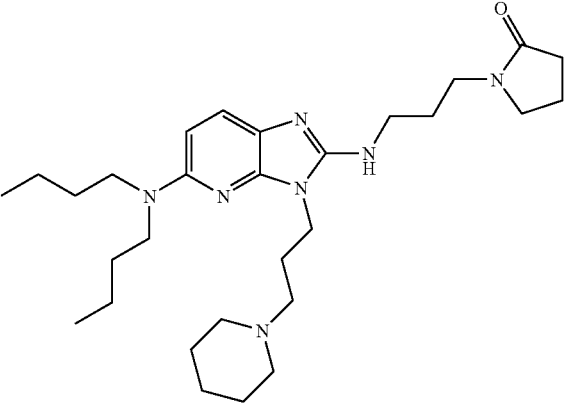 | 512.4 | 8.6 |
| 204 | 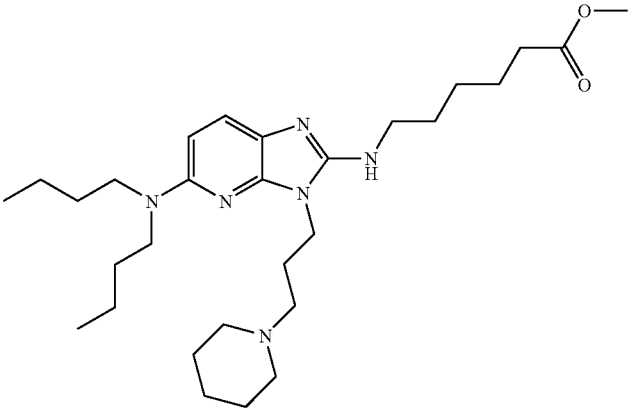 | 515.4 | 8.8 |

-continued

| Examples | Molecular structures | [M + H]+ | rt (min) |
|---|---|---|---|
| 205 | 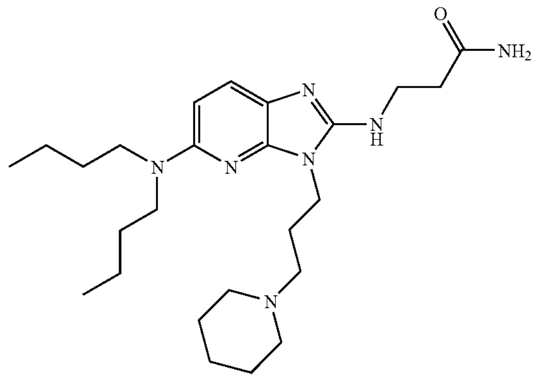 | 458.3 | 8.4 |
| 206 | 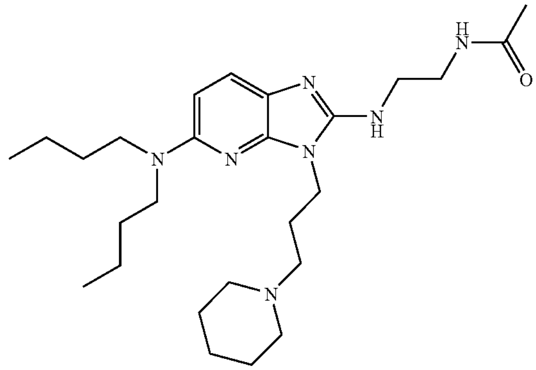 | 472.4 | 8.5 |
| 207 | 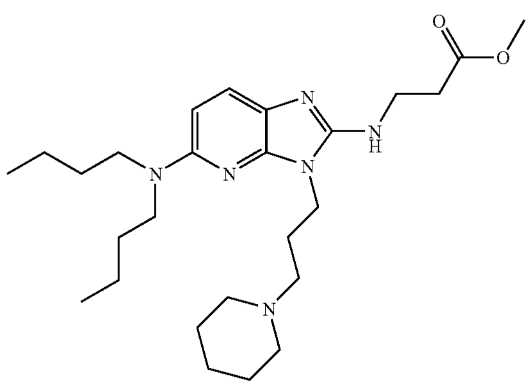 | 473.4 | 8.2 |
| 208 | 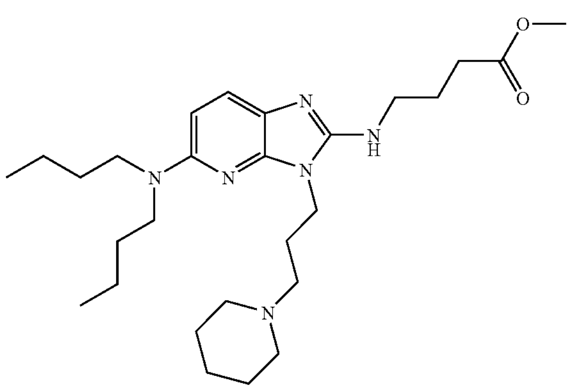 | 487.4 | 8.3 |

-continued

| Examples | Molecular structures | [M + H]+ | rt (min) |
|---|---|---|---|
| 209 | 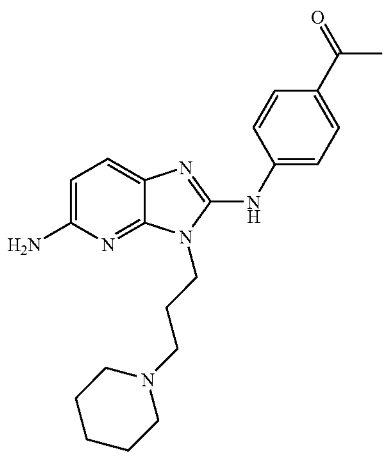 | 393.2 | 7.2 |
| 210 | 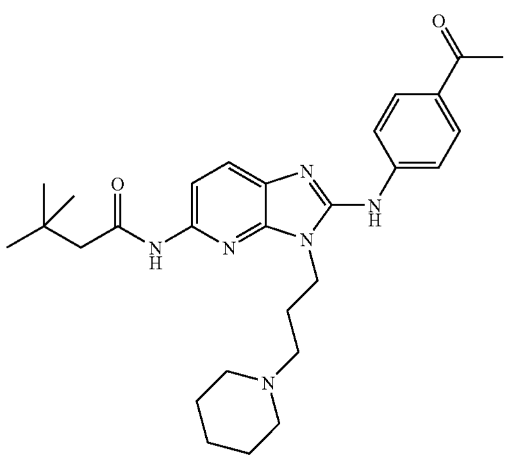 | 491.6 | 8.1 |
| 211 | 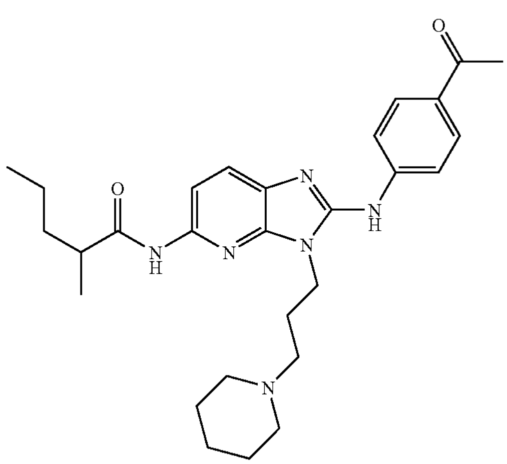 | 491.6 | 8.1 |

Pharmacological Study

The affinity of the compounds of the present invention for the different sub-types of melanocortin receptors was measured according to procedures analogous to those described hereafter for the MC4 receptors.

Studies of the Affinity of the Compounds for the MC4 Receptors of Melanocortins:

The affinity of the compounds of the invention for the MC4 receptors is determined by measuring the inhibition of the binding of [$^{125}$I]-[Nle$^4$, D-Phe$^7$]-α-MSH to membrane preparations of transfected CHO-K1 cells.

CHO-K1 cells expressing human MC4 receptors in a stable fashion are cultured in an RPMI 1640 medium containing 10% of fetal calf serum, 2 mM of glutamine, 100 U/ml of penicillin, 0.1 mg/ml of streptomycin and 0.5 mg/ml of G418. The cells are collected with 0.5 mM of EDTA and centrifuged at 500 g for 5 minutes at 4° C. The pellet is re-suspended in a phosphate buffered saline (PBS) medium and centrifuged at 500 g for 5 min at 4° C. The pellet is re-suspended in a Tris 50 mM buffer medium at pH 7.4 and centrifuged at 500 g for 5 minutes at 4° C. The cells are lysed by sonication and centrifuged at 39,000 g for 10 minutes at 4° C. The pellet is re-suspended in Tris 50 mM buffer medium at pH 7.4 and centrifuged at 50,000 g for 10 minutes at 4° C. The membranes obtained in this last pellet are stored at −80° C.

Measurement of the competitive inhibition of the binding of [$^{125}$I]-[Nle$^4$, D-Phe$^7$]-α-MSH to the MC4 receptors is carried out in duplicate using polypropylene 96-well plates. The cell membranes (50 μg of proteins/well) are incubated with [$^{125}$I]-[Nle$^4$, D-Phe$^7$]-α-MSH (0.5 nM) for 90 minutes at 37° C. in a 50 mM Tris-HCl buffer medium, pH 7.4, comprising 0.2% of bovine serum albumin (BSA), 5 mM of MgCl$_2$, and 0.1 mg/ml of bacitracin.

The bonded [$^{125}$I]-[Nle$^4$, D-Phe$^7$]-α-MSH is separated from the free [$^{125}$I]-[Nle$^4$, D-Phe$^7$]-α-MSH by filtration through GF/C glass fibre filter plates (Unifilter, Packard) pre-impregnated with 0.1% of polyethylenimine (P.E.I.), using a Filtermate 196 (Packard). The filters are washed with 50 mM Tris-HCl buffer, pH 7.4 at 04° C. and the radioactivity present is determined using a counter (Packard Top Count).

The specific binding is obtained by subtracting the non-specific binding (determined in the presence of 0.1 μM of Nle$^4$, D-Phe$^7$-α-MSH) of the total binding. The data are analyzed by computer-assisted non-linear regression (MDL) and the values of the inhibition constants (Ki) are determined.

The agonist or antagonist activity of the MC4 receptors of the compounds of the present invention were determined by measuring the production of cyclic AMP by the CHO-K1 cells transfected by the MC4 receptor.

Measurement of the Production of Intracellular Cyclic AMP via the MC4 Receptors:

CHO-K1 cells expressing the MC4 receptors of the melanocortins are cultured in 384-well plates in an RPMI 1640 medium with 10% of foetal calf serum and 0.5 mg/ml of G418. The cells are washed twice with 50 μl of RPMI medium comprising 0.2% BSA and 0.5 mM of 3-isobutyl-1-methylxanthine (IBMX).

In order to measure the agonist effect of a compound, the cells are incubated for 5 minutes at 37° C. in the presence of 0.5 mM of IBMX, then stimulation of the production of cyclic AMP is obtained by adding the compound at concentrations comprised between 1 pM and 10 μM in duplicate for 20 minutes at 37° C. The antagonist effect of a compound is measured by the simultaneous addition of Nle$^4$, D-Phe$^7$-α-MSH at concentrations comprised between 1 pM and 10 μM, in the presence of the compound to be tested, at concentrations comprised between 0.1 nM and 10 μM in duplicate for 20 minutes at 37° C.

The reaction medium is eliminated and 80 μl of lysis buffer is added. The intracellular cyclic AMP level is measured by a competition test with fluorescent cyclic AMP (CatchPoint, Molecular Devices).

The invention claimed is:

1. A compound of the formula

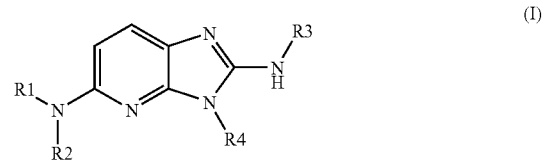

(I)

in racemic, or enantiomeric form or any combinations of these forms and wherein:

R$_1$ and R$_2$ are, independently, selected from the group consisting of hydrogen, (C$_1$-C$_8$)alkyl optionally substituted by hydroxy, (C$_2$-C$_6$)alkenyl; bicycloalkyl, —(CH$_2$)$_n$—X$_1$ and —X—(CH$_2$)$_{n'}$—X'$_1$;

X is selected from the group consisting of —C(O)— or —C(S)—NH—;

X$_1$ is selected from the group consisting of (C$_1$-C$_6$)alkoxy, (C$_3$-C$_7$)cycloalkyl, adamantyl, heterocycloalkyl, aryl and heteroaryl, The (C$_3$-C$_7$)cycloalkyl, heterocycloalkyl, aryl and heteroaryl being optionally substituted by at least one member selected from the group consisting of:

—(CH$_2$)$_{n1}$—V$_1$—Y$_1$, halo, nitro and cyano;

V$_1$ is selected from the group consisting of —O—, —S— or covalent bond;

Y$_1$ is (C$_1$-C$_6$)alkyl optionally substituted by at least one halo, or aryl;

n and n' are integers from 0 to 6 and n$_1$ an integer from 0 to 2 (it being understood that when n is equal to 0, then X$_1$ is not alkoxy);

X'$_1$ is selected from the group consisting of hydrogen, (C$_1$-C$_6$)alkyl optionally substituted by at least one halo, (C$_3$-C$_7$)cycloalkyl; and aryl optionally substituted by at least one member: halo, nitro, cyano, (C$_1$-C$_6$)alkyl-carbonyl, (C$_1$-C$_6$)alkyl optionally substituted by at least one halo, and (C$_1$-C$_6$)alkoxy optionally substituted by at least one halo;

or R$_1$ and R$_2$ form together, with the nitrogen atom to which they are attached, a heterobicycloalkyl or a heterocycloalkyl optionally substituted by at least one member selected from the group consisting of: hydroxy, (C$_1$-C$_6$) alkyl optionally substituted by hydroxy, (C$_1$-C$_6$)alkyl-carbonyl, —(CH$_2$)$_{n'}$-A, —C(O)—NV$_1$'—Y$_1$', and heterocycloalkyl; or R$_1$ and R$_2$ form together a member selected from the group consisting of:

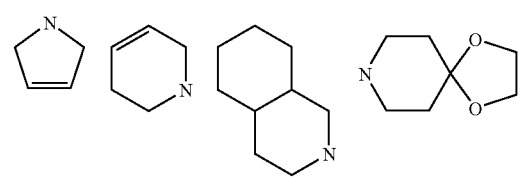

$V_1'$ and $Y_1'$ are, independently, hydrogen or $(C_1-C_6)$alkyl;

A is aryl optionally substituted by at least one member selected from the group consisting of: halo, nitro, cyano, $(C_1-C_6)$alkyl optionally substituted by at least one member selected from the group halo, and $(C_1-C_6)$alkoxy optionally substituted by at least one halo;

n" is an integer from 0 to 2;

$R_3$ is selected from the group consisting of -$Z_3$, —$C(R_{z3})(R'_{z3})$-$Z_3$—$C(R_{z3})(R'_{z3})$—$(CH_2)_p$-$Z_3$ and —$C(O)$-$Z'_3$;

$R_{z3}$ and $R'_{z3}$ are, independently, hydrogen or $(C_1-C_6)$alkyl;

$Z_3$ is selected from the group consisting of $Z_{3a}$, $Z_{3b}$, $Z_{3c}$, $Z_{3d}$, and $Z_{3e}$;

$Z_{3a}$ is $(C_1-C_6)$alkyl or $(C_2-C_6)$alkenyl;

$Z_{3b}$ is selected from the group consisting of $(C_1-C_6)$alkoxy, $C_1-C_6$)alkylthio, $C_1-C_6$)alkylamino and di($(C_1-C_6)$alkyl)amino;

$Z_{3c}$ is aryl or heteroaryl; the aryl and heteroaryl being optionally substituted by at least one member selected from the group consisting of: halo, cyano, nitro, azido, oxy and —$(CH_2)_{p'}$—$V_3$—$Y_3$;

$V_3$ is selected from the group consisting of —O—, —S—, —C(O)—, —C(O)—O—, —O(CO)—, —$SO_2$—, —$SO_2$NH—, —$NR'_3$—$SO_2$—, —$NR'_3$—, —$NR'_3$—C(O)—, —C(O)—$NR'_3$—NH—C(O)—$NR'_3$— and covalent bond;

$Y_3$ is selected from the group consisting of hydrogen, $(C_1-C_6)$alkyl optionally substituted by at least one halo; aryl optionally substituted by at least one member selected from the group consisting of: halo, nitro, $(C_1-C_6)$alkyl and $(C_1-C_6)$alkoxy; and aryl-$(C_1-C_6)$alkyl optionally substituted by at least one member selected from the group consisting of: halo, nitro, $(C_1-C_6)$alkyl and $(C_1-C_6)$alkoxy;

$Z_{3d}$ is selected from the group consisting of $(C_1-C_6)$alkoxy-carbonyl, amino-carbonyl, $(C_1-C_6)$alkylamino-carbonyl and di($(C_1-C_6)$alkyl)amino-carbonyl;

$Z_{3e}$ is selected from the group consisting of $(C_1-C_6)$alkyl-C(O)—NH—, $(C_3-C_7)$cycloalkyl, heteroalkyl, heterocycloalkyl,

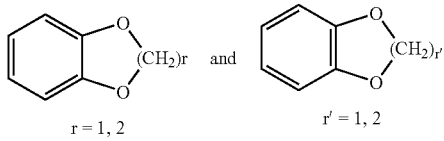

r = 1, 2    r' = 1, 2 the $(C_3-C_7)$cycloalkyl and heterocycloalkyl being optionally substituted by at least one oxy or $(C_1-C_6)$alkyl, $Z'_3$ is aryl optionally substituted by at least one member selected from the group consisting of: halo, nitro and —$(CH_2)_{p''}$—$V'_3$—$Y'_3$;

$V'_3$ is selected from the group consisting of —O—, —C(O)—, —C(O)—O—, —O(CO)—$NR'_3$—, —$NR'_3$—C(O)—, —NH—C(O)—$NR'_3$— and covalent bond;

$Y'_3$ is hydrogen or $(C_1-C_6)$alkyl optionally substituted by at least one halo;

$R'_3$ is selected from the group consisting of hydrogen, $(C_1-C_6)$alkyl and $(C_1-C_6)$alkoxy;

p, p' and p" are, independently, an integer from 0 to 6;

$R_4$ is —$(CH_2)_s$—$R'_4$ $R'_4$ is heterocycloalkyl containing at least one nitrogen atom and optionally substituted by $(C_1-C_6)$alkyl or arakyl; heteroaryl containing at least one nitrogen atom and optionally substituted by $(C_1-C_6)$alkyl; and —$NW_4W'_4$ $W_4$ is hydrogen or $(C_1-C_8)$alkyl;

$W'_4$ is —$(CH_2)_{s'}$-$Z_4$;

$Z_4$ is selected from the group consisting of hydrogen, $(C_1-C_8)$alkyl; $(C_2-C_6)$alkenyl; $(C_3-C_7)$cycloalkyl optionally substituted by at least one $(C_1-C_6)$alkyl; cyclohexene; heteroaryl and aryl optionally substituted by at least one member selected from the group consisting of:

—$(CH_2)_{s''}$—$V_4$—$Y_4$, halo and nitro;

$V_4$ is selected from the group consisting of —O—, —S—, —NH—C(O)—, —$NV_4'$— and covalent bond;

$Y_4$ is hydrogen or $(C_1-C_6)$alkyl optionally substituted by at least one halo;

$V_4'$ is hydrogen or $(C_1-C_6)$alkyl;

s" is an integer from 0 to 4;

or $Z_4$ is

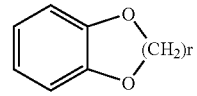

r = 1, 2 s and s' are, an integer from 0 to 6;

and a pharmaceutically acceptable salt thereof.

2. A compound of claim 1, wherein $R_1$ and $R_2$ are, independently, selected from the group consisting of hydrogen, $(C_1-C_8)$alkyl, bicycloalkyl, —$(CH_2)_n$—$X_1$ and —X—$(CH_2)_{n'}$—$X'_1$;

X is —C(O)— or —C(S)—NH—;

$X_1$ is selected from the group consisting of $(C_1-C_6)$alkoxy, $(C_3-C_7)$cycloalkyl optionally substituted by $(C_1-C_6)$alkyl, and heteroaryl;

$X'_1$ is selected from the group consisting of hydrogen, $(C_1-C_6)$alkyl optionally substituted by at least one halo, $(C_3-C_7)$cycloalkyl or aryl optionally substituted by $(C_1-C_6)$alkyl-carbonyl;

or $R_1$ and $R_2$ form together, with the nitrogen atom to which they are attached, are heterobicycloalkyl or a heterocycloalkyl optionally substituted by at least one member selected from the group consisting of: $(C_1-C_6)$alkyl, $(C_1-C_6)$alkyl-carbonyl and —$(CH_2)_{n''}$-A;

A is aryl optionally substituted by at least one: halo or $(C_1-C_6)$alkyl;

n" is an integer from 0 to 1;

$R_4$ is —$(CH_2)_s$—$R'_4$ $R'_4$ is heterocycloalkyl containing at least one nitrogen atom and optionally substituted by $(C_1-C_6)$alkyl; or —$NW_4W'_4$ $W_4$ is hydrogen, $(C_1-C_8)$alkyl;

$W'_4$ is —$(CH_2)_s$-$Z_4$;

$Z_4$ is selected from the group consisting of hydrogen, $(C_1-C_8)$alkyl and aryl optionally substituted by at least one: —$(CH_2)_{s''}$—$V_4$—$Y_4$;

$V_4$ is —O—;

$Y_4$ is $(C_1-C_6)$alkyl optionally substituted by at least one halo;

s" is an integer from 0 to 4;
s and s' are, independently, an integer from 1 to 4;
or a pharmaceutically acceptable salt thereof.

3. A compound of claim 2, wherein it comprises at least one of the following characteristics:
cycloalkyl chosen from cyclopropyl, cyclobutyl and cyclohexyl;
bicycloalkyl is bicyclo[2,2,1]heptane;
heterobicycloalkyl is 7-aza-biclyclo[2,2,1]heptane;
aryl is phenyl;
heteroaryl is furyl;
heterocycloalkyl is chosen from piperidine, morpholine and piperazine;
or a pharmaceutically acceptable salt thereof.

4. A compound of claim 1 wherein
$R_1$ and $R_2$ are, independently, hydrogen, $(C_1-C_6)$alkyl or —$(CH_2)_n$—$X_1$ or —X—$(CH_2)_{n'}$—$X'_1$;
X is —C(O)—;
$X_1$ is $(C_3-C_7)$cycloalkyl;
$X'_1$ is hydrogen or $(C_1-C_6)$cycloalkyl;
n is 0 or 1; n' is an integer from 0 to 5;
or $R_1$ and $R_2$ form together, with the nitrogen atom to which they are attached, are heterocycloalkyl optionally substituted by at least one $(C_1-C_6)$alkyl; or a pharmaceutically acceptable salt thereof.

5. A compound of claim 4, wherein the $(C_3-C_7)$cycloalkyl of $X_1$ and $X'_1$ is chosen from cyclopropyl, cyclobutyl and cyclohexyl; and heterocycloalkyl that together form $R_1$ and $R_2$, is piperidine; or a pharmaceutically acceptable salt thereof.

6. A compound of claim 1 wherein
$R_4$ is —$(CH_2)_s$—$R'_4$
$R'_4$ is heterocycloalkyl containing at least one nitrogen atom and optionally substituted by $(C_1-C_6)$alkyl; or —$NW_4W'_4$
$W_4$ is hydrogen or $(C_1-C_8)$alkyl;
$W'_4$ is —$(CH_2)_{s'}$-$Z_4$;
$Z_4$ is hydrogen or $(C_1-C_8)$alkyl;
s and s' are, independently, an integer from 2 to 4;
or a pharmaceutically acceptable salt thereof.

7. A compound of claim 6, wherein the heterocycloalkyl of $R'_4$ is: piperidine or morpholine; or a pharmaceutically acceptable salt thereof.

8. A compound of claim 1 wherein $R_3$ is —C(O)-$Z'_3$
$Z'_3$ is aryl optionally substituted by at least one member selected from the group consisting of halo and —$(CH_2)_{p''}$—$V'_3$—$Y'_3$;
$V'_3$ is —O— or covalent bond;
$Y'_3$ is hydrogen or $(C_1-C_6)$alkyl optionally substituted by at least one halo;
p" is an integer from 0 to 2;
or a pharmaceutically acceptable salt thereof.

9. A compound of claim 1 wherein $R_3$ is selected from the group consisting of $Z_3$, —C($R_{z3}$)($R'_{z3}$)-$Z_3$ and —C($R_{z3}$)($R'_{z3}$)—$(CH_2)_p$-$Z_3$; or a pharmaceutically acceptable salt thereof.

10. A compound of claim 9, wherein $R_3$ is -$Z_3$ and $Z_3$ is selected from the group consisting of $Z_{3b}$, $Z_{3c}$, $Z_{3e}$; or a pharmaceutically acceptable salt thereof.

11. A compound of claim 10, wherein $Z_3$ is $Z_{3c}$ and $Z_{3c}$ is aryl; or a pharmaceutically acceptable salt thereof.

12. A compound of claim 11, wherein $Z_{3c}$ is phenyl substituted by at least one member selected from the group consisting of: halo, nitro and —$(CH_2)_p$—$V_3$—$Y_3$;
$V_3$ is selected from the group consisting of —O—, —S—, —C(O)—, —C(O)—O—, —$SO_2NH$—, —$NR'_3$—C(O)—, —C(O)—$NR'_3$— and covalent bond;
$R'_3$ is hydrogen;
$Y_3$ is hydrogen or $(C_1-C_6)$alkyl optionally substituted by at least one halo; or a pharmaceutically acceptable salt thereof.

13. A compound of claim 11, wherein $Z_{3c}$ is phenyl substituted by at least one —$(CH_2)_p$—$V_3$—$Y_3$;
$V_3$ is selected from the group consisting of —C(O)—, —C(O)—O—, and —C(O)—$NR'_3$—;
$R'_3$ is hydrogen;
$Y_3$ is hydrogen or $(C_1-C_6)$alkyl; or a pharmaceutically acceptable salt thereof.

14. A compound of claim 9, wherein $R_3$ is —C($R_{z3}$)($R'_{z3}$)-$Z_3$ and $Z_3$ is $Z_{3d}$ or $Z_{3e}$; or a pharmaceutically acceptable salt thereof.

15. A compound of claim 9, wherein $R_3$ is —C($R_{z3}$)($R'_{z3}$)—$(CH_2)_p$-$Z_3$ and $Z_3$ is $Z_{3c}$, $Z_{3d}$ or $Z_{3e}$; or a pharmaceutically acceptable salt thereof.

16. A compound of claim 15, wherein $Z_3$ is $Z_{3d}$ or $Z_{3e}$;
$Z_{3d}$ is $(C_1-C_6)$alkoxy-carbonyl or amino-carbonyl;
$Z_{3e}$ is selected from the group consisting of $(C_1-C_6)$alkyl-C(O)—NH—, heterocycloalkyl optionally substituted by oxy, or r = 1, 2;

or pharmaceutically acceptable salt thereof.

17. A process for the preparation of a compound of claim 1 comprising reacting a compound of the formula:

wherein $R_1$, $R_2$, $R_4$ have the meaning of claim 1, with an isothiocyanate of the formula $R_3N=C=S$ in which $R_3$ has the meaning indicated in claim 1, in the presence of a coupling agent or of yellow mercury(II) oxide in the presence of sulfur, for a duration of 3 to 48 hours, in a protic or aprotic solvent, at a temperature of 50 to 80° C.

18. A pharmaceutical composition for treating weight disorders comprising an effective amount of a compound of claim 1 sufficient to treat said disorder and an inert pharmaceutical carrier.

19. A method of treating a condition selected from the group consisting of obesity, anxiety, depression, pain and erectile dysfunction in warm-blooded animals comprising administering to warm-blooded animals in need thereof an amount of a compound of claim 1 sufficient to treat said condition.

20. The method of claim 19 wherein the condition being treated is anxiety and depression.

21. The method of claim 19 wherein the condition being treated is pain.

22. The method of claim 21 wherein the pain is neuropathic pain.

* * * * *